(12) United States Patent
Ohsaka et al.

(10) Patent No.: US 11,978,198 B2
(45) Date of Patent: May 7, 2024

(54) METHOD, APPARATUS, AND COMPUTER PROGRAM FOR SUPPORTING DISEASE ANALYSIS, AND METHOD, APPARATUS, AND PROGRAM FOR TRAINING COMPUTER ALGORITHM

(71) Applicants: JUNTENDO EDUCATIONAL FOUNDATION, Tokyo (JP); SYSMEX CORPORATION, Kobe (JP)

(72) Inventors: Akimichi Ohsaka, Tokyo (JP); Yoko Tabe, Tokyo (JP); Konobu Kimura, Kobe (JP)

(73) Assignees: JUNTENDO EDUCATIONAL FOUNDATION, Tokyo (JP); SYSMEX CORPORATION, Hyogo (JP)

(*) Notice: Subject to any disclaimer, the term of this patent is extended or adjusted under 35 U.S.C. 154(b) by 305 days.

(21) Appl. No.: 16/857,495

(22) Filed: Apr. 24, 2020

(65) Prior Publication Data
US 2020/0340909 A1  Oct. 29, 2020

(30) Foreign Application Priority Data
Apr. 26, 2019  (JP) .................. 2019-086363

(51) Int. Cl.
*G06T 7/00* (2017.01)
*G01N 15/10* (2006.01)
(Continued)

(52) U.S. Cl.
CPC ....... *G06T 7/0012* (2013.01); *G01N 15/1429* (2013.01); *G01N 15/1475* (2013.01);
(Continued)

(58) Field of Classification Search
CPC ........ G16H 10/00–80/00; G06N 3/00–99/007; G01N 1/00–2800/7095;
(Continued)

(56) References Cited

U.S. PATENT DOCUMENTS 5,830,141 A * 11/1998 Makram-Ebeid ..... G06T 7/0012
600/407
10,106,153 B1 * 10/2018 Xiao ....................... G06F 18/24
(Continued)

FOREIGN PATENT DOCUMENTS

CN  103745210 A  4/2014
CN  104732524 A  6/2015
(Continued)

OTHER PUBLICATIONS

Tomita et al., "Differential Diagnosis of Various Thrombocytopenias in Childhood by Analysis of Platelet Volume," Pediat. Res. 14: 133-137 (1980) (Year: 1980).*
(Continued)

*Primary Examiner* — Jonathon A. Szumny
(74) *Attorney, Agent, or Firm* — Crowell & Moring LLP

(57) ABSTRACT

Disclosed is a method for supporting disease analysis, the method including classifying, on the basis of images obtained from a plurality of analysis target cells contained in a specimen collected from a subject, a morphology of each analysis target cell, and obtaining cell morphology classification information corresponding to the specimen, on the basis of a result of the classification; and analyzing a disease of the subject by means of a computer algorithm, on the basis of the cell morphology classification information.

19 Claims, 32 Drawing Sheets

(51) Int. Cl.
| | |
|---|---|
| *G01N 15/14* | (2006.01) |
| *G01N 15/1429* | (2024.01) |
| *G06N 3/045* | (2023.01) |
| *G06N 3/08* | (2023.01) |
| *G06N 20/20* | (2019.01) |
| *G06V 10/82* | (2022.01) |
| *G16H 10/40* | (2018.01) |
| *G16H 30/40* | (2018.01) |
| *G16H 50/20* | (2018.01) |
| *G16H 50/70* | (2018.01) |

(52) U.S. Cl.
CPC ............... *G06N 3/045* (2023.01); *G06N 3/08* (2013.01); *G06N 20/20* (2019.01); *G06V 10/82* (2022.01); *G16H 10/40* (2018.01); *G16H 30/40* (2018.01); *G16H 50/20* (2018.01); *G16H 50/70* (2018.01); *G01N 2015/1006* (2013.01)

(58) Field of Classification Search
CPC .................... G06Q 10/00–2250/905; G06V 10/00–2201/136; G06T 1/00–2219/2024
See application file for complete search history.

(56) References Cited

U.S. PATENT DOCUMENTS

| | | | |
|---|---|---|---|
| 10,134,131 | B1 | 11/2018 | Ando et al. |
| 10,254,286 | B2* | 4/2019 | Pirie-Shepherd .......................... G01N 33/57484 |
| 10,304,188 | B1* | 5/2019 | Kumar ................. G06V 20/695 |
| 10,650,929 | B1* | 5/2020 | Beck ....................... G16H 30/40 |
| 10,977,788 | B2 | 4/2021 | Sasagawa et al. |
| 11,093,729 | B2 | 8/2021 | Ohsaka et al. |
| 11,276,500 | B2* | 3/2022 | Styner .................. G06N 3/0454 |
| 2002/0177574 | A1* | 11/2002 | Taylor .................... A61K 9/0034 514/44 R |
| 2003/0087248 | A1* | 5/2003 | Morrison .............. C12Q 1/6841 435/6.16 |
| 2005/0260580 | A1* | 11/2005 | Verma ................... G01N 33/746 435/6.12 |
| 2008/0015448 | A1* | 1/2008 | Keely ................... A61B 5/0068 600/562 |
| 2008/0033253 | A1* | 2/2008 | Neville .................. G16H 70/60 600/300 |
| 2009/0075903 | A1* | 3/2009 | Siegel ........................ A61P 7/06 514/16.6 |
| 2011/0176710 | A1 | 7/2011 | Mattiuzzi |
| 2012/0190060 | A1 | 7/2012 | Tang |
| 2013/0190194 | A1* | 7/2013 | Tang ....................... G16B 20/00 435/6.12 |
| 2013/0337487 | A1 | 12/2013 | Loewke |
| 2014/0185906 | A1 | 7/2014 | Ding et al. |
| 2014/0206006 | A1* | 7/2014 | Xu ......................... C12Q 1/6869 702/19 |
| 2015/0003701 | A1* | 1/2015 | Klauschen ............ G06T 7/0012 382/128 |
| 2015/0204771 | A1* | 7/2015 | Sun ........................ G06T 7/0012 382/134 |
| 2016/0022238 | A1* | 1/2016 | Park ....................... A61B 6/5217 600/407 |
| 2016/0350914 | A1* | 12/2016 | Champlin .............. G06V 10/56 |
| 2017/0132450 | A1 | 5/2017 | El-Zehiry et al. |
| 2017/0212028 | A1* | 7/2017 | Correia De Matos Nolasco Lamas ............... G01N 15/0227 |
| 2017/0285035 | A1 | 10/2017 | Dittamore |
| 2018/0156700 | A1* | 6/2018 | Natarajan .............. G01N 1/312 |
| 2018/0157916 | A1* | 6/2018 | Doumbouya ........ G06V 40/103 |
| 2018/0157972 | A1* | 6/2018 | Hu ......................... G06V 20/56 |
| 2018/0182099 | A1* | 6/2018 | Lesniak ............... G06K 9/6256 |
| 2018/0211380 | A1 | 7/2018 | Tandon et al. |
| 2018/0247195 | A1 | 8/2018 | Kumar et al. |
| 2018/0315190 | A1 | 11/2018 | Sasagawa et al. |
| 2018/0322327 | A1* | 11/2018 | Smith ................... G06V 10/255 |
| 2019/0034762 | A1* | 1/2019 | Hashimoto .......... G06V 10/764 |
| 2019/0050534 | A1* | 2/2019 | Apte ......................... G16B 5/00 |
| 2019/0080467 | A1* | 3/2019 | Hirzer ...................... G06T 7/73 |
| 2019/0094115 | A1* | 3/2019 | Bhakdi .................. C11D 1/667 |
| 2019/0147337 | A1* | 5/2019 | Yang ........................ G06N 3/08 706/25 |
| 2019/0256885 | A1* | 8/2019 | Nanjo ................... G06T 7/0012 |
| 2019/0302000 | A1* | 10/2019 | Lo .......................... G01J 3/0208 |
| 2019/0384047 | A1* | 12/2019 | Johnson ............... A61B 5/0275 |
| 2020/0026962 | A1* | 1/2020 | Sha ........................ G03F 7/705 |
| 2020/0126234 | A1 | 4/2020 | Yokota |
| 2020/0151877 | A1* | 5/2020 | Hattori ................... G06V 20/69 |
| 2020/0152326 | A1* | 5/2020 | Sanchez-Martin .... G06N 20/00 |
| 2020/0202514 | A1* | 6/2020 | Yang ........................ G06T 7/11 |
| 2020/0340909 | A1 | 10/2020 | Ohsaka |
| 2020/0370130 | A1* | 11/2020 | Sussman ................ G16B 20/50 |
| 2020/0372235 | A1* | 11/2020 | Peng ....................... G01N 1/30 |
| 2020/0380672 | A1* | 12/2020 | Clark ....................... G06T 7/73 |
| 2021/0004650 | A1* | 1/2021 | Frank .................... G06T 7/136 |
| 2021/0020314 | A1* | 1/2021 | Ehrich .................. G06N 3/082 |
| 2021/0033599 | A1* | 2/2021 | Kiyuna ................. G16H 20/10 |

FOREIGN PATENT DOCUMENTS

| | | | | |
|---|---|---|---|---|
| CN | 106127255 A | * | 11/2016 | ............... G06K 9/46 |
| JP | H10-197522 A | | 7/1998 | |
| JP | 2008-533440 A | | 8/2008 | |
| JP | 2009-044974 A | | 3/2009 | |
| JP | 2011-229413 A | | 11/2011 | |
| JP | 2016-534709 A | | 11/2016 | |
| JP | 2017-516992 A | | 6/2017 | |
| JP | 2018-185759 A | | 11/2018 | |
| WO | WO 2006/083969 A2 | | 8/2006 | |
| WO | WO 2015/177268 A1 | | 11/2015 | |
| WO | WO 2017/155869 A1 | | 9/2017 | |
| WO | WO-2017155869 A1 | * | 9/2017 | ............. C11D 1/667 |
| WO | WO-2018156133 A1 | * | 8/2018 | ......... G01N 33/4833 |
| WO | WO 2019/039595 A1 | | 2/2019 | |
| WO | WO-2019100032 A2 | * | 5/2019 | ............ G06K 9/6259 |

OTHER PUBLICATIONS

Madabhushi et al., "Image analysis and machine learning in digital pathology: Challenges and opportunities," Medical Image Analysis 33 (2016) 170-175 (Year: 2016).*

Jones et al., "Scoring diverse cellular morphologies in image-based screens with iterative feedback and machine learning," PNAS Feb. 10, 2009, vol. 106, No. 6, pp. 1826-1831. (Year: 2009).*

Handfield et al., "Unsupervised Clustering of Subcellular Protein Expression Patterns in High-Throughput Microscopy Images Reveals Protein Complexes and Functional Relationships between Proteins," PLOS Computational Biology | www.ploscompbiol.org | Jun. 2013 | vol. 9 | Issue 6 | e1003085 (Year: 2013).*

Zheng et al., "Direct Neural Network Application for Automated Cell Recognition", Cytometry Part A, 2004, vol. 57A, No. 1, pp. 1-9.

Kim et al., "Analyzing Blood Cell Image to Distinguish Its Abnormalities", Proceedings ACM Multimedia, 2000, pp. 395-397.

Extended European Search Report dated Sep. 22, 2020 for the related European patent Application No. 20171050.6, 10 pages.

Office Action dated Jan. 5, 2022 for the corresponding European patent application No. 19172959.9, 6 pages.

Abbas et al., "Microscopic RGB Color Images Enhancement for Blood Cells Segmentation in YCbCr Color Space for K-Means Clustering", Journal of Theoretical and Applied Information Technology, 2013, vol. 55, No. 1, pp. 117-125, dated Sep. 10, 2013, 9 pages.

Diaz et al., "Infected Cell Identification in Thin Blood Images Based on Color Pixel Classification: Comparison and Analysis", CIARP 2007: Progress in Pattern Recognition, Image Analysis and Applications, 2007, pp. 812-821, 10 pages.

Extended European Search Report dated Mar. 27, 2020, for the corresponding European patent application No. 19172959.9, 13 pages.

(56) References Cited

OTHER PUBLICATIONS

Extended European Search Report for Europe Application No. 20171050.6, dated Sep. 22, 2020, 10 pages.
Office Action in U.S. Appl. No. 16/406,523, dated Nov. 16, 2020, 25 pages.
D8 Office Action in U.S. Appl. No. 16/406,523, dated Nov. 16, 2020, 25 pages.
ICIIS, 2017, 1570376781, Arna Ghosh et al., "Simultaneous Localization and Classificaion of Acute Lymphoblastic Leukemic Cells in Peripheral Blood Smears Using a Deep Convolutional Network with Average Pooling Layer," pp. 1-6, (Year: 2017).
Human Cell, 2018, vol. 31, Hirohiko Niioka et al., "Classification of C2C12 cells at differentiation by convolutional neural network of deep learning using phase contrast images", pp. 87-93, (Year: 2017),
Office Action dated Mar. 15, 2022 for JP patent application No. 2018-091776, including English translation, 10 pages.
Partial European Search Report for Europe Application No. 19172959.9, dated Nov. 19, 2019, 14 pages.
Blood Disease Commentary, obtained from the Internet on Mar. 30, 2022, from URL Address: <http://www.med.osaka-cu.ac.jp/labmed/page074.html>, including English translation, 4 pages.

Office Action dated Jun. 2, 2022 for European patent application No. 20171050.6.
Decision of Refusal with English Translation, dated Oct. 25, 2022, pp. 1-7, for Japanese Patent Application No. 2018-091776, Japanese Patent Office, Tokyo, Japan.
Japanese Office Action with English Translation, dated Feb. 7, 2023, pp. 1-3, issued in Japanese patent application No. 2019-086363, Japan Patent Office, Chiyoda Tokyo, Japan.
US Office Action, dated Mar. 9, 2023, pp. 1-16, issued in U.S. Appl. No. 17/398,850, United States Patent and Trademark Office, Alexandria, Virginia.
Brieu et al., "Context-based Interpolation of Coarse Deep Learning Prediction Maps for the Segmentation of Fine Structures in Immunofluorescence Images" Progress in Biomedical Optics and Imaging, SPIE, 2018, vol. 10581, pp. 105810P_1-6, 6 pages.
Office Action dated Dec. 19, 2023 for the corresponding European patent application No. 19172959.9, 6 pages.
Summons dated Nov. 30, 2023 for the corresponding European patent application No. 20171050.6, 10 pages.
Office Action dated Dec. 5, 2023 for the corresponding Japanese patent application No. 2023-008570, including English translation, 10 pages.

* cited by examiner

FIG. 3A

| CELL TYPE | LABEL VALUE | CELL TYPE | ABNORMAL FINDING | LABEL VALUE |
|---|---|---|---|---|
| NOT APPLICABLE | 0 | BLAST (BL) | AUER ROD | 21 |
| SEGMENTED NEUTROPHIL | 1 | | NUCLEUS MORPHOLOGY ABNORMALITY | 22 |
| BAND NEUTROPHIL | 2 | | ABNORMAL GRANULE | 23 |
| METAMYELOCYTE | 3 | | VACUOLE | 24 |
| MYELOCYTE | 4 | | SMUDGE | 25 |
| PROMYELOCYTE | 5 | | APOPTOSIS (KARYOLYSIS IMAGE) | 26 |
| BLAST | 6 | | OTHER ABNORMALITIES | 27 |
| LYMPHOCYTE | 7 | PROMYELOCYTE (PMY) | AUER ROD | 30 |
| ATYPICAL LYMPHOCYTE | 8 | | FAGOTT CELL | 31 |
| MONOCYTE | 9 | | NUCLEUS MORPHOLOGY ABNORMALITY | 32 |
| EOSINOPHIL | 10 | | ABNORMAL GRANULE | 33 |
| BASOPHIL | 11 | | DEGRANULATION (INCLUDING NO GRANULATION) | 34 |
| ERYTHROBLAST | 12 | | VACUOLE | 35 |
| PLATELET | 13 | | SMUDGE | 36 |
| PLATELET AGGREGATE | 14 | | APOPTOSIS (KARYOLYSIS IMAGE) | 37 |
| MEGAKARYOCYTE | 15 | | OTHER ABNORMALITIES | 38 |
| SMUDGE | 16 | MYELOCYTE (MY) | AUER ROD | 40 |
| ARTIFACT | 17 | | NUCLEUS MORPHOLOGY ABNORMALITY | 41 |
| | | | ABNORMAL GRANULE | 42 |
| | | | DEGRANULATION (INCLUDING NO GRANULATION) | 43 |
| | | | VACUOLE | 44 |
| | | | SMUDGE | 45 |
| | | | APOPTOSIS (KARYOLYSIS IMAGE) | 46 |
| | | | OTHER ABNORMALITIES | 47 |
| | | METAMYELOCYTE (MMY) | AUER ROD | 50 |
| | | | NUCLEUS MORPHOLOGY ABNORMALITY | 51 |
| | | | ABNORMAL GRANULE | 52 |
| | | | DEGRANULATION (INCLUDING NO GRANULATION) | 53 |
| | | | VACUOLE | 54 |
| | | | GIANT | 55 |
| | | | SMUDGE | 56 |
| | | | APOPTOSIS (KARYOLYSIS IMAGE) | 57 |
| | | | OTHER ABNORMALITIES | 58 |
| | | BAND NEUTROPHIL (BN) | AUER ROD | 60 |
| | | | SPHERICAL/ELLIPTICAL NUCLEUS (HYPOSEGMENTATED NUCLEUS) | 61 |
| | | | RING-SHAPED NUCLEUS | 62 |
| | | | NUCLEUS MORPHOLOGY ABNORMALITY OTHER THAN ABOVE | 63 |
| | | | GIANT | 64 |
| | | | DEGRANULATION (INCLUDING NO GRANULATION) | 65 |
| | | | GRANULE DISTRIBUTION ABNORMALITY | 66 |
| | | | TOXIC GRANULE | 67 |
| | | | DOHLE BODY | 68 |
| | | | VACUOLE | 69 |
| | | | SMUDGE | 70 |
| | | | APOPTOSIS (KARYOLYSIS IMAGE) | 71 |
| | | | SATELLITISM | 72 |
| | | | PSEUDO CHEDIAK-HIGASHI GRANULE-LIKE | 73 |
| | | | OTHER ABNORMALITIES | 74 |
| | | SEGMENTED NEUTROPHIL (SN) | AUER ROD | 80 |
| | | | PSEUDO-PELGER (HYPOSEGMENTATED NUCLEUS) | 81 |
| | | | RING-SHAPED NUCLEUS | 82 |
| | | | HYPERSEGMENTATION | 83 |
| | | | NUCLEUS MORPHOLOGY ABNORMALITY OTHER THAN ABOVE | 84 |
| | | | GIANT | 85 |
| | | | DEGRANULATION (INCLUDING NO GRANULATION) | 86 |
| | | | GRANULE DISTRIBUTION ABNORMALITY | 87 |
| | | | TOXIC GRANULE | 88 |
| | | | DOHLE BODY | 89 |
| | | | VACUOLE | 90 |
| | | | SMUDGE | 91 |
| | | | APOPTOSIS (KARYOLYSIS IMAGE) | 92 |
| | | | SATELLITISM | 93 |
| | | | PSEUDO CHEDIAK-HIGASHI GRANULE-LIKE | 94 |
| | | | OTHER ABNORMALITIES | 95 |

FIG. 3B

| CELL TYPE | ABNORMAL FINDING | LABEL VALUE | CELL TYPE | ABNORMAL FINDING | LABEL VALUE |
|---|---|---|---|---|---|
| NEUTROPHIL (GN) | AUER ROD | 101 | ERYTHROBLAST (EB) | MEGALOBLAST-LIKE | 170 |
| | PSEUDO-PELGER (HYPOSEGMENTATED NUCLEUS) | 102 | | IRREGULAR NUCLEAR CONTOUR | 171 |
| | SPHERICAL/ELLIPTICAL NUCLEUS (HYPOSEGMENTATED NUCLEUS) | 103 | | NUCLEAR FRAGMENTATION | 172 |
| | RING-SHAPED NUCLEUS | 104 | | KARYOLYSIS | 173 |
| | HYPERSEGMENTATION | 105 | | INTERNUCLEAR BRIDGING | 174 |
| | NUCLEUS MORPHOLOGY ABNORMALITY OTHER THAN ABOVE | 106 | | MULTIPLE NUCLEI | 175 |
| | GIANT | 107 | | NUCLEAR DIVISION | 176 |
| | DEGRANULATION (INCLUDING NO GRANULATION) | 108 | | ENUCLEATION | 177 |
| | GRANULE DISTRIBUTION ABNORMALITY | 109 | | INTRACELLULAR INCLUSION BODY | 178 |
| | TOXIC GRANULE | 110 | | SMUDGE | 179 |
| | DOHLE BODY | 111 | | APOPTOSIS (KARYOLYSIS IMAGE) | 180 |
| | VACUOLE | 112 | | OTHER ABNORMALITIES | 181 |
| | SMUDGE | 113 | PLATELET (PLT) | GIANT | 190 |
| | APOPTOSIS (KARYOLYSIS IMAGE) | 114 | | | |
| | SATELLITISM | 115 | | MALFORMATION | 191 |
| | PSEUDO CHEDIAK-HIGASHI GRANULE-LIKE | 116 | | | |
| | OTHER ABNORMALITIES | 117 | | SMUDGE | 192 |
| EOSINOPHIL (EO) | NUCLEUS MORPHOLOGY ABNORMALITY | 120 | | OTHER ABNORMALITIES (INCLUDING AGGREGATION) | 193 |
| | ABNORMAL GRANULE | 121 | | | |
| | GRANULE DISTRIBUTION ABNORMALITY | 122 | | | |
| | IMMATURE | 123 | MEGAKARYOCYTE (MK) | BARE NUCLEUS | 200 |
| | VACUOLE | 124 | | | |
| | SMUDGE | 125 | | SMUDGE | 201 |
| | APOPTOSIS (KARYOLYSIS IMAGE) | 126 | | | |
| | OTHER ABNORMALITIES | 127 | | OTHER ABNORMALITIES | 202 |
| BASOPHIL (BA) | NUCLEUS MORPHOLOGY ABNORMALITY | 130 | | | |
| | ABNORMAL GRANULE | 131 | | | |
| | GRANULE DISTRIBUTION ABNORMALITY | 132 | | | |
| | IMMATURE | 133 | | | |
| | SMUDGE | 134 | | | |
| | APOPTOSIS (KARYOLYSIS IMAGE) | 135 | | | |
| | OTHER ABNORMALITIES | 136 | | | |
| LYMPHOCYTE (LY) | PLASMA CELL-LIKE | 140 | | | |
| | CLEAVED NUCLEUS | 141 | | | |
| | PETAL-LIKE NUCLEUS | 142 | | | |
| | MULTIPLE NUCLEI | 143 | | | |
| | INCREASED N/C RATIO | 144 | | | |
| | NUCLEOLUS | 145 | | | |
| | NUCLEORETICULUM ABNORMALITY | 146 | | | |
| | NUCLEUS MORPHOLOGY ABNORMALITY OTHER THAN ABOVE | 147 | | | |
| | HAIRY CELL-LIKE | 148 | | | |
| | BLEB-LIKE | 149 | | | |
| | GRANULAR | 150 | | | |
| | VACUOLE | 151 | | | |
| | SMUDGE | 152 | | | |
| | APOPTOSIS (KARYOLYSIS IMAGE) | 153 | | | |
| | OTHER ABNORMALITIES | 154 | | | |
| ATYPICAL LYMPHOCYTE (VLY) | GRANULAR | 150 | | | |
| | VACUOLE | 151 | | | |
| | SMUDGE | 152 | | | |
| | APOPTOSIS (KARYOLYSIS IMAGE) | 153 | | | |
| | NUCLEOLUS | 154 | | | |
| | NUCLEUS MORPHOLOGY ABNORMALITY (OTHERS) | 155 | | | |
| | OTHER ABNORMALITIES | 156 | | | |
| MONOCYTE (MO) | NUCLEUS MORPHOLOGY ABNORMALITY | 160 | | | |
| | ABNORMAL GRANULE | 161 | | | |
| | SMUDGE | 162 | | | |
| | APOPTOSIS (KARYOLYSIS IMAGE) | 163 | | | |
| | OTHER ABNORMALITIES | 164 | | | |

FIG. 4

|   | A | B | C | D | E | F |
|---|---|---|---|---|---|---|
|   |   |   | PROBABILITY FOR EACH CELL | | | SUM OF PROBABILITY PER SPECIMEN |
|   |   | CELL No | 1 | 2 | 3 | |
| 1 | ABNORMAL FINDING | DEGRANULATION | 0.8 | 0 | 0 | 0.8 |
| 2 | | AUER ROD | 0 | 0 | 0 | 0 |
| 3 | | SPHERICAL NUCLEUS | 0 | 0 | 0 | 0 |
| 4 | | HYPERSEGMENTATION | 0.7 | 0 | 0 | 0.7 |
| 5 | | MEGATHROMBOCYTE | 0 | 0.9 | 0 | 0.9 |
| 6 | TYPE OF CELL | SEGMENTED NEUTROPHIL | 0.5 | 0 | 0 | 0.5 |
| 7 | | BAND NEUTROPHIL | 0.2 | 0 | 0 | 0.2 |
| 8 | | LYMPHOCYTE | 0 | 0 | 0.3 | 0.3 |
| 9 | | MONOCYTE | 0.1 | 0 | 0.3 | 0.4 |
| 10 | | EOSINOPHIL | 0.1 | 0 | 0 | 0.1 |
| 11 | | BASOPHIL | 0.1 | 0 | 0 | 0.1 |
| 12 | | BLAST | 0 | 0 | 0.4 | 0.4 |
| 13 | | PLATELET | 0 | 1 | 0 | 1 |
| 14 | ABNORMAL FINDING | DEGRANULATION OF NEUTROPHIL | 0.8 | 0 | 0 | 0.8 |
| 15 | | AUER ROD OF BLAST | 0 | 0 | 0 | 0 |
| 16 | | SPHERICAL NUCLEUS OF NEUTROPHIL | 0 | 0 | 0 | 0 |
| 17 | | HYPERSEGMENTATION OF NEUTROPHIL | 0.7 | 0 | 0 | 0.7 |
| 18 | | MEGATHROMBOCYTE | 0 | 0.9 | 0 | 0.9 |
| 19 | DISEASE NAME | MYELODYSPLASTIC SYNDROME | | | | |

FIG. 23

| Cell type | Images for training | Images for validation |
|---|---|---|
| Segmented Neutrophil | 315777 | 1432 |
| Band Neutrophil | 19191 | 896 |
| Metamyelocyte | 2235 | 196 |
| Myelocyte | 4596 | 418 |
| Promyelocyte | 699 | 70 |
| Blast | 11237 | 790 |
| Lymphocyte | 149524 | 1177 |
| Variant Lymphocyte | 4521 | 262 |
| Monocyte | 36734 | 641 |
| Eosinophil | 18186 | 705 |
| Basophil | 2808 | 205 |
| Large Platelet | 62985 | 631 |
| Megakaryocyte | 453 | 31 |
| Platelet Aggregation | 2541 | 208 |
| Erythroblast | 4823 | 409 |
| Smudge | 54027 | 391 |
| Artifact | 6693 | 478 |

FIG. 24

| Cell type | Sensitivity (%) | Specificity (%) |
|---|---|---|
| Segmented Neutrophil | 98.0 | 97.7 |
| Band Neutrophil | 98.0 | 97.0 |
| Metamyelocyte | 93.9 | 96.0 |
| Myelocyte | 98.1 | 96.9 |
| Promyelocyte | 98.6 | 97.6 |
| Blast | 97.2 | 98.7 |
| Lymphocyte | 99.3 | 96.5 |
| Variant Lymphocyte | 95.0 | 98.2 |
| Monocyte | 98.5 | 99.1 |
| Eosinophil | 99.6 | 100.0 |
| Basophil | 98.5 | 99.5 |
| Large Platelet | 99.7 | 99.4 |
| Megakaryocyte | 93.5 | 99.6 |
| Platelet Aggregation | 95.7 | 99.3 |
| Erythroblast | 99.6 | 99.4 |
| Smudge | 95.4 | 98.0 |
| Artifact | 99.0 | 98.7 |

FIG. 25

| Cell type | Sensitivity (%) | Specificity (%) | AUC | Images for validation |
|---|---|---|---|---|
| Blast | | | | |
| abnormal shape of nuclei | 95.3 | 94.4 | 0.975 | 107 |
| abnormal granulation | 86.5 | 96.4 | 0.926 | 62 |
| vacuoles | 92 | 94.5 | 0.950 | 112 |
| Neutrophil | | | | |
| Pelger-Huet anomaly | 93.4 | 95.9 | 0.960 | 61 |
| spherical /ovoid nucleus | 96.2 | 97.4 | 0.978 | 53 |
| hypersegmentation | 81.3 | 97.5 | 0.904 | 64 |
| degranulation | 86.2 | 92.6 | 0.955 | 130 |
| abnormal granulation | 98.3 | 82.2 | 0.986 | 173 |
| giant | 91.8 | 93.9 | 0.977 | 233 |
| vacuoles | 91.9 | 93.8 | 0.931 | 106 |
| toxic granulations | 95.9 | 97.3 | 0.992 | 344 |
| Dohle body | 90.5 | 86.6 | 0.947 | 84 |
| Lymphocyte | | | | |
| cleaved nuclei | 93.5 | 96.2 | 0.969 | 139 |
| increased N:C ratio | 94.7 | 95 | 0.966 | 75 |
| abnormal chromatin | 92.2 | 94.7 | 0.958 | 90 |
| abnormal shape of nuclei | 92.9 | 92.6 | 0.953 | 113 |
| granular lymphocyte | 82.5 | 94.6 | 0.903 | 164 |
| vacuoles | 81.8 | 92.6 | 0.893 | 110 |
| Erythroblast | | | | |
| irregular shape | 80 | 59.9 | 0.878 | 55 |
| Large platelet | | | | |
| giant platelet | 61.5 | 97.5 | 0.801 | 174 |

METHOD, APPARATUS, AND COMPUTER PROGRAM FOR SUPPORTING DISEASE ANALYSIS, AND METHOD, APPARATUS, AND PROGRAM FOR TRAINING COMPUTER ALGORITHM

RELATED APPLICATIONS

This application claims priority to Japanese Patent Application No. 2019-086363, filed on Apr. 26, 2019, the entire content of which is incorporated herein by reference.

BACKGROUND OF THE INVENTION

1. Field of the Invention

The present invention relates to a method, an apparatus, and a computer program that support disease analysis, and a method, an apparatus, and a program that train a computer algorithm for supporting disease analysis.

2. Description of the Related Art

Japanese Laid-Open Patent Publication No. H10-197522 describes a method for distinguishing between a pathologic tissue that shows a "hard cancer pattern" and one that shows an "endocapillary fibrous tumor pattern" by inputting two kinds of feature quantities to a neural network. One of the feature quantities is calculated by using the number, area, shape, roundness, color, and chromaticity of nuclear regions, the number, area, shape, and roundness of cavity regions, the number, area, shape, roundness, color, and chromaticity of interstitium regions, and the number, area, shape, and roundness of lumen regions, which are extracted from a tissue image, the texture of the image, and a wavelet transform value. The other of the feature quantities is calculated by using the degree of a two-layer structure in which epithelial cells are accompanied by myoepithelial cells, the degree of fibrillization, the presence or absence of a papillary pattern, the presence or absence of a cribriform pattern, the presence or absence of a necrotic substance, the presence or absence of a solid pattern, and the color or chromaticity of the image.

SUMMARY OF THE INVENTION

The scope of the present invention is defined solely by the appended claims, and is not affected to any degree by the statements within this summary.

Japanese Laid-Open Patent Publication No. H10-197522 discloses discernment of a disease on the basis of an image of a tissue, but does not disclose discernment of a disease based on individual cell images.

The present invention relates to a method for supporting disease analysis. The method includes classifying, on the basis of images obtained from a plurality of analysis target cells contained in a specimen collected from a subject, a morphology of each analysis target cell, and obtaining cell morphology classification information corresponding to the specimen, on the basis of a result of the classification; and analyzing a disease of the subject by means of a computer algorithm, on the basis of the cell morphology classification information. According to these configurations, a disease can be discerned on the basis of individual cell images.

Preferably, the classifying of the morphology of each analysis target cell includes discerning a type of cell of each analysis target cell. More preferably, the cell morphology classification information is information regarding a cell number for each type of cell (64). According to these configurations, a disease can be discerned on the basis of individual types of cells.

Preferably, the classifying of the morphology of each analysis target cell includes discerning a type of abnormal finding in each analysis target cell. More preferably, the cell morphology classification information is information regarding a cell number for each type of abnormal finding (63). According to these configurations, a disease can be discerned on the basis of the types of abnormal findings in individual cells.

The classifying of the morphology of each analysis target cell includes discerning a type of abnormal finding for each type of cell of the analysis target cell. According to these configurations, a disease can be more accurately discerned on the basis of individual cell images.

The classifying of the morphology of each analysis target cell includes inputting analysis data that includes information regarding each analysis target cell, to a deep learning algorithm having a neural network structure, and classifying the morphology of each analysis target cell by means of the deep learning algorithm. According to these configurations, a disease can be more accurately discerned.

The computer algorithm is a machine learning algorithm, and the analyzing of the disease of the subject is performed by inputting the cell morphology classification information as a feature quantity to the machine learning algorithm (67). According to these configurations, a disease can be more accurately discerned.

Preferably, the machine learning algorithm (67) is selected from tree, regression, neural network, Bayes, clustering, or ensemble learning. More preferably, the machine learning algorithm is gradient boosting tree. By using these machine learning algorithms, a disease can be more accurately discerned.

The obtaining of the cell morphology classification information includes obtaining a probability that each analysis target cell belongs to each of a plurality of cell morphology classifications, calculating a sum of the probability for each type of the cell morphology classifications, and obtaining the sum as the cell morphology classification information. According to these configurations, more accurate disease discernment can be realized.

Preferably, the specimen is a blood specimen. Since cells in blood reflect pathologies of various diseases, more accurate disease discernment can be realized.

Preferably, the disease is a hematopoietic system disease. According to the present invention, a hematopoietic system disease can be accurately discerned.

The hematopoietic system disease is aplastic anemia or myelodysplastic syndrome. According to the present invention, a hematopoietic system disease can be accurately discerned.

Preferably, the abnormal finding is at least one type selected from the group consisting of: nucleus morphology abnormality; granulation abnormality; cell size abnormality; cell malformation; cytoclasis; vacuole; immature cell; presence of inclusion body; Döhle body; satellitism; nucleoreticulum abnormality; petal-like nucleus; increased N/C ratio; and bleb-like, smudge, and hairy cell-like morphologies By evaluating these abnormal findings in these cells, more accurate disease discernment can be realized.

Preferably, the nucleus morphology abnormality includes at least one type selected from hypersegmentation, hyposegmentation, pseudo-Pelger anomaly, ring-shaped nucleus, spherical nucleus, elliptical nucleus, apoptosis, polynuclearity, karyorrhexis, enucleation, bare nucleus, irregular nuclear contour, nuclear fragmentation, internuclear bridging, multiple nuclei, cleaved nucleus, nuclear division, and nucleolus abnormality. The granulation abnormality includes at least one type selected from degranulation, granule distribution abnormality, toxic granule, Auer rod, Fagott cell, and pseudo Chediak-Higashi granule-like granule. The cell size abnormality includes megathrombocyte. By evaluating these abnormal findings, more accurate disease discernment can be realized.

Preferably, the type of cell includes at least one type selected from neutrophil, eosinophil, platelet, lymphocyte, monocyte, and basophil. By evaluating these types of cells, more accurate disease discernment can be realized.

More preferably, the type of cell further includes at least one type selected from metamyelocyte, myelocyte, promyelocyte, blast, plasma cell, atypical lymphocyte, immature eosinophil, immature basophil, erythroblast, and megakaryocyte. By evaluating these types of cells in those cells, more accurate disease discernment can be realized.

The present invention relates to an apparatus (200) for supporting disease analysis. The apparatus (200) includes a processing unit (20). The processing unit (20) classifies, on the basis of images obtained from a plurality of analysis target cells contained in a specimen collected from a subject, a morphology of each analysis target cell, and obtains cell morphology classification information corresponding to the specimen, on the basis of a result of the classification; and analyzes a disease of the subject by means of a computer algorithm, on the basis of the cell morphology classification information.

The present invention relates to a computer-readable storage medium having stored therein a program for supporting disease analysis. The program is configured to cause a computer to execute classifying, on the basis of images obtained from a plurality of analysis target cells contained in a specimen collected from a subject, a morphology of each analysis target cell, and obtaining cell morphology classification information corresponding to the specimen, on the basis of a result of the classification; and analyzing a disease of the subject by means of a computer algorithm, on the basis of the cell morphology classification information.

According to the apparatus or the program for supporting disease analysis, accurate disease discernment can be realized.

The present invention relates to a training method for a computer algorithm for supporting disease analysis. The training method includes classifying, on the basis of images obtained from a plurality of analysis target cells contained in a specimen collected from a subject, a morphology of each analysis target cell, and obtaining cell morphology classification information corresponding to the specimen, on the basis of a result of the classification; and inputting the obtained cell morphology classification information as first training data and disease information of the subject as second training data, to the computer algorithm.

The present invention relates to a training apparatus (100) for a computer algorithm for supporting disease analysis. The training apparatus (100) includes a processing unit (10). The processing unit (10) classifies, on the basis of images obtained from a plurality of analysis target cells contained in a specimen collected from a subject, a morphology of each analysis target cell, obtains cell morphology classification information corresponding to the specimen, on the basis of a result of the classification, and inputs the obtained cell morphology classification information as first training data and disease information (55) of the subject as second training data, to the computer algorithm.

The present invention relates to a computer-readable storage medium having stored therein a training program for a computer algorithm for supporting disease analysis. The training program is configured to cause a computer to execute classifying, on the basis of images obtained from a plurality of analysis target cells contained in a specimen collected from a subject, a morphology of each analysis target cell, and obtaining cell morphology classification information corresponding to the specimen, on the basis of a result of the classification; and inputting the cell morphology classification information as first training data and disease information (55) of the subject as second training data, to the computer algorithm.

According to the training method, the training apparatus (100), or the training program, accurate disease discernment can be realized.

BRIEF DESCRIPTION OF THE DRAWINGS

FIG. 3A shows an example of a label value;

FIG. 3B shows an example of the label value;

FIG. 4 shows an example of machine learning training data;

FIG. 23 is a table showing the number of cells used as training data for a deep learning algorithm and the number of cells used in validation for evaluating the performance of the trained deep learning algorithm;

FIG. 24 is a table showing a result of evaluation of the performance of a trained 2nd deep learning algorithm;

FIG. 25 is a table showing a result of evaluation of the performance of a trained 1st deep learning algorithm;

DETAILED DESCRIPTION OF THE PREFERRED EMBODIMENTS

Figure 1:
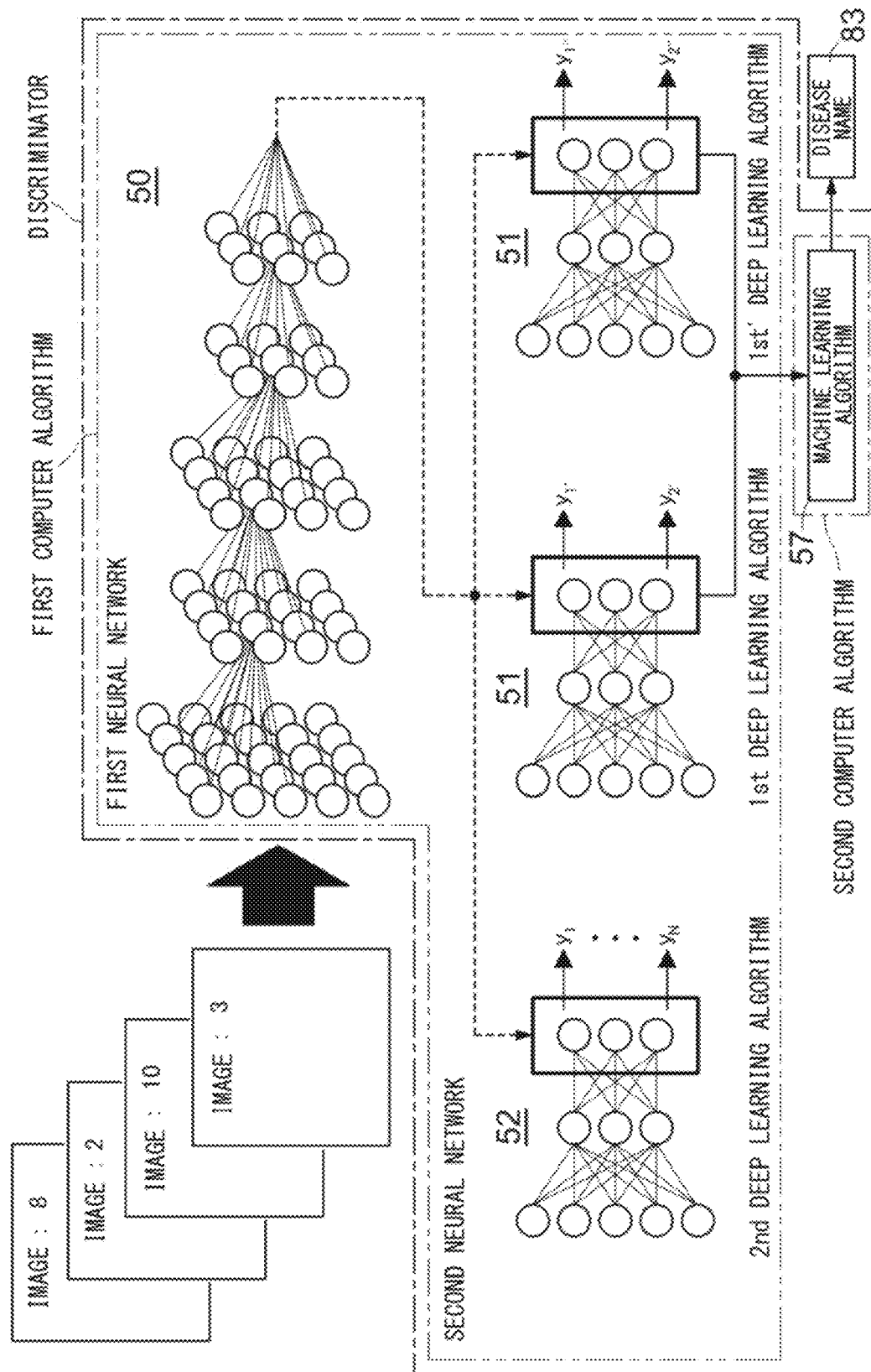
FIG. 1 shows an outline of a support method using a discriminator.

Hereinafter, embodiments of the present disclosure will be described in detail with reference to the attached drawings. In the description below and the drawings, the same reference characters represent the same or similar components. Thus, description of the same or similar components is not repeated.

A method for supporting analysis of a disease of a subject (hereinafter, sometimes simply referred to as "support method") will be described. The support method includes classifying a morphology of each analysis target cell, and analyzing a disease of the subject on the basis of the classification result. On the basis of images obtained from a plurality of analysis target cells contained in a specimen collected from a subject, the morphology of each analysis target cell is classified, and on the basis of the classification result, cell morphology classification information corresponding to the specimen is obtained. The support method includes analyzing a disease of the subject on the basis of information regarding the type of abnormal finding (hereinafter, sometimes referred to as "first information") as the cell morphology classification information. The first information is information regarding the type of abnormal finding that is obtained on the basis of the type of abnormal finding detected from each of a plurality of analysis target cells contained in the specimen, and that corresponds to the specimen. The abnormal finding is discerned on the basis of an image obtained by capturing an analysis target cell. The support method includes analyzing a disease of the subject on the basis of information regarding the type of cell (hereinafter, sometimes referred to as "second information") as the cell morphology classification information. The second information is information regarding the type of cell that is obtained on the basis of the type of cell of each of a plurality of analysis target cells contained in the specimen, and that corresponds to the specimen. The type of cell is discerned on the basis of an image obtained by capturing an analysis target cell.

The subject may be any animal for which a disease is to be analyzed. Examples of the animal include human, dog, cat, rabbit, and monkey. Preferably, the subject is a human.

The disease may be any disease that the above-mentioned animal has. For example, the disease can include tumors of tissues other than the hematopoietic organ system, diseases of the hematopoietic organ system, metabolic diseases, renal diseases, infectious diseases, allergic diseases, autoimmune diseases, traumatic injuries, and the like.

The tumors of tissues other than the hematopoietic organ system can include benign epithelial tumor, benign non epithelial tumor, malignant epithelial tumor, and malignant non epithelial tumor. Preferable examples of the tumors of tissues other than the hematopoietic organ system include malignant epithelial tumor and malignant non epithelial tumor.

Examples of the diseases of the hematopoietic organ system include tumor, anemia, plethora, platelet disorder, and myelofibrosis. Preferable examples of the hematopoietic system tumor include: myelodysplastic syndrome; leukemia (acute myeloblastic leukemia, acute myeloblastic leukemia (involving neutrophil differentiation), acute promyelocytic leukemia, acute myelomonocytic leukemia, acute monocytic leukemia, erythroleukemia, acute megakaryoblastic leukemia, acute myeloid leukemia, acute lymphoblastic leukemia, lymphoblastic leukemia, chronic myelogenous leukemia, chronic lymphocytic leukemia, and the like); malignant lymphoma (Hodgkin's lymphoma, non-Hodgkin's lymphoma, and the like); multiple myeloma; and granuloma. Malignant tumors of the hematopoietic system are preferably myelodysplastic syndrome, leukemia, and multiple myeloma, and more preferably, myelodysplastic syndrome.

Examples of anemia include aplastic anemia, iron-deficiency anemia, megaloblastic anemia (including vitamin B12 deficiency, folate deficiency, and the like), hemorrhagic anemia, renal anemia, hemolytic anemia, thalassemia, sideroblastic anemia, and atransferrinemia. Anemia is preferably aplastic anemia, pernicious anemia, iron-deficiency anemia, or sideroblastic anemia, and more preferably aplastic anemia.

Plethora can include polycythemia vera and secondary polycythemia. Preferably, plethora is polycythemia vera.

Platelet disorder can include thrombocytopenia, thrombocytosis, and megakaryocyte abnormality. Thrombocytopenia can include disseminated intravascular coagulation, idiopathic thrombocytopenic purpura, MYH9 disorder, Bernard-Soulier syndrome, and the like. Thrombocytosis can include essential thrombocythemia. Megakaryocyte abnormality can include small megakaryocyte, multinucleated megakaryocyte, platelet hypoplasia, and the like.

Myelofibrosis can include primary myelofibrosis and secondary myelofibrosis.

Metabolic diseases can include carbohydrate metabolism abnormality, lipid metabolism abnormality, electrolyte abnormality, metal metabolism abnormality, and the like. The carbohydrate metabolism abnormality can include mucopolysaccharidosis, diabetes, and glycogenosis. Preferably, carbohydrate metabolism abnormality is mucopolysaccharidosis and diabetes. Lipid metabolism abnormality can include Gaucher's disease, Niemann-Pick disease, hyperlipidemia, and atherosclerotic disease. Atherosclerotic disease can include arteriosclerosis, atherosclerosis, thrombosis, embolism, and the like. Electrolyte abnormality can include hyperkalemia, hypokalemia, hypernatremia, hyponatremia, and the like. Metal metabolism abnormality can include iron metabolism abnormality, copper metabolism abnormality, calcium metabolism abnormality, and inorganic phosphorus metabolism abnormality.

Nephropathy can include nephrotic syndrome, renal impairment, acute renal failure, chronic kidney disease, renal failure, and the like.

Infectious diseases can include bacterial infection, viral infection, rickettsial infection, chlamydial infection, fungal infection, protozoan infection, and parasitic infection.

Pathogenic bacteria of bacterial infections are not limited in particular. Examples of pathogenic bacteria include coliform bacteria, *Staphylococci, Streptococci, Haemophilus* bacteria, *Neisseria* bacteria, *Moraxella* bacteria, *Listeria* bacteria, *Corynebacterium diphtheria, Clostridium* bacteria, *Helicobacter* bacteria, and *Mycobacterium tuberculosis* complex.

Pathogenic viruses of viral infections are not limited in particular. Examples of the pathogenic viruses include influenza virus, measles virus, rubella virus, varicellovirus, dengue fever virus, cytomegalovirus, EB virus, enterovirus, human immunodeficiency virus, HTLV-1 (human T-lymphotropic virus type-I), rabies virus, and the like.

Pathogenic fungi of fungal infections are not limited in particular. Pathogenic fungi can include yeast-like fungi, filamentous fungi, and the like. Yeast-like fungi can include Cryptococcus fungi, Candida fungi, and the like. Filamentous fungi can include Aspergillus fungi, and the like.

Pathogenic protozoa of protozoan infections are not limited in particular. The pathogenic protozoa can include malaria parasite, kala-azar parasite, and the like.

Pathogenic protozoa of parasitic infections can include lumbricus, nematode, hookworm, and the like.

Preferable examples of the infectious diseases include bacterial infections, viral infections, protozoan infections, and parasitic infections. More preferable examples are bacterial infections. Pathologies of infectious diseases can include pneumonia, sepsis, meningitis, and urinary tract infection.

Allergic diseases can include allergic diseases that belong to type I, type II, type III, type IV, or type V. Allergic diseases belonging to type I can include pollinosis, anaphylactic shock, allergic rhinitis, conjunctivitis, bronchial asthma, urticarial, atopic dermatitis, and the like. Allergic diseases belonging to type II can include immune incompatibile blood transfusion, autoimmune hemolytic anemia, autoimmune thrombocytopenia, autoimmune granulocytopenia, Hashimoto's disease, Goodpasture syndrome, and the like. Allergic diseases belonging to type III can include immune complex nephritis, Arthus reaction, serum sickness, and the like. Allergic diseases belonging to type IV can include tuberculosis, contact dermatitis, and the like. Allergic diseases belonging to type V can include Basedow's disease, and the like. Allergic diseases are preferably those of type I, type II, type III, and type IV, more preferably those of type I, type II, type III, and further preferably that of type I. Allergic diseases belonging to type II, type III, and type V overlap some of autoimmune diseases described later.

Autoimmune diseases can include systemic lupus erythematosus, rheumatoid arthritis, multiple sclerosis, Sjogren's syndrome, scleroderma, dermatomyositis, primary biliary cirrhosis, primary sclerosing cholangitis, ulcerative colitis, Crohn's disease, psoriasis, vitiligo, bullous pemphigoid, alopecia areata, sudden dilated cardiomyopathy, type 1 diabetes mellitus, Basedow's disease, Hashimoto's disease, myasthenia gravis, IgA nephropathy, membranous nephropathy, megaloblastic anemia, and the like. The autoimmune diseases are preferably systemic lupus erythematosus, rheumatoid arthritis, multiple sclerosis, Sjogren's syndrome, scleroderma, and dermatomyositis. The autoimmune diseases are preferably autoimmune diseases in which antinuclear antibody is detected.

Traumatic injuries can include bone fracture, burn, and the like.

The specimen may be any specimen that can be collected from a subject. Preferably, the specimen is blood, bone marrow, urine, and body fluid. Examples of blood include peripheral blood, venous blood, and arterial blood. Preferably, blood is peripheral blood. Examples of blood include peripheral blood collected by using an anticoagulant agent such as ethylenediaminetetraacetate (sodium salt or potassium salt), heparin sodium, or the like. The body fluid means fluids other than blood and urine. Examples of the body fluid include ascites, pleural fluid, and spinal fluid.

The specimen may be selected in accordance with the disease to be analyzed. Cells in blood, particularly in the above-described diseases, often have features that are different from those of normal cells, in the numerical distribution of the types of cells and/or the types of abnormal findings, which are described later. Therefore, with respect to various diseases, analysis can be performed by using blood specimens. Bone marrow allows analysis of diseases of the hematopoietic organ system, in particular. Cells contained in ascites, pleural fluid, spinal fluid, and the like are effective for diagnosis of tumors of tissues other than the hematopoietic organ system, diseases of the hematopoietic organ system, infectious diseases, and the like, in particular. Urine allows analysis of tumors of tissues other than the hematopoietic organ system, infectious diseases, and the like, in particular.

The analysis target cell may be any cell that is contained in a specimen. The analysis target cell means a cell that is used in order to analyze a disease. The analysis target cell can include a plurality of cells. Here, the "plurality" can include a case where the number of one type of cell is a plural number and a case where the number of cell types is a plural number. The specimen in a normal state can include a plurality of types of cells that are morphologically classified through histological microscopic observation or cytological microscopic observation. The morphological classification of a cell (also referred to as "cell morphology classification") includes classification of the type of the cell and classification of the type of abnormal finding in the cell. Preferably, the analysis target cell is a group of cells that belong to a predetermined cell lineage. The predetermined cell lineage is a cell group that belongs to the same lineage differentiated from one type of tissue stem cell. Preferably, the predetermined cell lineage is cells of the hematopoietic system, and more preferably, cells in blood (also referred to as "blood cells").

In a conventional method, a person observes, in a microscopic bright field, a preparation having been subjected to bright field staining, whereby hematopoietic cells are morphologically classified. Preferably, the staining is selected from Wright's staining, Giemsa staining, Wright-Giemsa staining, and May-Giemsa staining. More preferably, the staining is May-Giemsa staining. The preparation may be any preparation that allows individual observation of the morphology of each cell belonging to a predetermined cell group. Examples of the preparation include a smear preparation and an impression preparation. Preferably, the preparation is a smear preparation using peripheral blood or bone marrow as a specimen, and more preferably, is a smear preparation of peripheral blood.

In morphological classification, the type of blood cell includes: neutrophil including segmented neutrophil and band neutrophil; metamyelocyte; myelocyte; promyelocyte; blast; lymphocyte; plasma cell; atypical lymphocyte; monocyte; eosinophil; basophil; erythroblast (which is nucleated erythrocyte and includes proerythroblast, basophilic erythroblast, polychromatic erythroblast, orthochromatic erythroblast, promegaloblast, basophilic megaloblast, polychromatic megaloblast, and orthochromatic megaloblast); platelet; platelet aggregate; megakaryocyte (which is nucleated megakaryocyte and includes micromegakaryocyte); and the like.

The predetermined cell group may include abnormal cells that exhibit morphologically abnormal findings, in addition to normal cells. An abnormality appears as a morphologically classified cell feature. Examples of abnormal cells are cells that emerge when a person has a predetermined disease, and are tumor cells and the like. In the case of the hematopoietic system, the predetermined disease is a disease selected from the group consisting of: myelodysplastic syndrome; leukemia (including acute myeloblastic leukemia, acute myeloblastic leukemia, acute promyelocytic leukemia, acute myelomonocytic leukemia (involving neutrophil differentiation), acute monocytic leukemia, erythroleukemia, acute megakaryoblastic leukemia, acute myeloid leukemia, acute lymphoblastic leukemia, lymphoblastic leukemia, chronic myelogenous leukemia, chronic lymphocytic leukemia, and the like); malignant lymphoma (Hodgkin's lymphoma, non-Hodgkin's lymphoma, and the like); and multiple myeloma. In the case of the hematopoietic system, the abnormal finding corresponds to a cell that has at least one type of morphological feature selected from the group consisting of: nucleus morphology abnormality; presence of vacuole; granule morphology abnormality; granule distribution abnormality; presence of abnormal granule; cell size abnormality; presence of inclusion body; and bare nucleus.

Examples of the nucleus morphology abnormality include: nucleus becoming small; nucleus becoming large; nucleus becoming hypersegmented; nucleus that should be segmented in a normal state but has not been segmented (including pseudo-Pelger anomaly and the like); presence of vacuole; swelled nucleolus; cleaved nucleus; a single cell that should have one nucleus but has an abnormality of having two; and the like.

Examples of abnormality in the morphology of an entire cell include presence of vacuole in cytoplasm (also referred to as vacuolar degeneration); presence of morphological abnormality in granule such as megathrombocyte, azurophil granule, neturophil granule, eosinophil granule, and basophil granule; presence of abnormality in distribution (excess, decrease, or disappearance) of the above-mentioned granules; presence of abnormal granule (for example, toxic granule); cell size abnormality (larger or smaller than normal cell); presence of inclusion body (Döhle body, Auer rod, and the like); and bare nucleus.

Preferably, the abnormal finding is at least one type selected from the group consisting of: nucleus morphology abnormality; granulation abnormality; cell size abnormality; cell malformation; cytoclasis; vacuole; immature cell; presence of inclusion body; Döhle body; satellitism; nucleoreticulum abnormality; petal-like nucleus; increased N/C ratio; and bleb-like, smudge, and hairy cell-like morphologies.

Preferably, the nucleus morphology abnormality includes at least one type selected from hypersegmentation, hyposegmentation, pseudo-Pelger anomaly, ring-shaped nucleus, spherical nucleus, elliptical nucleus, apoptosis, polynuclearity, karyorrhexis, enucleation, bare nucleus, irregular nuclear contour, nuclear fragmentation, internuclear bridging, multiple nuclei, cleaved nucleus, nuclear division, and nucleolus abnormality. The granulation abnormality includes at least one type selected from degranulation, granule distribution abnormality, toxic granule, Auer rod, Fagott cell, and pseudo Chediak-Higashi granule-like granule. Granulation abnormality in eosinophils and basophils includes a phenomenon of biased distribution of granules in a cell as abnormal granules, for example. The cell size abnormality includes megathrombocyte.

Preferably, the type of cell includes at least one type selected from neutrophil, eosinophil, platelet, lymphocyte, monocyte, and basophil.

More preferably, the type of cell further includes at least one type selected from metamyelocyte, myelocyte, promyelocyte, blast, plasma cell, atypical lymphocyte, immature eosinophil, immature basophil, erythroblast, and megakaryocyte.

More preferably, the hematopoietic system disease is aplastic anemia or myelodysplastic syndrome, and when the type of cell is neutrophil, the abnormal finding is at least one type selected from granulation abnormality and hypersegmentation, or when the type of cell is eosinophil, the abnormal finding is abnormal granule. The abnormal finding in a cell includes megathrombocyte. By evaluating these findings, it is possible to discern between aplastic anemia and myelodysplastic syndrome.

<Outline of Support Method>

In the support method, the manners of discerning an abnormal finding and/or discerning the type of cell are not limited in particular, as long as discerning an abnormal finding on the basis of an image and/or discerning the type of cell can be realized. The discerning may be performed by an examiner or may be performed by using a discriminator described below.

The outline of the support method using a discriminator is described with reference to FIG. 1. The discriminator used in the support method includes a computer algorithm. Preferably, the computer algorithm includes a first computer algorithm and a second computer algorithm. More preferably, the first computer algorithm includes a plurality of deep learning algorithms having a neural network structure. The second computer algorithm includes a machine learning algorithm. Preferably, the deep learning algorithms include a first neural network 50 for extracting a feature quantity quantitatively representing a morphological feature of a cell, a second neural network 51 for discerning the type of abnormal finding in the cell, and/or a second neural network 52 for discerning the type of the cell. The first neural network 50 extracts a feature quantity of the cell. The second neural network 51, 52 is at the downstream of the first neural network, and discerns an abnormal finding in the cell or the type of the cell on the basis of the feature quantity extracted by the first neural network 50. More preferably, the second neural network 51, 52 may include a neural network trained for discerning the type of cell, and a plurality of types of neural networks that have been trained for respective abnormal findings in cells and that correspond to respective abnormal findings. For example, in FIG. 1, a 1st deep learning algorithm is a deep learning algorithm for discerning a first abnormal finding (for example, granulation abnormality), and includes the first neural network 50 and the second neural network 51 trained for discerning the first abnormal finding. A 1st' deep learning algorithm is a deep learning algorithm for detecting a second abnormal finding (for example, hypersegmentation), and includes the first neural network 50 and the second neural network 51 trained for discerning the second abnormal finding. A 2nd deep learning algorithm is a deep learning algorithm for discerning the type of cell, and includes the first neural network 50 and the second neural network 52 trained for discerning the type of cell.

The machine learning algorithm analyzes, for each specimen, a disease of a subject from whom the specimen has been collected, on the basis of a feature quantity outputted from the deep learning algorithm, and outputs, as an analysis result, a disease name or a label indicating the disease name.

Next, deep learning training data 75, a method for generating machine learning training data, and a method for analyzing a disease are described with reference to the examples shown in FIG. 2 to FIG. 4. In the following, for convenience, description is made using the first neural network, the second neural network, and a gradient boosting tree which is a machine learning algorithm.

<Generation of Deep Learning Training Data>

A training image 70 that is used for training a deep learning algorithm is an image obtained by capturing an analysis target cell contained in a specimen collected from a subject to whom a disease name has already been given. A plurality of the training images 70 are captured for one specimen. The analysis target cell included in each image is associated with the type of cell based on morphological classification and a result of an abnormal finding discerned by an examiner. Preferably, a preparation for capturing the training image 70 is created from a specimen containing the same type of cell as the analysis target cell, by a preparation creating method and a staining method similar to those employed for a preparation that includes the analysis target cell. Preferably, the training image 70 is captured in the same condition as that used for capturing the analysis target cell.

The training image 70 can be obtained in advance for each cell by using, for example, a known light microscope or an imaging apparatus such as a virtual slide scanner. In the example shown in FIG. 2, the training image 70 is generated by reducing a raw image captured in 360 pixels×365 pixels by a blood cell differential automatic analyzer DI-60 (manufactured by Sysmex Corporation) into 255 pixels×255 pixels. However, this reduction is not mandatory. The number of pixels of the training image 70 is not limited in particular as long as analysis can be performed, but the number of pixels of one side of the image is preferably greater than 100. In the example shown in FIG. 2, erythrocytes are present around a neutrophil, but the image may be trimmed such that only the target cell is included in the image. If, at least, one cell, for which training is to be performed (erythrocytes, and platelets of normal sizes may be included), is included in one image and the pixels corresponding to the cell, for which training is to be performed, exist by about ⅑ of the total pixels of the image, the image can be used as the training image 70.

For example, preferably, image capturing by the imaging apparatus is performed in RGB colors, CMY colors, or the like. Preferably, as for a color image, the darkness/paleness or brightness of each of primary colors, such as red, green, and blue, or cyan, magenta, and yellow, is expressed by a 24 bit value (8 bits×3 colors). It is sufficient that the training image 70 includes at least one hue, and the darkness/paleness or brightness of the hue, but more preferably, includes at least two hues and the darkness/paleness or brightness of each hue. Information including hue and the darkness/paleness or brightness of the hue is also called tone.

Next, information of tone of each pixel is converted from, for example, RGB colors into a format that includes information of brightness and information of hue. Examples of the format that includes information of brightness and information of hue include YUV (YCbCr, YPbPr, YIQ, and the like). Here, an example of converting to a YCbCr format is described. Since the training image is in RGB colors, conversion into brightness 72Y, first hue (for example, bluish color) 72Cb, and second hue (for example, reddish color) 72Cr is performed. Conversion from RGB to YCbCr can be performed by a known method. For example, conversion from RGB to YCbCr can be performed according to International Standard ITU-R BT.601. The brightness 72Y, the first hue 72Cb, and the second hue 72Cr after the conversion can be each expressed as a matrix of gradation values as shown in FIG. 2 (hereinafter, also referred to as tone matrices 72$y$, 72$cb$, 72$cr$). The brightness 72Y, the first hue 72Cb, and the second hue 72Cr are each expressed in 256 gradations consisting of 0 to 255 gradations. Here, instead of the brightness 72Y, the first hue 72Cb, and the second hue 72Cr, the training image may be converted into the three primary colors of red R, green G, and blue B, or the three primary colors of pigment of cyan C, magenta M, and yellow Y.

Next, on the basis of the tone matrices 72$y$, 72$cb$, 72$cr$, for each pixel, tone vector data 74 is generated by combining three gradation values of the brightness 72$y$, the first hue 72$cb$, and the second hue 72$cr$.

Figure 2:
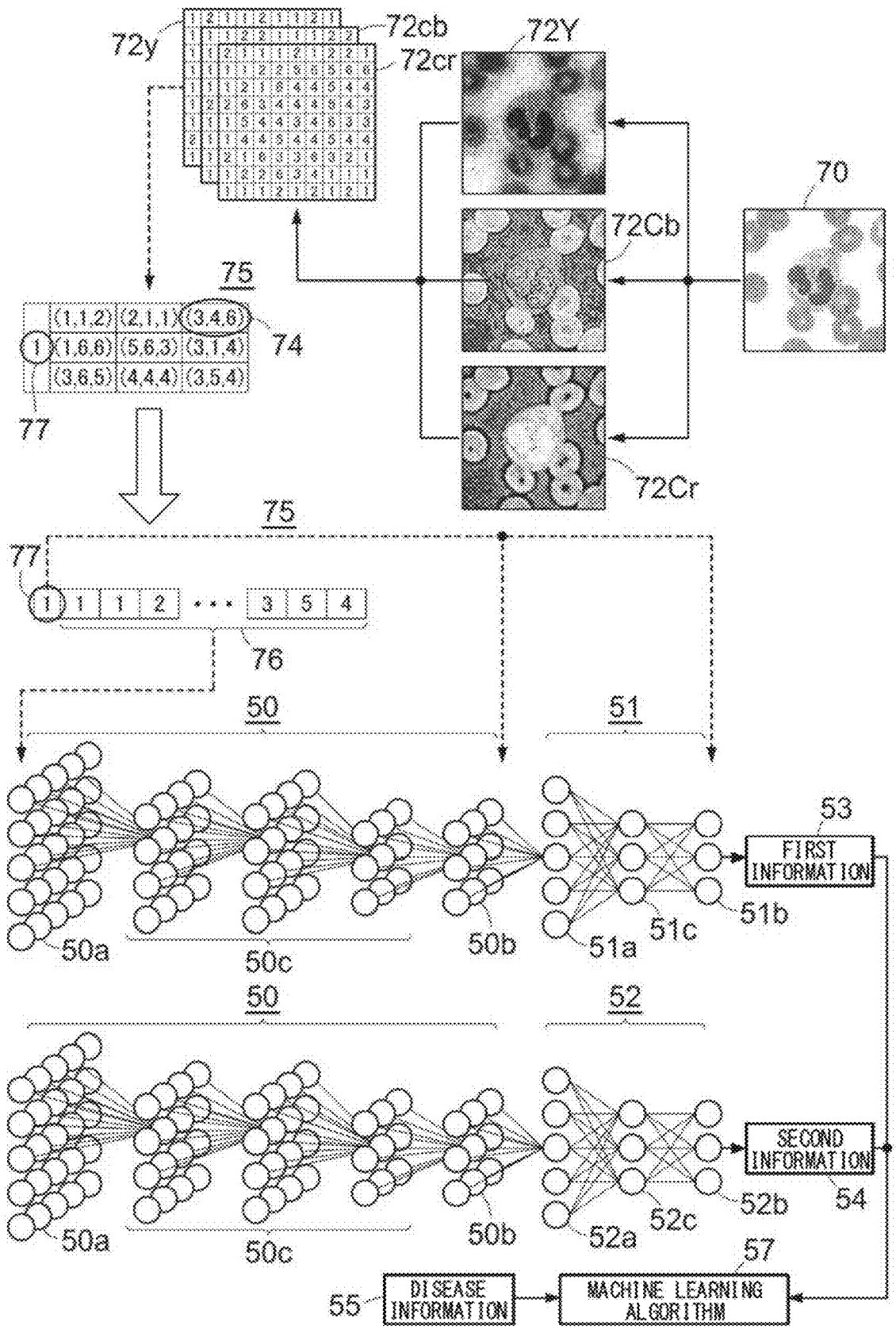
FIG. 2 is a schematic diagram showing an example of a generation procedure of deep learning training data and a training procedure of a 1st deep learning algorithm, a 2nd deep learning algorithm, and a machine learning algorithm.

Next, for example, since the training image 70 in FIG. 2 is of a segmented neutrophil, each tone vector data 74 generated from the training image 70 in FIG. 2 is provided with "1" as a label value 77 which indicates that the image is of a segmented neutrophil, whereby the deep learning training data 75 is obtained. In FIG. 2, for convenience, the deep learning training data 75 is expressed by 3 pixels×3 pixels. However, in actuality, the tone vector data exists by the number of pixels that have been obtained at the capture of the training image 70.

FIGS. 3A and 3B show an example of the label value 77. As the label value, a label value 77 that is different according to the type of cell and the presence or absence of an abnormal finding in each cell is provided.

<Outline of Generation of Discriminator>

Using FIG. 2 as an example, the outline of a method for generating a discriminator is described. The generation of a discriminator can include training of the deep learning algorithm and training of the machine learning algorithm.

Training of Deep Learning Algorithm

The 1st deep learning algorithm includes the first neural network 50 and the second neural network 51 in order to generate first information 53, which is information regarding the type of abnormal finding. The 2nd deep learning algorithm includes the first neural network 50 and the second neural network 52 in order to generate second information 54, which is information regarding the type of cell.

The number of nodes at an input layer 50$a$ in the first neural network 50 corresponds to the product of the number of pixels of the deep learning training data 75 that is inputted, and the number of brightness and hue (for example, in the above example, three, i.e., the brightness 72$y$, the first hue 72$cb$, and the second hue 72$cr$) included in the image. The tone vector data 74 is inputted, as a set 76 thereof, to the input layer 50$a$ of the first neural network 50. The label value 77 of each pixel of the deep learning training data 75 is inputted to an output layer 50$b$ of the first neural network, to train the first neural network 50.

On the basis of the deep learning training data 75, the first neural network 50 extracts a feature quantity with respect to a cell feature reflecting the morphological cell type or abnormal finding described above. The output layer 50$b$ of the first neural network outputs a result reflecting these feature quantities. Each result outputted from a softmax function of the output layer 50b of the first neural network 50 is inputted to an input layer 51a of the second neural network 51 and an input layer 52a of the second neural network 52. Since cells that belong to a predetermined cell lineage have similar cell morphologies, the second neural networks 51, 52 are trained so as to be further specialized in discernment of cell features that reflect a morphologically specific type of cell and a morphologically specific abnormal finding. Thus, the label value 77 of the deep learning training data 75 is also inputted to output layers 51b, 52b of the second neural network. Reference characters 50c, 51c, and 52c in FIG. 2 represent middle layers. For one abnormal finding, one second neural network 51 can be trained. In other words, second neural networks 51 corresponding to the number of types of abnormal findings that should be analyzed can be trained. The number of types of the second neural network 52 for discerning the type of cell is one.

Preferably, the first neural network 50 is a convolution connect neural network, and the second neural networks 51, 52 are each a full connect neural network.

Figure 5:
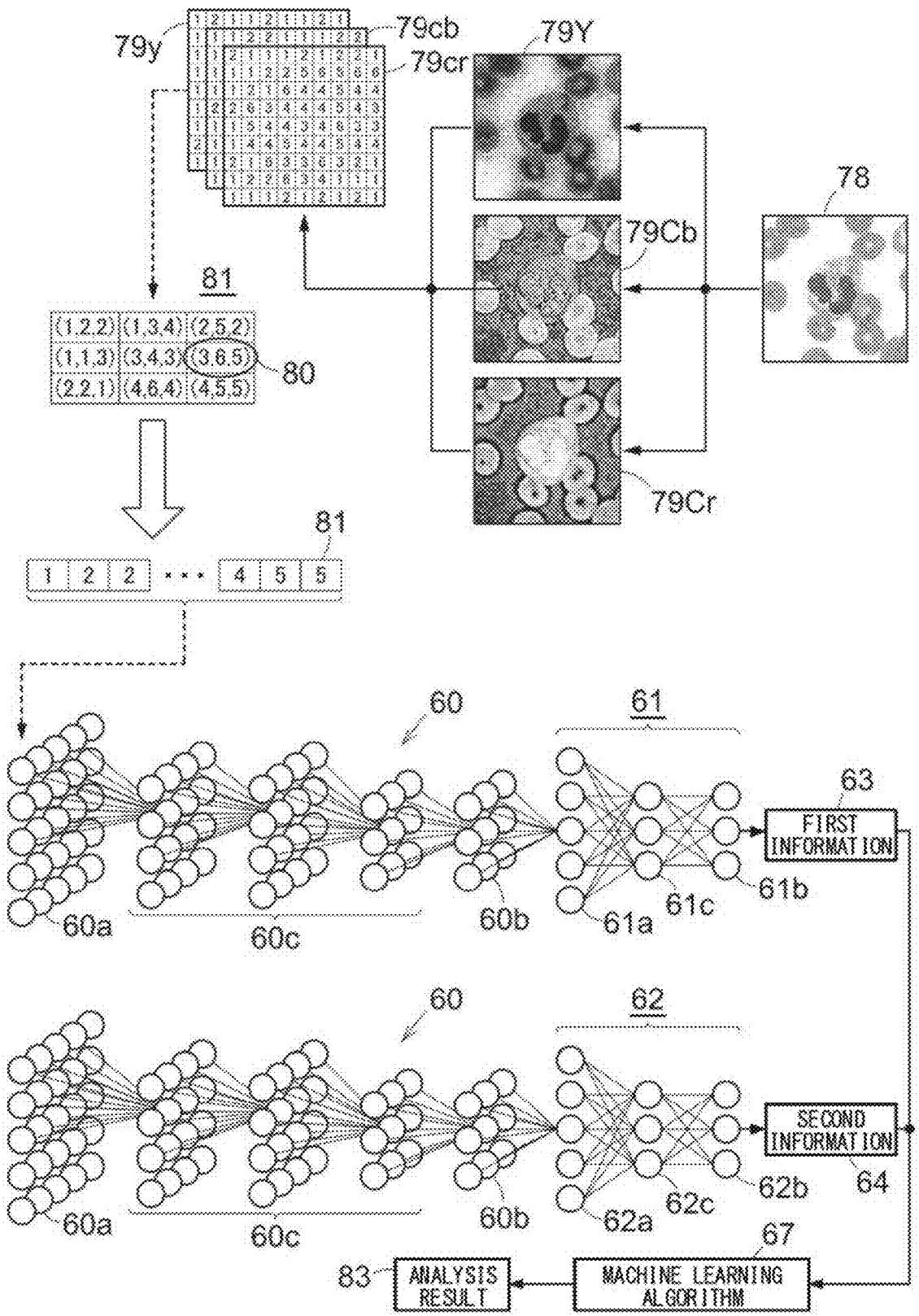
FIG. 5 is a schematic diagram showing an example of a generation procedure of analysis data and a procedure of disease analysis using a computer algorithm.

Accordingly, the 1st deep learning algorithm having the trained first neural network 60 and second neural network 61, and the 2nd deep learning algorithm having the trained first neural network 60 and second neural network 62 are generated (see FIG. 5).

For example, the second neural network 61 for discerning an abnormal finding outputs a probability of the presence or absence of an abnormal finding, as a discernment result of an abnormal finding. The probability may be given in terms of the name of an abnormal finding or a label value corresponding to the abnormal finding. The second neural network 62 for discerning the type of cell outputs, as a discernment result, a probability that each analysis target cell belongs to each of a plurality of types of cells inputted as the training data. The probability may be given in terms of the name of the type of cell or a label value corresponding to the type of cell.

Training of Machine Learning Algorithm

Machine learning training data 90 shown in FIG. 4 is used as training data for training a machine learning algorithm 57. The machine learning training data 90 includes a feature quantity and disease information 55. For each specimen, the abnormal finding and/or the probability (which have been outputted from the deep learning algorithm) of the type of cell or a value obtained by converting the probability into a cell number can be used as the feature quantity to be learned. In the machine learning training data 90, the feature quantity is associated with disease information expressed as the name of a disease of the subject from whom the corresponding specimen has been collected, a label value of the disease, or the like.

The feature quantity to be inputted to the machine learning algorithm 57 is at least one of information regarding the type of abnormal finding and information regarding the type of cell. As the feature quantity, information regarding the type of abnormal finding and information regarding the type of cell are preferably used. The abnormal finding to be used as the feature quantity may be of one type or a plurality of types. The type of cell to be used as the feature quantity may be of one type or a plurality of types.

The training image 70 captured from each specimen and used for training the deep learning algorithm is analyzed by using the trained 1st deep learning algorithm and/or 2nd deep learning algorithm, and the abnormal finding and/or the type of cell is discerned for the cell in each training image 70. For each cell, a probability of having each abnormal finding and a label value indicating the abnormal finding is outputted from the second neural network 61. The probability of having each abnormal finding and the label value indicating the abnormal finding serve as a discernment result of the type of abnormal finding. A probability corresponding to each type of cell and a label value indicating the type of cell are outputted from the second neural network 62. The probability corresponding to each type of cell and the label value indicating the type of cell serve as a discernment result of the type of cell. On the basis of these pieces of information, the feature quantity to be inputted to the machine learning algorithm 57 is generated.

FIG. 4 shows an example of the machine learning training data 90. For convenience of description, FIG. 4 shows an example in which the cell number is three (cell No. 1 to No. 3); the abnormal finding includes five findings, which are degranulation, Auer rod, spherical nucleus, hypersegmentation, and megathrombocyte; and the type of cell includes eight types, which are segmented neutrophil, band neutrophil, lymphocyte, monocyte, eosinophil, basophil, blast, and platelet. A to F provided above the table in FIG. 4 represent column numbers of the table. 1 to 19 provided at the left of the table represent row numbers.

For each specimen, with respect to each analysis target cell, the first neural network 50 and the second neural network 51 calculate the probability of having each abnormal finding, and the second neural network 51 outputs the calculated probability. In FIG. 4, the probability of having an abnormal finding is expressed by the numbers from 0 to 1. For example, in the case of having an abnormal finding, the probability can be expressed by a value close to "1", and in the case of not having an abnormal finding, the probability can be expressed by a number close to "0". In FIG. 4, the values in the cells of rows 1 to 5 in columns A to E are values outputted by the second neural network 51. Next, for each specimen, the sum of the probabilities for each analyzed type of abnormal finding is calculated. In FIG. 4, the values in the cells of rows 1 to 5 in column F are the sums of the respective abnormal findings. For each specimen, the group of data in each of which a label indicating the name of an abnormal finding is associated with the sum per specimen of the probability of having the abnormal finding is referred to as "information regarding the type of abnormal finding". In FIG. 2, the information regarding the type of abnormal finding is the first information 53. In FIG. 4, the group of data in which cell B1 is associated with cell F1, cell B2 is associated with cell F2, cell B3 is associated with cell F3, cell B4 is associated with cell F4, and cell B5 is associated with cell F5 is the "information regarding the type of abnormal finding", which serves as the first information 53. The first information 53 is associated with the disease information 55 expressed as a disease name or a label value indicating the disease name, to serve as the machine learning training data 90. In FIG. 4, row 19 indicates the disease information 55.

As shown in FIG. 4, with respect to one type of abnormal finding, a probability less than "1" is indicated in some cases. In such a case, for example, a predetermined cut off value is determined, and all types of abnormal findings indicating values lower than the cut off value may be regarded as having a probability of "0". Alternatively, a predetermined cut off value is determined, and all types of abnormal findings indicating values higher than the cut off value may be regarded as having a probability of "1".

Here, the probability for each type of abnormal finding may be expressed as a cell number for each type of abnormal finding.

Also with respect to the type of cell, for each analysis target cell, the first neural network 50 and the second neural network 52 calculate a probability corresponding to each type of cell, and the second neural network 52 outputs the calculated probability. The probability corresponding to each type of cell is calculated for all the types of cells which are the analysis targets of the first neural network 50 and the second neural network 52. In the example shown in FIG. 4, for one analysis target cell, with respect to all the items of segmented neutrophil, band neutrophil, lymphocyte, monocyte, eosinophil, basophil, blast, and platelet, a probability corresponding to each type of cell is calculated. The values in the cells of rows 6 to 13 in columns A to E are values outputted by the second neural network 52. Next, for each specimen, the sum of the probabilities for each analyzed type of cell is calculated. In FIG. 4, the values in the cells of rows 6 to 13 in column F are the sums of the respective types of cells. The group of data in each of which a label indicating the name of the cell type is associated with the sum per specimen of the probability corresponding to the cell type is referred to as "information regarding the type of cell". The information regarding the type of cell is the second information 54 in FIG. 2. In FIG. 4, the group of data in which cell B6 is associated with cell F6, cell B7 is associated with cell F7, cell B8 is associated with cell F8, cell B9 is associated with cell F9, cell B10 is associated with cell F10, cell B11 is associated with cell F11, cell B12 is associated with cell F12, and cell B13 is associated with cell F13 is "information regarding the type of cell", which serves as the second information 54. The second information 54 is associated with the disease information 55 expressed as a disease name or a label value indicating the disease name, to serve as the machine learning training data 90. In FIG. 4, row 19 indicates the disease information 55.

Here, the probability for each type of cell may be expressed as a cell number for each type of cell. As shown in FIG. 4, with respect to one analysis target cell, a probability higher than 0 is indicated for a plurality of items of type of cell in some cases. In such a case, for example, a predetermined cut off value is determined, and all types of cells indicating values lower than the cut off value may be regarded as having a probability of "0". Alternatively, a predetermined cut off value is determined, and all types of cells indicating values higher than the cut off value may be regarded as having a probability of "1".

Further, a preferable feature quantity is information regarding the type of abnormal finding obtained for each type of cell. With reference to FIG. 4, for example, as shown in row 14 to row 18 which indicate degranulation of neutrophil (cell B14), Auer rod of blast (cell B15), spherical nucleus of neutrophil (cell B16), hypersegmentation of neutrophil (cell B17), and megathrombocyte (cell B18), when generating the deep learning training data 75, a specific type of cell and a specific type of abnormal finding are associated to each other, and training is performed. The feature quantity is generated in the same manner as that for the type of abnormal finding not associated with the type of cell. The information regarding the type of abnormal finding obtained for each type of cell is referred to as third information. The third information is associated with the disease information 55 expressed as a disease name or a label value indicating the disease name, to serve as the machine learning training data 90.

The machine learning training data 90 is inputted to the machine learning algorithm 57, to train the machine learning algorithm 57, whereby a trained machine learning algorithm 67 (see FIG. 5) is generated.

Preferably, a training method for the machine learning algorithm 57 uses at least one of the machine learning training data 90 in which the first information is associated with the disease information 55; the machine learning training data 90 in which the second information is associated with the disease information 55; and the machine learning training data 90 in which the third information is associated with the disease information 55. More preferably, the training method uses the machine learning training data 90 in which the first information is associated with the disease information 55 and the machine learning training data 90 in which the second information is associated with the disease information 55, or uses the machine learning training data 90 in which the third information is associated with the disease information 55 and the machine learning training data 90 in which the second information is associated with the disease information 55. Most preferably, in the training method, both of the machine learning training data 90 in which the second information 54 is associated with the disease information 55 expressed as a disease name or a label value indicating the disease name, and the machine learning training data 90 in which the third information is associated with the disease information 55 expressed as a disease name or a label value indicating the disease name are inputted as training data to the machine learning algorithm 57. In this case, the types of cells in the second information 54 and the types of cells associated with the third information may be the same or different with each other.

The machine learning algorithm may be any machine learning algorithm that can analyze a disease on the basis of the feature quantity described above. For example, the machine learning algorithm can be selected from regression, tree, neural network, Bayes, time series model, clustering, and ensemble learning.

The regression can include linear regression, logistic regression, support vector machine, and the like. The tree can include gradient boosting tree, decision tree, regression tree, random forest, and the like. The neural network can include perceptron, convolution neural network, recurrent neural network, residual network, and the like. The time series model can include moving average, auto regression, autoregressive moving average, autoregressive integrated moving average, and the like. The clustering can include k-nearest-neighbor. The ensemble learning can include boosting, bagging, and the like. Gradient boosting tree is preferable.

<Support Method for Disease Analysis>

FIG. 5 shows an example of the support method for disease analysis. In the support method, analysis data 81 is generated from an analysis image 78 obtained by capturing an analysis target cell. The analysis image 78 is an image obtained by capturing an analysis target cell contained in a specimen collected from a subject. The analysis image 78 can be obtained by using, for example, a known light microscope or a known imaging apparatus such as a virtual slide scanner. In the example shown in FIG. 5, similar to the training image 70, the analysis image 78 is generated by reducing a raw image captured in 360 pixels×365 pixels by a blood cell differential automatic analyzer DI-60 (manufactured by Sysmex Corporation) into 255 pixels×255 pixels. However, this reduction is not mandatory. The number of pixels of the analysis image 78 is not limited in particular as long as analysis can be performed, but the number of pixels of one side of the image is preferably greater than 100. In the example shown in FIG. 5, erythrocytes are present around a segmented neutrophil, but the image may be trimmed such that only the target cell is included in the image. If, at least, one cell to be analyzed (erythrocytes, and platelets of normal sizes may be included) is included in one image, and the pixels corresponding to the cell to be analyzed exist by about ⅑ of the total pixels of the image, the image can be used as the analysis image 78.

For example, preferably, image capturing by the imaging apparatus is performed in RGB colors, CMY colors, or the like. Preferably, as for a color image, the darkness/paleness or brightness of each of primary colors, such as red, green, and blue, or cyan, magenta, or yellow, is expressed by a 24 bit value (8 bits×3 colors). It is sufficient that the analysis image 78 includes at least one hue, and the darkness/paleness or brightness of the hue, but more preferably, includes at least two hues and the darkness/paleness or brightness of each hue. Information including hue and the darkness/paleness or brightness of the hue is also called tone.

For example, the format of RGB colors is converted into a format that includes information of brightness and information of hue. Examples of the format that includes information of brightness and information of hue include YUV (YCbCr, YPbPr, YIQ, and the like). Here, an example of converting to a YCbCr format is described. Since the analysis image is in RGB colors, conversion into brightness 79Y, first hue (for example, bluish color) 79Cb, and second hue (for example, reddish color) 79Cr is performed. Conversion from RGB to YCbCr can be performed by a known method. For example, conversion from RGB to YCbCr can be performed according to International Standard ITU-R BT.601. The brightness 79Y, the first hue 79Cb, and the second hue 79Cr after the conversion can be each expressed as a matrix of gradation values as shown in FIG. 5 (hereinafter, also referred to as tone matrices 79*y*, 79*cb*, 79*cr*). The brightness 79Y, the first hue 79Cb, and the second hue 79Cr are each expressed in 256 gradations consisting of 0 to 255 gradations. Here, instead of the brightness 79Y, the first hue 79Cb, and the second hue 79Cr, the analysis image may be converted into the three primary colors of red R, green G, and blue B, or the three primary colors of pigment of cyan C, magenta M, and yellow Y.

Next, on the basis of the tone matrices 79*y*, 79*cb*, 79*cr*, for each pixel, tone vector data 80 is generated by combining three gradation values of the brightness 79*y*, the first hue 79*cb*, and the second hue 79*cr*. A set of the tone vector data 80 generated from one analysis image 78 is generated as the analysis data 81.

Preferably, the generation of the analysis data 81 and the generation of the deep learning training data 75 are performed at least in the same capture condition and the same generation condition of the vector data that is inputted from each image to a neural network.

The 1st deep learning algorithm includes the first neural network 60 and the second neural network 61 in order to generate first information 63 which is information regarding the type of abnormal finding. The 2nd deep learning algorithm includes the first neural network 60 and the second neural network 62 in order to generate second information 64, which is information regarding the type of cell.

The analysis data 81 is inputted to an input layer 60*a* of the trained first neural network 60. The first neural network 60 extracts a feature quantity of the cell from the analysis data 81, and outputs the result from an output layer 60*b* of the first neural network 60. Each result outputted from a softmax function of the output layer 60*b* of the first neural network 60 is inputted to an input layer 61*a* of the second neural network 61 and an input layer 62*a* of the second neural network 62.

Next, the result outputted from the output layer 60*b* is inputted to the input layer 61*a* of the trained second neural network 61. For example, on the basis of the inputted feature quantity, the second neural network 61 for discerning an abnormal finding outputs, from an output layer 61*b*, a probability of the presence or absence of an abnormal finding, as a discernment result of an abnormal finding.

Meanwhile, the result outputted from the output layer 60*b* is inputted to the input layer 62*a* of the trained second neural network 62. On the basis of the inputted feature quantity, the second neural network 62 outputs, from an output layer 62*b*, a probability that the analysis target cell included in the analysis image belongs to each of the types of cells inputted as the training data. In FIG. 5, reference characters 60*c*, 61*c*, 62*c* represent middle layers.

Next, on the discernment result of the abnormal finding, for each specimen, information regarding the type of abnormal finding (the first information 63 in FIG. 5) corresponding to the specimen is obtained. For example, the first information 63 is the sum of the probabilities for each analyzed type of abnormal finding outputted from the output layer 61*b* of the second neural network 61. The generation method for the first information 63 is the same as the generation method for the machine learning training data.

Meanwhile, on the basis of the discernment result of the type of cell, for each specimen, information regarding the type of cell (the second information 64 in FIG. 5) corresponding to the specimen is obtained. For example, the second information 64 is the sum of the probabilities for each analyzed type of cell outputted from the output layer 62*b* of the second neural network 62. The generation method for the second information 64 is the same as the generation method for the machine learning training data 90.

When the generated first information 63 and second information 64 are inputted to the trained machine learning algorithm 67, an analysis result 83 is generated by the machine learning algorithm 67. The analysis result 83 can be a disease name or a label value indicating the disease name.

Preferably, as the data inputted to the machine learning algorithm 67, at least one of the first information 63, the second information 64, and the third information can be used. More preferably, the first information 63 and the second information 64 can be used, or the third information and the second information 64 can be used. Most preferably, both of the second information 64 and the third information are used as the analysis data 81. In this case, the types of cells in the second information 64 and the types of cells associated with the third information may be the same or different with each other. The third information is information that is generated by associating a specific type of cell with a specific type of abnormal finding when generating the analysis data 81, and the generation method therefor is the same as the method described in the generation method for the machine learning training data 90.

[Disease Analysis Support System 1]

<Configuration of Disease Analysis Support System 1>

Figure 6:
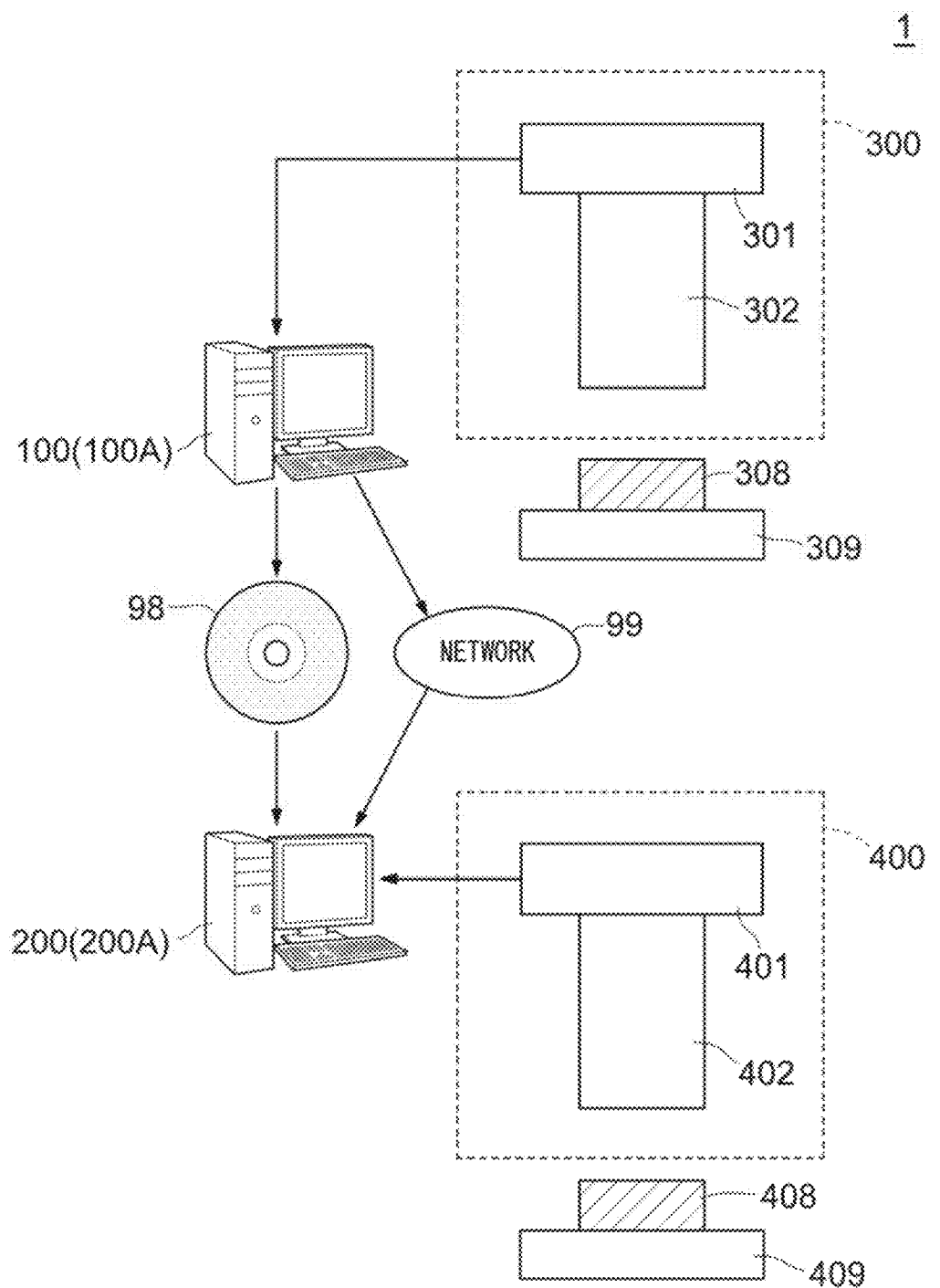
FIG. 6 shows a schematic configuration example of a disease analysis system 1.

A disease analysis support system 1 is described. With reference to FIG. 6, the disease analysis support system 1 includes a training apparatus 100A and a disease analyzer 200A. A vendor-side apparatus 100 operates as the training apparatus 100A, and a user-side apparatus 200 operates as the disease analyzer 200A. The training apparatus 100A generates a discriminator by using the deep learning training data 75 and the machine learning training data 90, and provides the discriminator to a user. The discriminator is provided from the training apparatus 100A to the disease analyzer 200A through a storage medium 98 or a network 99. The disease analyzer 200A performs analysis of an image of an analysis target cell, using the discriminator provided from the training apparatus 100A.

The training apparatus 100A is implemented as a general purpose computer, for example, and performs a deep learning process on the basis of a flow chart described later. The disease analyzer 200A is implemented as a general purpose computer, for example, and performs a disease analysis process on the basis of a flow chart described later. The storage medium 98 is a computer-readable non-transitory tangible storage medium such as a DVD-ROM or a USB memory, for example.

The training apparatus 100A is connected to an imaging apparatus 300. The imaging apparatus 300 includes an image pickup device 301 and a fluorescence microscope 302, and captures a bright field image of a learning preparation 308 set on a stage 309. The training preparation 308 has been subjected to the staining described above. The training apparatus 100A obtains the training image 70 captured by the imaging apparatus 300.

The disease analyzer 200A is connected to an imaging apparatus 400. The imaging apparatus 400 includes an image pickup device 401 and a fluorescence microscope 402, and captures a bright field image of an analysis target preparation 408 set on a stage 409. The analysis target preparation 408 has been subjected to staining in advance as described above. The disease analyzer 200A obtains the analysis target image 78 captured by the imaging apparatus 400.

As the imaging apparatus 300, 400, a known light microscope, a known virtual slide scanner, or the like that has a function of capturing a preparation can be used.

<Hardware Configuration of Training Apparatus>

Figure 7:
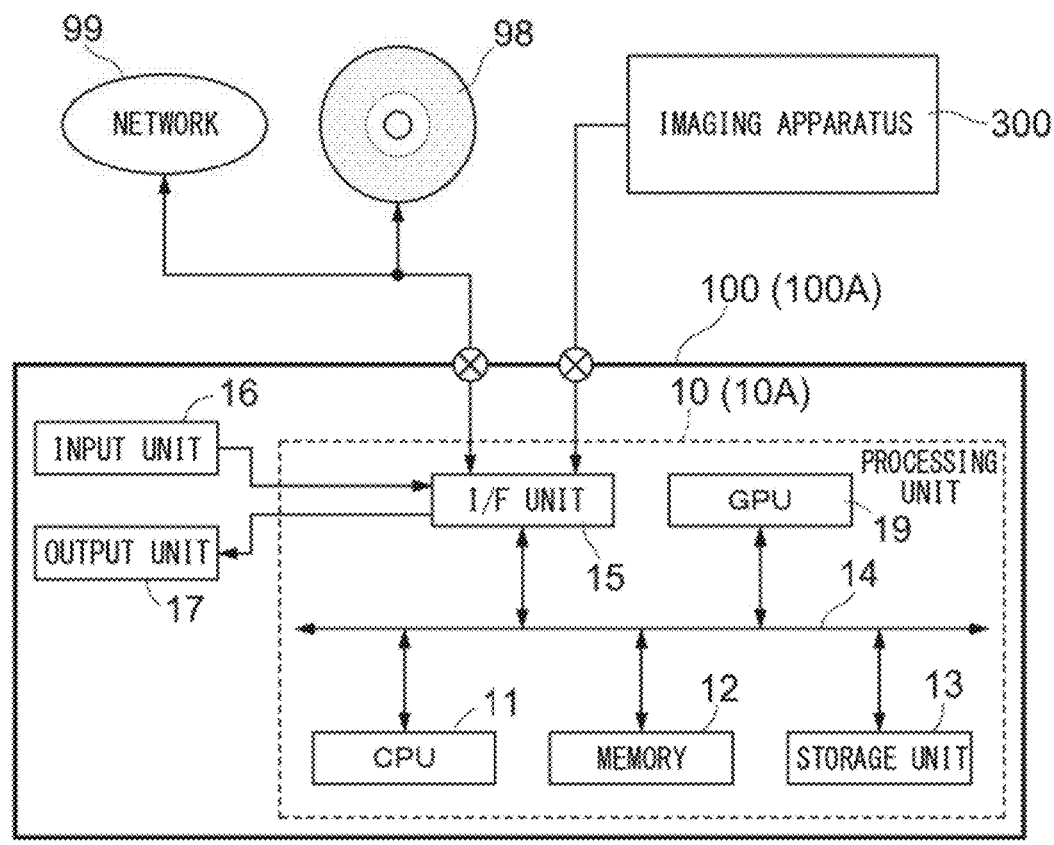
FIG. 7 is a block diagram showing an example of a hardware configuration of a vendor-side apparatus 100.

With reference to FIG. 7, the vendor-side apparatus 100 (the training apparatus 100A) includes a processing unit 10 (10A), an input unit 16, and an output unit 17.

The processing unit 10 includes a CPU (Central Processing Unit) 11 which performs data processing described later; a memory 12 to be used as a work area for data processing; a storage unit 13 which stores therein a program and process data described later; a bus 14 which transmits data between units; an interface unit 15 which inputs/outputs data with respect to an external apparatus, and a GPU (Graphics Processing Unit) 19. The input unit 16 and the output unit 17 are connected to the processing unit 10. For example, the input unit 16 is an input device such as a keyboard or a mouse, and the output unit 17 is a display device such as a liquid crystal display. The GPU 19 functions as an accelerator that assists arithmetic processing (for example, parallel arithmetic processing) performed by the CPU 11. That is, the processing performed by the CPU 11 described below also includes processing performed by the CPU 11 using the GPU 19 as an accelerator.

In order to perform the process of each step described below with reference to FIG. 10, FIG. 13, and FIG. 14, the processing unit 10 has previously stored, in the storage unit 13, a program and a discriminator according to the present disclosure in an executable form, for example. The executable form is a form generated through conversion of a programming language by a compiler, for example. The processing unit 10 uses the program stored in the storage unit 13, to perform training processes on the first neural network 50, the second neural network 51, the second neural network 52, and the machine learning algorithm 57.

In the description below, unless otherwise specified, the process performed by the processing unit 10 means a process performed by the CPU 11 on the basis of the program stored in the storage unit 13 or the memory 12, as well as the first neural network 50, the second neural network 51, the second neural network 52, and the machine learning algorithm 57. The CPU 11 temporarily stores, in a volatile manner, necessary data (such as intermediate data being processed) using the memory 12 as a work area, and stores as appropriate in the storage unit 13, data to be saved for a long time such as calculation results, in a nonvolatile manner.

<Hardware Configuration of Disease Analyzer>

Figure 8:
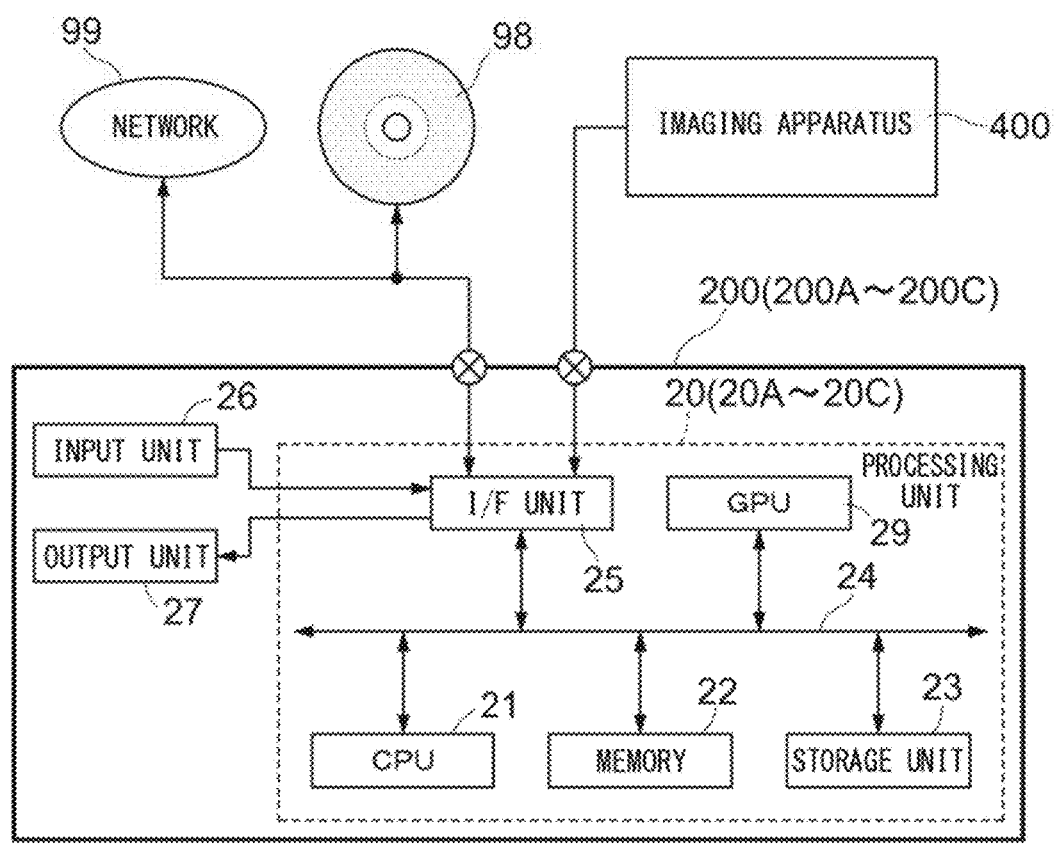
FIG. 8 is a block diagram showing an example of a hardware configuration of a user-side apparatus 200.

With reference to FIG. 8, the user-side apparatus 200 (disease analyzer 200A, disease analyzer 200B, disease analyzer 200C) includes a processing unit 20 (20A, 20B, 20C), an input unit 26, and an output unit 27.

The processing unit 20 includes a CPU (Central Processing Unit) 21 which performs data processing described later; a memory 22 to be used as a work area for data processing; a storage unit 23 which stores therein a program and process data described later; a bus 24 which transmits data between units; an interface unit 25 which inputs/outputs data with respect to an external apparatus; and a GPU (Graphics Processing Unit) 29. The input unit 26 and the output unit 27 are connected to the processing unit 20. For example, the input unit 26 is an input device such as a keyboard or a mouse, and the output unit 27 is a display device such as a liquid crystal display. The GPU 29 functions as an accelerator that assists arithmetic processing (for example, parallel arithmetic processing) performed by the CPU 21. That is, the processing performed by the CPU 21 described below also includes processing performed by the CPU 21 using the GPU 29 as an accelerator.

In order to perform the process of each step described in the disease analysis process below, the processing unit 20 has previously stored, in the storage unit 23, a program and the discriminator according to the present disclosure in an executable form, for example. The executable form is a form generated through conversion of a programming language by a compiler, for example. The processing unit 20 uses the program and the discriminator stored in the storage unit 23, to perform a process.

In the description below, unless otherwise specified, the process performed by the processing unit 20 means a process performed, in actuality, by the CPU 21 of the processing unit 20 on the basis of the program and the deep learning algorithm 60 stored in the storage unit 23 or the memory 22. The CPU 21 temporarily stores, in a volatile manner, necessary data (such as intermediate data being processed) using the memory 22 as a work area, and stores as appropriate in the storage unit 23, data to be saved for a long time such as calculation results, in a nonvolatile manner.

<Function Block and Processing Procedure>

(Deep Learning Process)

Figure 9:
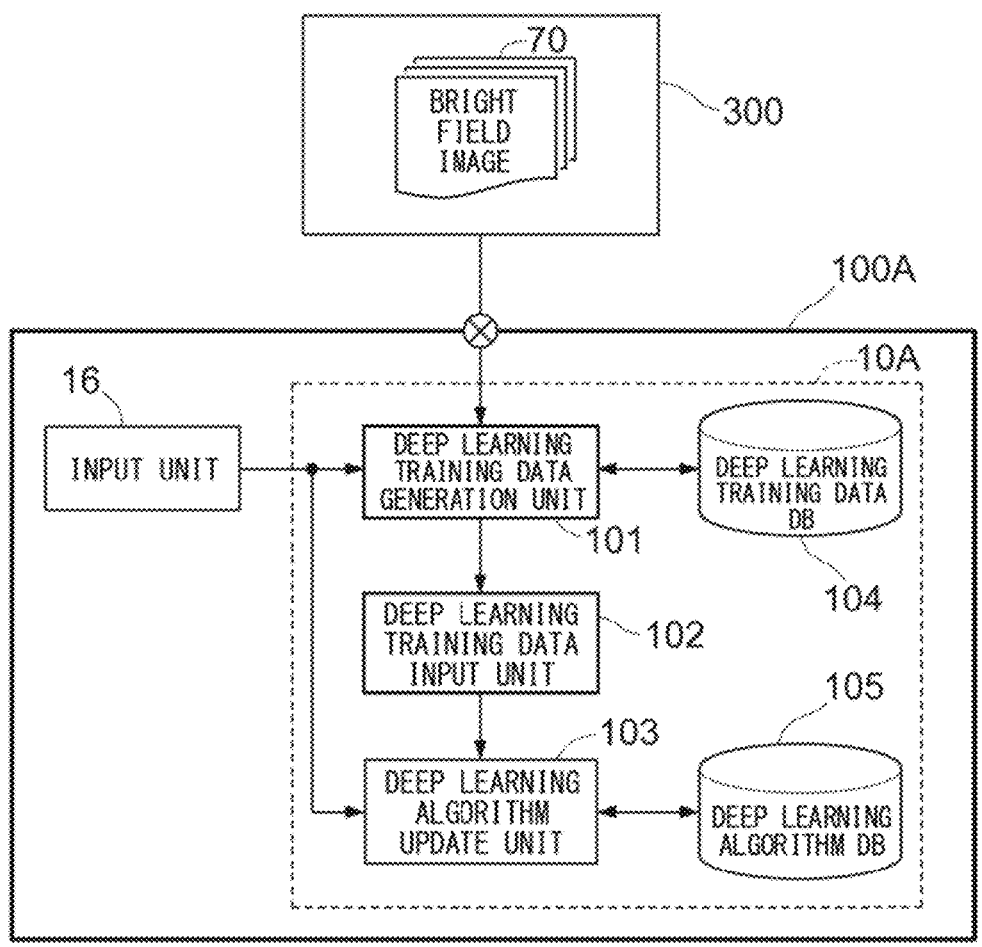
FIG. 9 is a block diagram for describing an example of functions of a training apparatus 100A.

With reference to FIG. 9, the processing unit 10A of the training apparatus 100A includes a deep learning training data generation unit 101, a deep learning training data input unit 102, and a deep learning algorithm update unit 103. These function blocks are realized when a program for causing a computer to execute the deep learning process is installed in the storage unit 13 or the memory 12 of the processing unit 10A; and the program is executed by the CPU 11. A deep learning training data database (DB) 104 and a deep learning algorithm database (DB) 105 are stored in the storage unit 13 or the memory 12 of the processing unit 10A.

Each training image 70 is captured in advance by the imaging apparatus 300 and is stored in advance in the storage unit 13 or the memory 12 of the processing unit 10A, in association with the morphological type of cell or abnormal finding to which an analysis target cell belongs, for example. The first neural network 50, and the second neural network 51 and the second neural network 52 that have not been trained are stored in the deep learning training data database 104 in advance. The first neural network 50, and the second neural network 51 and the second neural network 52 that have been trained once and are to be updated are stored in the deep learning algorithm database 105 in advance.

Figure 10:
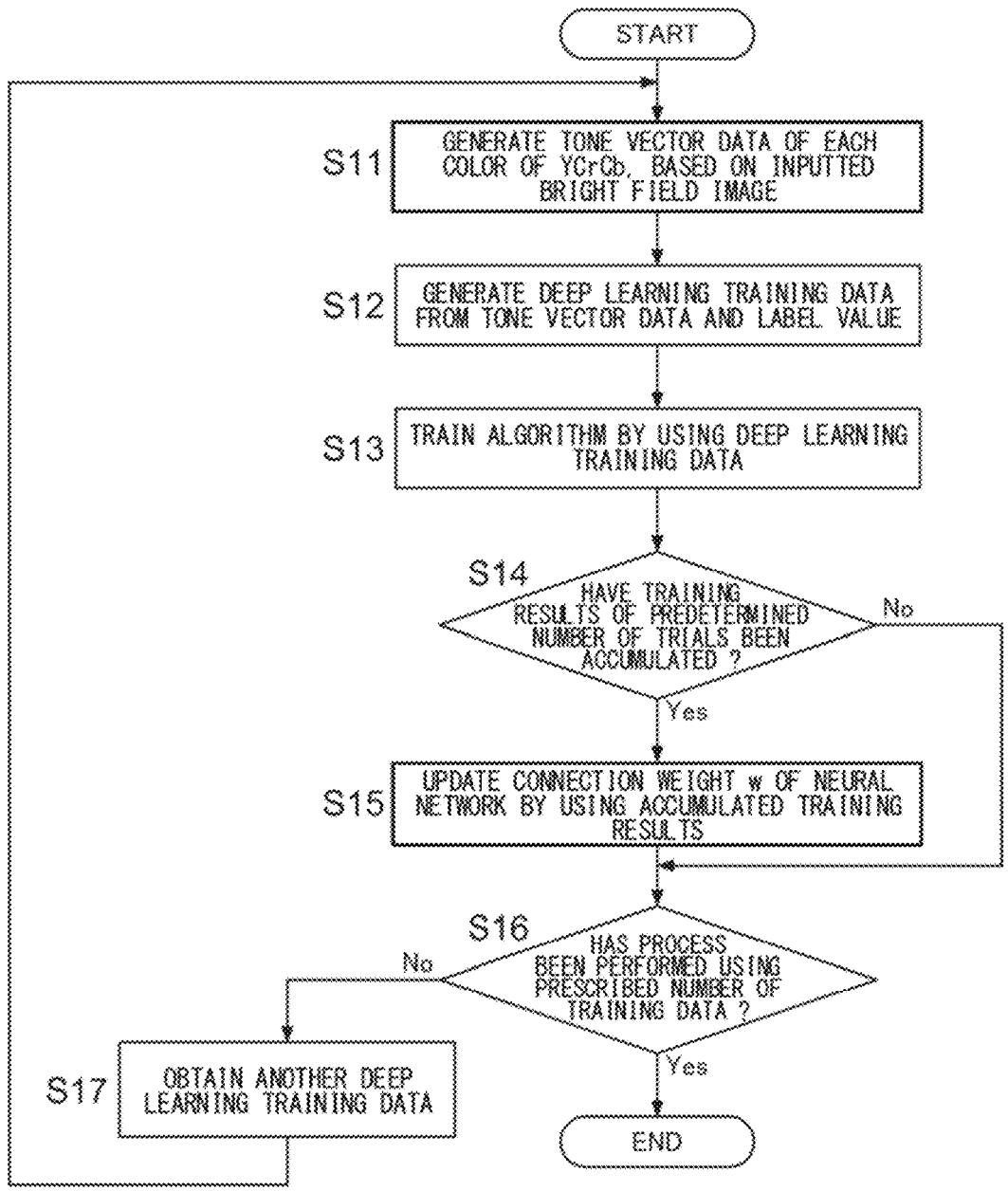
FIG. 10 is a flow chart showing an example of the flow of a deep learning process.

The processing unit 10A of the training apparatus 100A performs the process shown in FIG. 10. With reference to the function blocks shown in FIG. 9, the processes of steps S11, S12, S16, and S17 are performed by the deep learning training data generation unit 101. The process of step S13 is performed by the deep learning training data input unit 102. The process of step S14 is performed by the deep learning algorithm update unit 103.

An example of the deep learning process performed by the processing unit 10A is described with reference to FIG. 10. First, the processing unit 10A obtains training images 70. Each training image 70 is obtained via the I/F unit 15 through an operation by an operator, from the imaging apparatus 300, from the storage medium 98, or via a network. When the training image 70 is obtained, information regarding which of the morphologically classified cell type and/or abnormal finding is indicated by the training image 70 is also obtained. The information regarding which of the morphologically classified cell type and/or abnormal finding is indicated may be associated with the training image 70, or may be inputted by the operator through the input unit 16.

In step S11, the processing unit 10A converts the obtained training image 70 into brightness Y, first hue Cb, and second hue Cr, and generates tone vector data 74 in accordance with the procedure described in the training data generation method above.

In step S12, the processing unit 10A provides a label value that corresponds to the tone vector data 74, on the basis of the information associated with the training image 70 and regarding which of the morphologically classified cell type and/or abnormal finding is indicated; and the label value associated with the morphologically classified cell type or abnormal finding stored in the memory 12 or the storage unit 13. In this manner, the processing unit 10A generates the deep learning training data 75.

In step S13 shown in FIG. 10, the processing unit 10A trains the first neural network 50 and the second neural network 51 by using the deep learning training data 75. The training results of the first neural network 50 and the second neural network 51 are accumulated every time training is performed by using a plurality of the deep learning training data 75.

Next, in step S14, the processing unit 10A determines whether or not training results of a previously-set predetermined number of trials have been accumulated. When the training results of the predetermined number of trials have been accumulated (YES), the processing unit 10A advances to the process of step S15, and when the training results of the predetermined number of trials have not been accumulated (NO), the processing unit 10A advances to the process of step S16.

Next, when the training results of the predetermined number of trials have been accumulated, the processing unit 10A updates, in step S15, connection weights w of the first neural network 50 and the second neural network 51, or of the first neural network 50 and the second neural network 52, by using the training results accumulated in step S13. In the disease analysis method, the stochastic gradient descent method is used. Thus, the connection weights w of the first neural network 50 and the second neural network 51, or of the first neural network 50 and the second neural network 52 are updated at a stage where learning results of the predetermined number of trials have been accumulated. Specifically, the process of updating the connection weights w is a process of performing calculation according to the gradient descent method, expressed in Formula 11 and Formula 12 described later.

In step S16, the processing unit 10A determines whether or not the first neural network 50 and the second neural network 51 or the first neural network 50 and the second neural network 52 have been trained using a prescribed number of pieces of training data 75. When the training has been performed using the prescribed number of pieces of training data 75 (YES), the deep learning process ends.

When the first neural network 50 and the second neural network 51 or the first neural network 50 and the second neural network 52 have not been trained using the prescribed number of pieces of training data 75 (NO), the processing unit 10A advances from step S16 to step S17, and performs the processes from step S11 to step S16 with respect to the next training image 70.

In accordance with the process described above, the first neural network 50 and the second neural network 51 or the first neural network 50 and the second neural network 52 are trained, whereby the 1st deep learning algorithm and the 2nd deep learning algorithm are obtained.

(Structure of Neural Network)

Figure 11A:
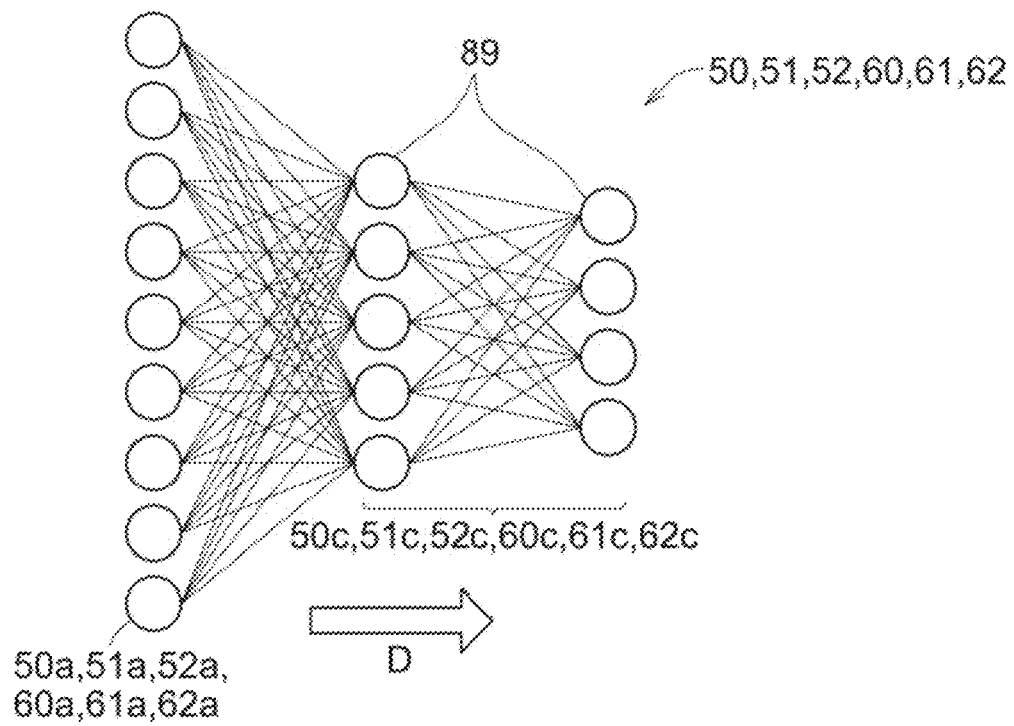
FIG. 11A is a schematic diagram for describing a neural network.

FIG. 11A shows an example of the structure of the first neural network 50 and the second neural networks 51, 52. The first neural network 50 and the second neural networks 51, 52 include the input layers 50a, 51a, 52a; the output layers 50b, 51b, 52b; and the middle layers 50c, 51c, 52c between the input layers 50a, 51a, 52a and the output layers 50b, 51b, 52b. Each middle layer 50c, 51c, 52c is composed of a plurality of layers. The number of layers forming the middle layer 50c, 51c 52c can be 5 or greater, for example.

In the first neural network 50 and the second neural network 51, or in the first neural network 50 and the second neural network 52, a plurality of nodes 89 arranged in a layered manner are connected between the layers. Accordingly, information propagates only in one direction indicated by the arrow D in the figure, from the input-side layer 50a, 51a, 52a to the output-side layer 50b, 51b, 52b.

(Calculation at Each Node)

Figure 11B:
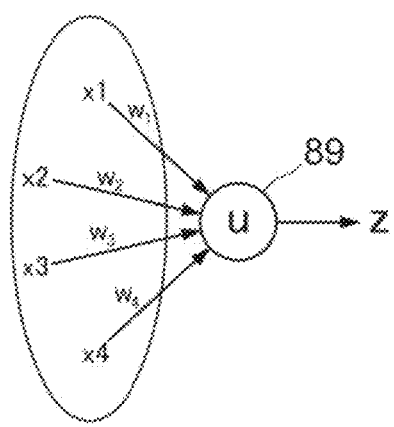
FIG. 11B is a schematic diagram for describing the neural network.

FIG. 11B is a schematic diagram showing calculation performed at each node. Each node 89 receives a plurality of inputs and calculates one output (z). In the case of the example shown in FIG. 11B, the node 89 receives four inputs. The total input (u) received by the node 89 is expressed by Formula 1 below.

[Math 1]

$$u = w_1 x_1 + w_2 x_2 + w_3 x_3 + w_4 x_4 + b \quad \text{(Formula 1)}$$

Each input is multiplied by a different weight. In Formula 1, b is a value called bias. The output (z) of the node serves as an output of a predetermined function f with respect to the total input (u) expressed by Formula 1, and is expressed by Formula 2 below. The function f is called an activation function.

[Math 2]

$$z = f(u) \quad (式 2) \tag{Formula 2}$$

Figure 11C:
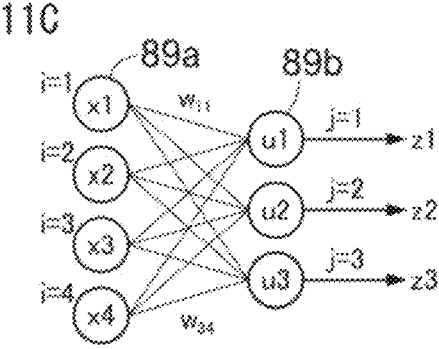
FIG. 11C is a schematic diagram for describing the neural network.

FIG. 11C is a schematic diagram illustrating calculation between nodes. In the first neural network 50 and the second neural network 51, 52, with respect to the total input (u) expressed by Formula 1, nodes that output results (z) each expressed by Formula 2 are arranged in a layered manner. Outputs from the nodes of the previous layer serve as inputs to the nodes of the next layer. In the example shown in FIG. 11C, the outputs from nodes 89a in the left layer in the figure serve as inputs to nodes 89b in the right layer. Each node 89b in the right layer receives outputs from the respective nodes 89a in the left layer. The connection between each node 89a in the left layer and each node 89b in the right layer is multiplied by a different weight. When the respective outputs from the plurality of nodes 89a of the left layer are defined as $x_1$ to $x_4$, the inputs to the respective three nodes 89b in the right layer are expressed by Formula 3-1 to Formula 3-3 below.

[Math 3]

$$u_1 = w_{11}x_1 + w_{12}x_2 + w_{13}x_3 + w_{14}x_4 + b_1 \quad (式 3\text{-}1) \tag{Formula 3-1}$$

$$u_2 = w_{21}x_1 + w_{22}x_2 + w_{23}x_3 + w_{24}x_4 + b_2 \quad (式 3\text{-}2) \tag{Formula 3-2}$$

$$u_3 = w_{31}x_1 + w_{32}x_2 + w_{33}x_3 + w_{34}x_4 + b_3 \quad (式 3\text{-}3) \tag{Formula 3-3}$$

When Formula 3-1 to Formula 3-3 are generalized, Formula 3-4 is obtained. Here, i=1, . . . I, j=1, . . . J.

[Math 4]

$$u_j = \Sigma_{i=1}^{I} w_{ji}x_i + b_j \quad (式 3\text{-}4) \tag{Formula 3-4}$$

When Formula 3-4 is applied to an activation function, an output is obtained. The output is expressed by Formula 4 below.

[Math 5]

$$z_j = f(u_j)(j=1,2,3) \quad (式 4) \tag{Formula 4}$$

(Activation Function)

In the disease analysis method, a rectified linear unit function is used as the activation function. The rectified linear unit function is expressed by Formula 5 below.

[Math 6]

$$f(u) = \max(u, 0) \tag{Formula 5}$$

Formula 5 is a function obtained by setting u=0 to the part u<0 in the linear function with z=u. In the example shown in FIG. 11C, using Formula 5, the output from the node of j=1 is expressed by the formula below.

$$z_1 = \max((w_{11}x_1 w_{12}x_2 + w_{13}x_3 + w_{14}x_4 + b_1), 0) \quad [\text{Math 7}]$$

(Neural Network Learning)

If the function expressed by use of a neural network is defined as y(x:w), the function y(x:w) varies when a parameter w of the neural network is varied. Adjusting the function y(x:w) such that the neural network selects a more suitable parameter w with respect to the input x is referred to as neural network learning. It is assumed that a plurality of pairs of an input and an output of the function expressed by use of the neural network have been given. If a desirable output for an input x is defined as d, the pairs of the input/output are given as $\{(x_1,d_1), (x_2,d_2), \ldots, (x_n,d_n)\}$. The set of pairs each expressed as (x,d) is referred to as training data. Specifically, the set of pairs of a label of the true value image and a color density value for each pixel in a single color image of each color, Y, Cb, or Cr shown in FIG. 2 is the training data in FIG. 2.

The neural network learning means adjusting the weight w such that, with respect to any input/output pair $(x_n, d_n)$, the output $y(x_n:w)$ of the neural network when given an input $x_n$, becomes close to the output $d_n$, as much as possible. An error function is a function for measuring the closeness $$y(x_n:w) \approx d_n \qquad [\text{Math 8}]$$

between the training data and a function expressed by use of the neural network. The error function is also called a loss function. An error function E(w) used in the disease analysis method is expressed by Formula 6 below. Formula 6 is called cross entropy.

[Math 9]

$$E(w) = -\Sigma_{n=1}^{N} \Sigma_{k=1}^{K} d_{nk} \log y_k(x_n:w) \quad (式 6) \tag{Formula 6}$$

A method for calculating the cross entropy in Formula 6 is described. In the output layer 50b of the neural network 50 to be used in the disease analysis method, i.e., in the last layer of the neural network, an activation function is used that classifies inputs x into a finite number of classes according to the contents. The activation function is called a softmax function and expressed by Formula 7 below. It is assumed that, in the output layer 50b, the nodes are arranged by the same number as the number of classes k. It is assumed that the total input u of each node k (k=1, . . . K) of an output layer L is given as $u_k^{(L)}$ from the outputs of the previous layer L−1. Accordingly, the output of the k-th node in the output layer is expressed by Formula 7 below.

[Math 10]

$$y_k \equiv z_k^{(L)} = \frac{\exp(u_k^{(L)})}{\sum_{j=1}^{K} \exp(u_j^{(L)})} \quad (式 7) \tag{Formula 7}$$

Formula 7 is the softmax function. The sum of output $y_1, \ldots, y_K$ determined by Formula 7 is always 1.

When each class is expressed as $C_1, \ldots, C_K$, output $y_K$ of node k in the output layer L (i.e., $u_k^{(L)}$) represents the probability that a given input x belongs to class $C_K$. Refer to Formula 8 below. The input x is classified into a class in which the probability expressed by Formula 8 becomes largest.

[Math 11]

$$p(C_k|x) = y_k = z_k^{(L)} \quad (式 8) \tag{Formula 8}$$

In the neural network learning, a function expressed by the neural network is considered as a model of the posterior probability of each class, the likelihood of the weight w with respect to the training data is evaluated under such a probability model, and a weight w that maximizes the likelihood is selected.

It is assumed that target output $d_n$ by the softmax function of Formula 7 is 1 only if the output is a correct class, and otherwise, target output $d_n$ is 0. In a case where the target output is expressed in a vector format of $d_n = [d_{n1}, \ldots, d_{nK}]$, if, for example, the correct class for input $x_n$ is $C_3$, only target output $d_{n3}$ becomes 1, and the other target outputs become 0. When coding is performed in this manner, the posterior distribution is expressed by Formula 9 below.

[Math 12]

$$p(d|x)=\Pi_{k=1}^{K} p(C_k|x)^{d_k} \quad (\text{式 9})$$ (Formula 9)

Likelihood L(w) of weight w with respect to the training data $\{(x_n,d_n)\}(n=1, \ldots, N)$ is expressed by Formula 10 below. When the logarithm of likelihood L(w) is taken and the sign is inverted, the error function of Formula 6 is derived.

[Math 13]

$$L(w) = \prod_{n=1}^{N} p(d_n \mid x_n; w) = \prod_{n=1}^{N} \prod_{k=1}^{K} p(C_k \mid x_n)^{d_{nk}}$$

$$= \prod_{n=1}^{N} \prod_{k=1}^{K} (y_k(x; w))^{d_{nk}} \quad (\text{式 10})$$ (Formula 10)

Learning means minimizing error function E(w) calculated on the basis of the training data, with respect to parameter w of the neural network. In the disease analysis method, error function E(w) is expressed by Formula 6.

Minimizing error function E(w) with respect to parameter w has the same meaning as finding a local minimum point of function E(w). Parameter w is a weight of connection between nodes. The local minimum point of weight w is obtained by iterative calculation of repeatedly updating parameter w from an arbitrary initial value as a starting point. An example of such calculation is the gradient descent method.

In the gradient descent method, a vector expressed by Formula 11 below is used.

[Math 14]

$$\nabla E = \frac{\partial E}{\partial w} = \left[\frac{\partial E}{\partial w_1}, \ldots, \frac{\partial E}{\partial w_M}\right]^T \quad (\text{式 11})$$ (Formula 11)

In the gradient descent method, a process of moving the value of current parameter w in the negative gradient direction (i.e., $-\nabla E$) is repeated many times. If it is assumed that $w^{(t)}$ is the current weight and that $w^{(t+1)}$ is the weight after the moving, the calculation according to the gradient descent method is expressed by Formula 12 below. Value t means the number of times the parameter w is moved.

[Math 15]

$$w^{(t+1)}=w^{(t)}-\epsilon \nabla E \quad (\text{式 12})$$ (Formula 12)

$\epsilon$ [Math 16]

The above symbol is a constant that determines the magnitude of the update amount of parameter w, and is called a learning coefficient. As a result of repetition of the calculation expressed by Formula 12, error function E ($w^{(t)}$) decreases in association with increase of value t, and parameter w reaches a local minimum point.

It should be noted that the calculation according to Formula 12 may be performed on all the training data (n=1, . . . , N) or may be performed on only part of the training data. The gradient descent method performed on only part of the training data is called a stochastic gradient descent method. In the disease analysis method, the stochastic gradient descent method is used.

(Machine Learning Process 1)

In a first machine learning process, the machine learning algorithm 57 is trained on the basis of the first information or the second information.

Figure 12:
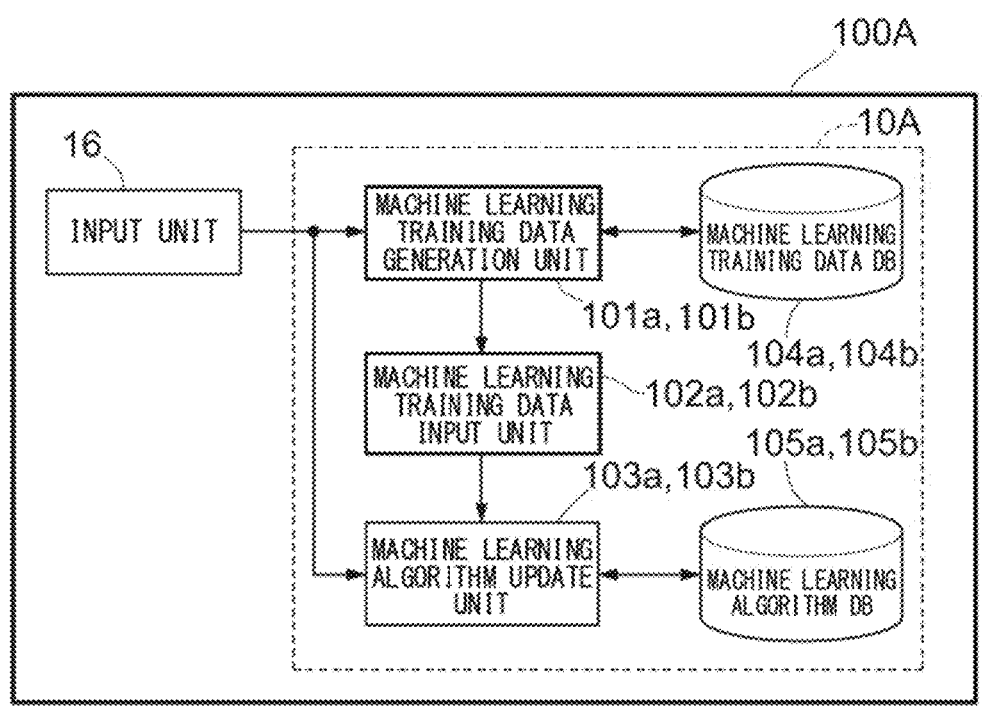
FIG. 12 is a block diagram for describing an example of functions of a machine learning apparatus 100A.

With reference to FIG. 12, the processing unit 10A of the training apparatus 100A trains the machine learning algorithm 57 on the basis of the first information 53 and the disease information 55. The processing unit 10A includes a machine learning training data generation unit 101a, a machine learning training data input unit 102a, and a machine learning algorithm update unit 103a. These function blocks are realized when a program for causing a computer to execute the machine learning process is installed in the storage unit 13 or the memory 12 of the processing unit 10A; and the program is executed by the CPU 11. A machine learning training data database (DB) 104a and a machine learning algorithm database (DB) 105a are stored in the storage unit 13 or the memory 12 of the processing unit 10A.

The first information or the second information has been generated by the processing unit 10A, and is stored in advance in the storage unit 13 or the memory 12 of the processing unit 10A, in association with the morphological type of cell or abnormal finding to which an analysis target cell belongs, for example. The first neural network 50, and the second neural network 51 and the second neural network 52 that have not been trained are stored in advance in the machine learning training data database 104a. The first neural network 50, and the second neural network 51 and the second neural network 52 that have been trained once and are to be updated are stored in advance in the machine learning algorithm database 105a.

Figure 13:
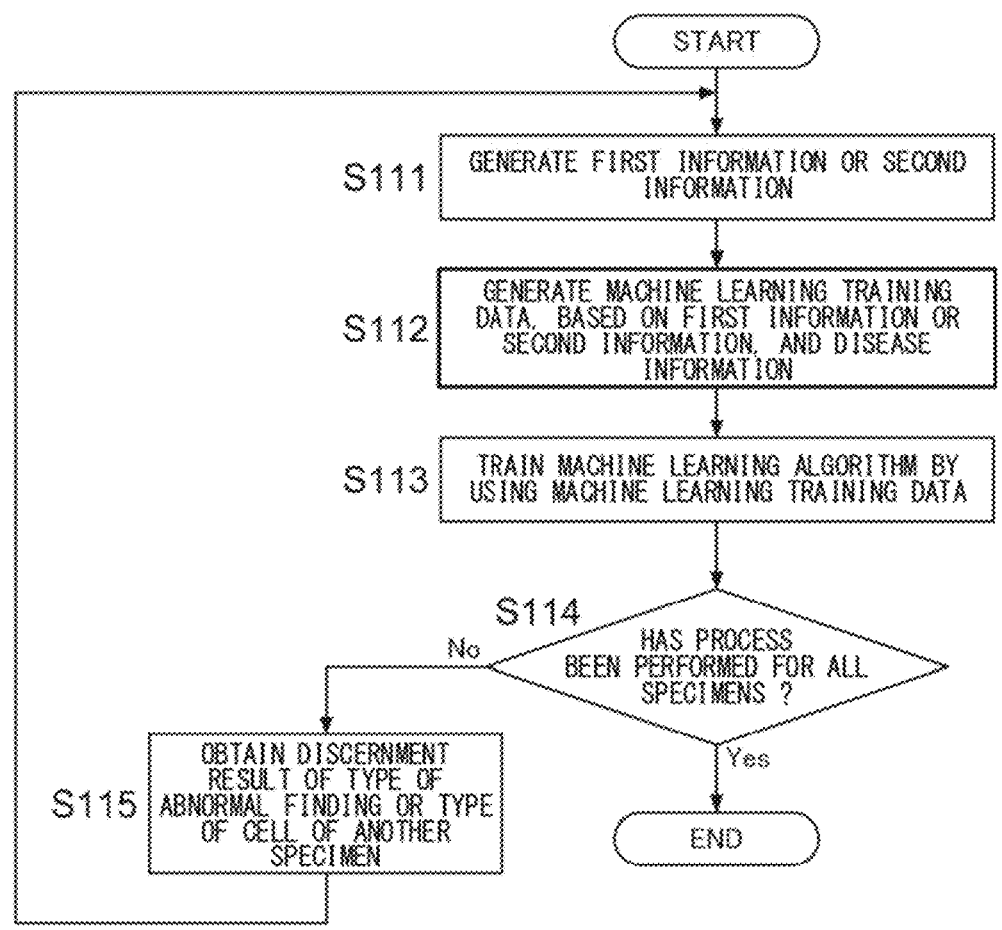
FIG. 13 is a flow chart showing an example of the flow of a machine learning process using first information.

The processing unit 10A of the training apparatus 100A performs the process shown in FIG. 13. With reference to the function blocks shown in FIG. 12, the processes of steps S111, S112, S114, and S115 are performed by the machine learning training data generation unit 101a. The process of step S113 is performed by the machine learning training data input unit 102a.

An example of the first machine learning process performed by the processing unit 10A is described with reference to FIG. 13.

The processing unit 10A of the training apparatus 100A generates, in step S111, the first information or the second information in accordance with the method described in the section of training of the machine learning algorithm above. Specifically, the processing unit 10A discerns the type of abnormal finding with respect to a cell in each training image 70 on the basis of the 1st deep learning algorithm or the 2nd deep learning algorithm having been trained through step S11 to step S16, and obtains a discernment result. For each cell, the discernment result of the type of abnormal finding is outputted from the second neural network 61. In step S111, on the basis of the discernment result of the type of abnormal finding, the processing unit 10A generates the first information for each specimen for which the training image 70 has been obtained. Alternatively, the processing unit 10A discerns the type of cell with respect to a cell in each training image 70 on the basis of the second neural network 62, and obtains a discernment result. On the basis of the discernment result of the type of cell, the processing unit 10A generates the second information for each specimen for which the training image 70 has been obtained.

Next, in step S112, the processing unit 10A generates the machine learning training data 90 on the basis of the first information and the disease information 55 associated with the training image 70. Alternatively, the processing unit 10A generates the machine learning training data 90 on the basis of the second information and the disease information 55 associated with the training image 70.

Next, in step S113, the processing unit 10A inputs the machine learning training data 90 to the machine learning algorithm, to train the machine learning algorithm.

Next, in step S114, the processing unit 10A determines whether the process has been performed on all the training specimens. When the process has been performed on all the training specimens, the process ends. When the process has not been performed on all the training specimens, the processing unit 10A advances to step S115, obtains a discernment result of the type of abnormal finding or a discernment result of the type of cell of another specimen, returns to step S111, and repeats training of the machine learning algorithm.

(Machine Learning Process 2)

In a second machine learning process, the machine learning algorithm 57 is trained on the basis of the first information and the second information.

With reference to FIG. 12, the processing unit 10A of the training apparatus 100A trains the machine learning algorithm 57 on the basis of the first information 53 and the disease information 55. The processing unit 10A includes a machine learning training data generation unit 101b, a machine learning training data input unit 102b, and a machine learning algorithm update unit 103b. These function blocks are realized when a program for causing a computer to execute the machine learning process is installed in the storage unit 13 or the memory 12 of the processing unit 10A; and the program is executed by the CPU 11. A machine learning training data database (DB) 104b and a machine learning algorithm database (DB) 105b are stored in the storage unit 13 or the memory 12 of the processing unit 10A.

The first information and the second information has been generated by the processing unit 10A, and is stored in advance in the storage unit 13 or the memory 12 of the processing unit 10A, in association with the morphological type of cell or abnormal finding to which an analysis target cell belongs, for example. The first neural network 50, and the second neural network 51 and the second neural network 52 that have not been trained are stored in advance in the machine learning training data database 104b. The first neural network 50, and the second neural network 51 and the second neural network 52 that have been trained once and are to be updated are stored in advance in the machine learning algorithm database 105b.

Figure 14:
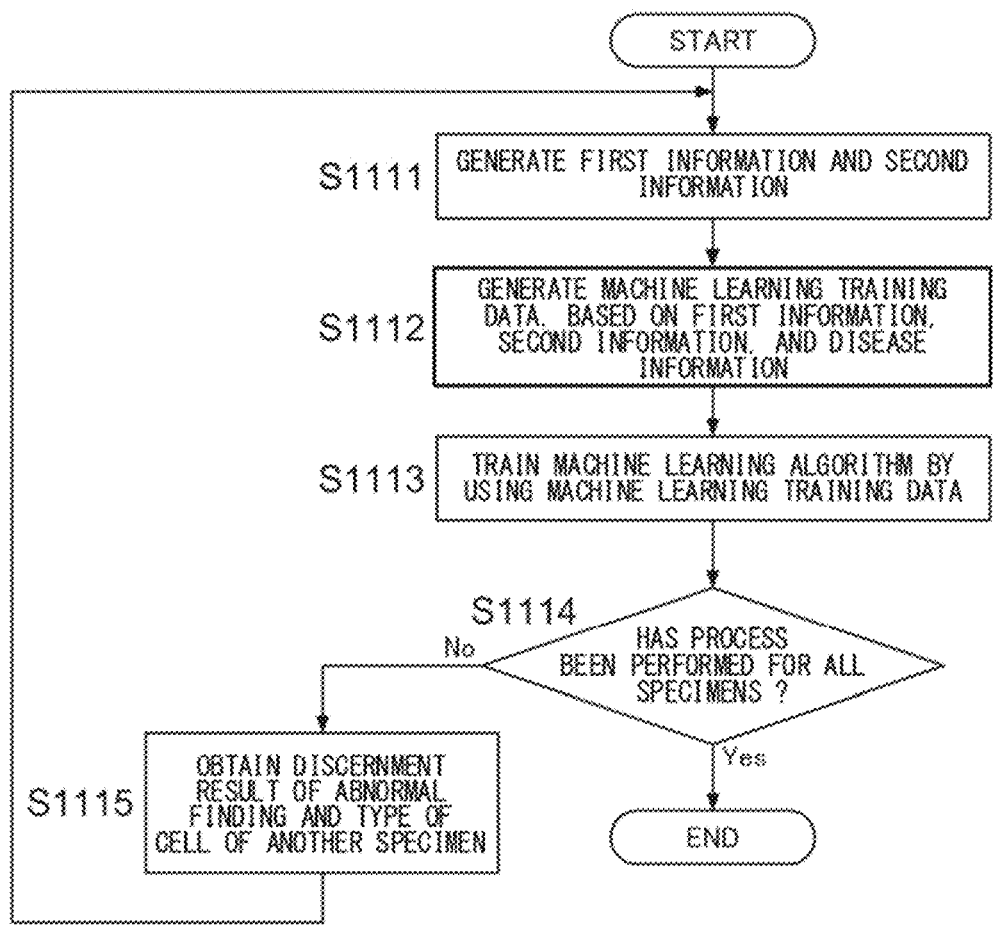
FIG. 14 is a flow chart showing an example of the flow of a machine learning process using the first information and second information.

The processing unit 10A of the training apparatus 100A performs the process shown in FIG. 14. With reference to the function blocks shown in FIG. 12, the processes in steps S1111, S1112, S1114, and S1115 are performed by the machine learning training data generation unit 101b. The process of step S1113 is performed by the machine learning training data input unit 102b.

An example of the second machine learning process performed by the processing unit 10A is described with reference to FIG. 14. The processing unit 10A of the training apparatus 100A generates, in step S1111, the first information and the second information in accordance with the method described in the section of training of the machine learning algorithm above. Specifically, the processing unit 10A discerns the type of abnormal finding with respect to a cell in each training image 70 on the basis of the 1st deep learning algorithm and the 2nd deep learning algorithm having been trained through step S11 to step S16, and obtains a discernment result. For each cell, the discernment result of the type of abnormal finding is outputted from the second neural network 61. In step S1111, on the basis of the discernment result of the type of abnormal finding, the processing unit 10A generates the first information for each specimen for which the training image 70 has been obtained. In addition, the processing unit 10A discerns the type of cell with respect to a cell in each training image 70 on the basis of the second neural network 62, and obtains a discernment result. On the basis of the discernment result of the type of cell, the processing unit 10A generates the second information for each specimen for which the training image 70 has been obtained.

Next, in step S1112, the processing unit 10A generates the machine learning training data 90 on the basis of the first information, the second information, and the disease information 55 associated with the training image 70.

Next, in step S1113, the processing unit 10A inputs the machine learning training data 90 to the machine learning algorithm, to train the machine learning algorithm.

Next, in step S1114, the processing unit 10A determines whether the process has been performed on all the training specimens. When the process has been performed on all the training specimens, the process ends. When the process has not been performed on all the training specimens, the processing unit 10A advances to step S1115, obtains a discernment result of the type of abnormal finding and a discernment result of the type of cell of another specimen, returns to step S1111, and repeats training of the machine learning algorithm.

The outline of the machine learning algorithm used in step S113 and S1113 is as follows.

As the machine learning algorithm, ensemble learning (classifier configured by a plurality of classifiers) such as Gradient Boosting can be used. Examples of ensemble learning include Extreme Gradient Boosting (EGB) and Stochastic Gradient Boosting. Gradient Boosting is a type of boosting algorithm, and is a technique of forming a plurality of weak learners. As the weak learner, regression tree can be used, for example.

For example, in regression tree, when an input vector is defined as x and a label is defined as y, with respect to the entire learner $$F(x)=f_0(x)+f_1(x)+f_2(x)+ \ldots +f_M(x), \quad \text{[Math 17]}$$

weak learner fm(x), m=1, 2, ... M is sequentially learned and integrated so that loss function L(y, F(x)) becomes smallest. That is, it is assumed that function $F_0(x)=f_0(x)$ is given at the start of learning, and in the m-th step learning, with respect to a learner composed of m weak learners $$F_m(x)=F_{m-1}(x)+f_m(x), \quad \text{[Math 18]}$$

weak learner fm(x) is determined so that loss function L(y, F(x)) becomes smallest. In ensemble learning, when the weak learner is optimized, all pieces of data in the training set are not used, and pieces of data that realize "constant" at random are sampled to be used.

[Math 19]

(1) Constant function $F_0(x)$ that would minimize loss is obtained.

(2) For m=1 to M (a) N pieces of data are sampled from the training set to obtain set D.

(b) With respect to each element $(x_1,y_1),(x_x,y_2), \ldots (x_N,y_N)$ of the set D, gradient $$y_i' = \frac{\partial L(y_i, F_{m-1}(x_i))}{\partial F_{m-1}(x_i)}$$

is calculated.
(c) Regression tree T(x) that predicts the obtained gradient is generated
That is, a regression tree that minimizes $\Sigma_{i=1}^{N}(y_i^1-T(x_1))^2$ is generated.
This regression tree is weak learner $f_m(x)$.
(d) Weight of leaf of the regression tree T is optimized so that loss $\Sigma_{i=1}^{N}L(y_i,F_{m-1}(x_i)+T(x_i))$ becomes smallest.
(e) $F_t(x)$-$F_{m-1}(x)$+$vT(x)$ is set. v is shrinkage parameter, and is a constant that satisfies $0<v\le 1$.
(3) $F_M(x)$ is outputted as F(x).

Specifically, learner F(x) is obtained according to the algorithm below. The shrinkage parameter v may be set to 1, and $F_0(x)$ may be changed from a constant function.

(Disease Analysis Process)

Figure 15:
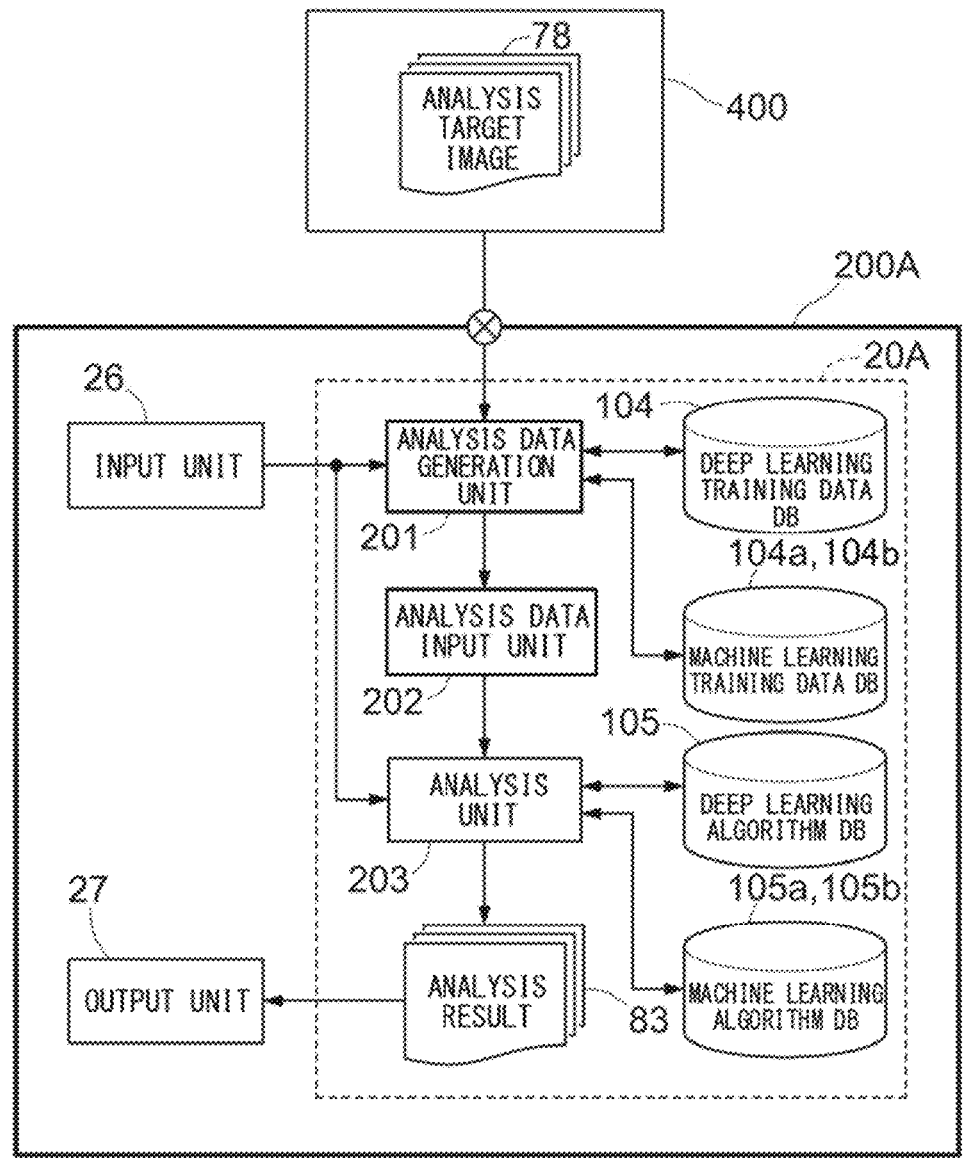
FIG. 15 is a block diagram for describing an example of functions of a disease analyzer 200A.

FIG. 15 shows a function block diagram of the disease analyzer 200A, which performs a disease analysis process up to generation of the analysis result 83 on the basis of the analysis target image 78. A processing unit 20A of the disease analyzer 200A includes an analysis data generation unit 201, an analysis data input unit 202, and an analysis unit 203. These function blocks are realized when; a program for causing a computer according to the present disclosure to execute the disease analysis process is installed in the storage unit 23 or the memory 22 of the processing unit 20A; and the program is executed by the CPU 21. The deep learning training data database (DB) 104 and the deep learning algorithm database (DB) 105 are provided from the training apparatus 100A through the storage medium 98 or the network 99, and are stored in the storage unit 23 or the memory 22 of the processing unit 20A. The machine learning training data database (DB) 104a, 104b, and the machine learning algorithm database (DB) 105a, 105b are provided from the training apparatus 100A through the storage medium 98 or the network 99, and are stored in the storage unit 23 or the memory 22 of the processing unit 20A.

Each analysis target image 78 is captured by the imaging apparatus 400 and is stored in the storage unit 23 or the memory 22 of the processing unit 20A. The first neural network 60 and the second neural networks 61, 62 which have been trained and which include connection weights w are stored in the deep learning algorithm database 105, in association the morphological-classification-based type of cell or type of abnormal finding to which the analysis target cell belongs, for example. The first neural network 60 and the second neural networks 61, 62 function as program modules which are part of the program that causes a computer to execute the disease analysis process. That is, the first neural network 60 and the second neural networks 61, 62 are used by the computer including a CPU and a memory, and output a discernment result of the type of abnormal finding or a discernment result of the type of cell. The CPU 21 of the processing unit 20A causes the computer to execute calculation or processing of specific information according to the intended use. The trained machine learning algorithm 67 is stored in the machine learning algorithm database 105a, 105b, and functions as a program module which is part of the program that causes the computer to execute the disease analysis process. That is, the machine learning algorithm 67 is used by the computer including a CPU and a memory, and outputs a disease analysis result.

Specifically, the CPU 21 of the processing unit 20A generates, in the analysis data generation unit 201, a discernment result of the type of abnormal finding, by using the 1st deep learning algorithm stored in the storage unit 23 or the memory 22. The processing unit 20A generates, in the analysis data generation unit 201, the first information 63 on the basis of the discernment result of the type of abnormal finding. The generated first information 63 is inputted to the analysis data input unit 202 and is stored into the machine learning training data DB 104a. The processing unit 20A performs disease analysis in the analysis unit 203, and outputs an analysis result 83 to the output unit 27. Alternatively, the CPU 21 of the processing unit 20A generates, in the analysis data generation unit 201, a discernment result of the type of cell, by using the 2nd deep learning algorithm stored in the storage unit 23 or the memory 22. The processing unit 20A generates, in the analysis data generation unit 201, the second information 64 on the basis of the discernment result of the type of cell. The generated second information 64 is inputted to the analysis data input unit 202, and is stored into the machine learning training data DB 104b. The processing unit 20A performs disease analysis in the analysis unit 203, and outputs an analysis result 83 to the output unit 27.

Figure 16:
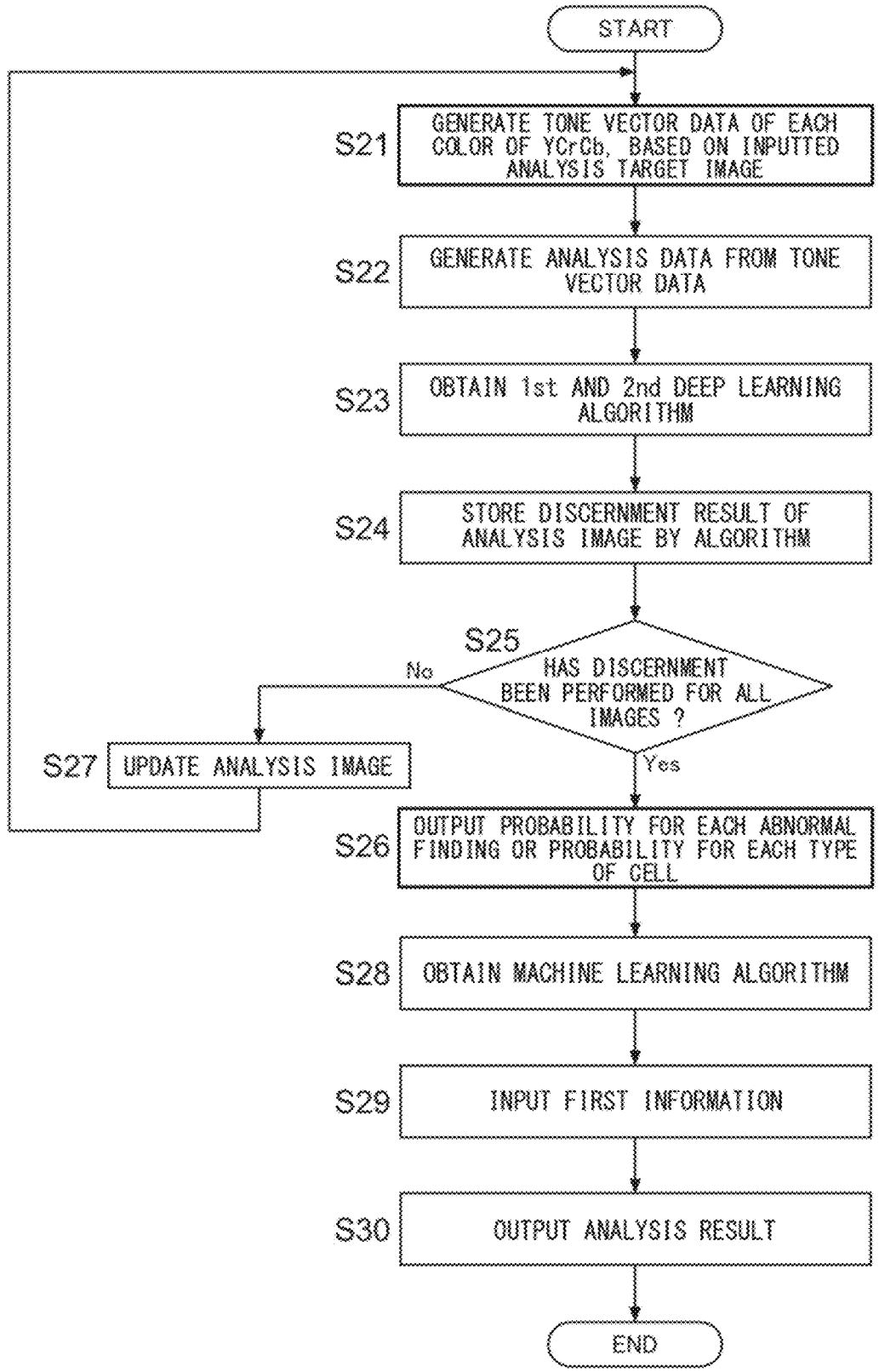
FIG. 16 is a flow chart showing an example of the flow of a disease analysis process using the first information.

With reference the function blocks shown in FIG. 15, the processes of steps S21 and S22 in FIG. 16 are performed by the analysis data generation unit 201. The processes of steps S23, S24, S25, and S27 are performed by the analysis data input unit 202. The process of step S26 is performed by the analysis unit 203.

(Disease Analysis Process 1)

With reference to FIG. 16, an example of a first disease analysis process up to outputting of an analysis result 83 on the basis of the analysis target image 78 performed by the processing unit 20A is described. In the first disease analysis process, the analysis result 83 is outputted on the basis of the first information or the second information.

First, the processing unit 20A obtains analysis images 78. Each analysis image 78 is obtained via the I/F unit 25 through an operation by a user, from the imaging apparatus 400, from the storage medium 98, or via a network.

Similar to step S11 shown in FIG. 10, in step S21, the obtained analysis image 78 is converted into brightness Y, first hue Cb, and second hue Cr, and the tone vector data 80 is generated in accordance with the procedure described in the analysis data generation method above.

Next, in step S22, the processing unit 20A generates the analysis data 81 from the tone vector data 80, in accordance with the procedure described in the analysis data generation method above.

Next, in step S23, the processing unit 20A obtains the 1st deep learning algorithm or the 2nd deep learning algorithm stored in the algorithm database 105.

Next, in step S24, the processing unit 20A inputs the analysis data 81 to the first neural network 60 forming the 1st deep learning algorithm. In accordance with the procedure described in the disease analysis method above, the processing unit 20A inputs the feature quantity outputted from the first neural network 60, to the second neural network 61, and outputs a discernment result of the type of abnormal finding from the second neural network 61. The processing unit 20A stores the discernment result into the memory 22 or the storage unit 23. Alternatively, in step S24, the processing unit 20A inputs the analysis data 81, to the first neural network 60 forming the 2nd deep learning algorithm. In accordance with the procedure described in the disease analysis method above, the processing unit 20A inputs the feature quantity outputted from the first neural network 60, to the second neural network 62, and outputs a discernment result of the type of cell from the second neural network 62. The processing unit 20A stores the discernment result into the memory 22 or the storage unit 23.

In step S25, the processing unit 20A determines whether the discernment has been performed on all the analysis images 78 obtained first. When the discernment has been performed on all the analysis images 78 (YES), the processing unit 20A advances to step S26, and generates the first information 63 on the basis of the discernment result of the type of abnormal finding, or generates the second information on the basis of the discernment result of the type of cell. When the discernment has not been performed on all the analysis images 78 (NO), the processing unit 20A advances to step S27, and performs the processes from step S21 to step S25 on the analysis images 78 for which the discernment has not been performed.

Next, in step S28, the processing unit 20A obtains the machine learning algorithm 67. Subsequently, in step S29, the processing unit 20A inputs the first information or the second information to the machine learning algorithm 67.

Lastly, in step S30, the processing unit 20A outputs an analysis result 83 to the output unit 27, as a disease name or a label value associated with the disease name.

Disease Analysis Process 2)

Figure 17:
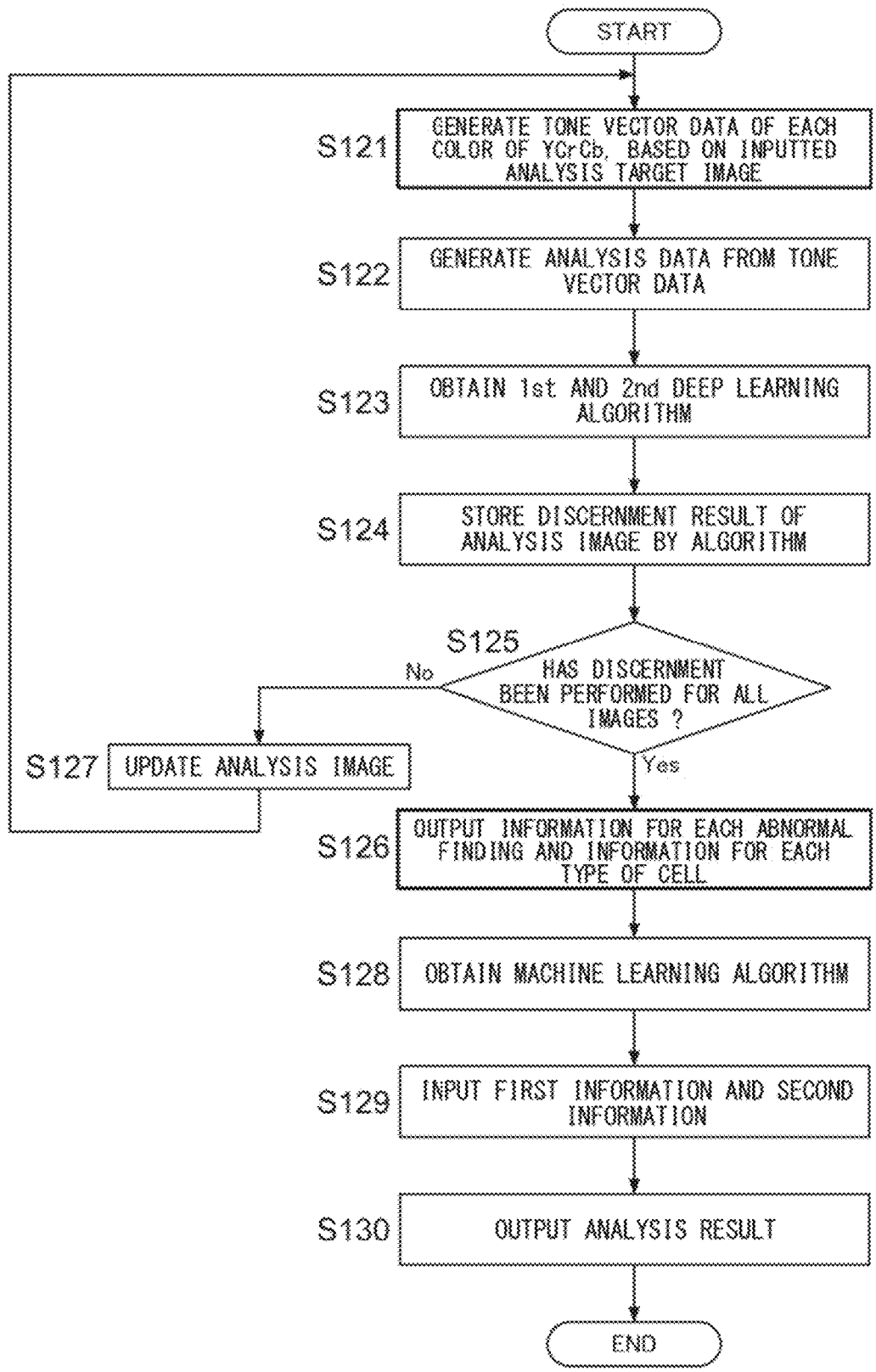
FIG. 17 is a flow chart showing an example of the flow of a disease analysis process using the first information and the second information.

With reference to FIG. 17, an example of a second disease analysis process up to outputting of an analysis result 83 on the basis of the analysis target image 78 performed by the processing unit 20A is described. In the second disease analysis process, the analysis result 83 is outputted on the basis of the first information and the second information.

First, the processing unit 20A obtains analysis images 78. Each analysis image 78 is obtained via the I/F unit 25 through an operation by a user, from the imaging apparatus 400, from the storage medium 98, or via a network.

Similar to step S11 shown in FIG. 10, in step S121, the obtained analysis image 78 is converted into brightness Y, first hue Cb, and second hue Cr, and the tone vector data 80 is generated in accordance with the procedure described in the analysis data generation method above.

Next, in step S122, the processing unit 20A generates the analysis data 81 from the tone vector data 80, in accordance with the procedure described in the analysis data generation method above.

Next, in step S123, the processing unit 20A obtains the 1st deep learning algorithm and the 2nd deep learning algorithm stored in the algorithm database 105.

Next, in step S124, the processing unit 20A inputs the analysis data 81 to the first neural network 60 forming the 1st deep learning algorithm. In accordance with the procedure described in the disease analysis method above, the processing unit 20A inputs the feature quantity outputted from the first neural network 60, to the second neural network 61, and outputs a discernment result of the type of abnormal finding from the second neural network 61. The processing unit 20A stores the discernment result into the memory 22 or the storage unit 23. In addition, in step S124, the processing unit 20A inputs the analysis data 81 to the first neural network 60 forming the 2nd deep learning algorithm. In accordance with the procedure described in the disease analysis method above, the processing unit 20A inputs the feature quantity outputted from the first neural network 60, to the second neural network 62, and outputs a discernment result of the type of cell from the second neural network 62. The processing unit 20A stores the discernment result into the memory 22 or the storage unit 23.

In step S125, the processing unit 20A determines whether the discernment has been performed on all the analysis images 78 obtained first. When the discernment has been performed on all the analysis images 78 (YES), the processing unit 20A advances to step S126, generates the first information 63 on the basis of the discernment result of the type of abnormal finding, and generates the second information on the basis of the discernment result of the type of cell. When the discernment has not been performed on all the analysis images 78 (NO), the processing unit 20A advances to step S127, and performs the processes from step S121 to step S125 on the analysis images 78 for which the discernment has not been performed.

Next, in step S128, the processing unit 20A obtains the machine learning algorithm 67. Subsequently, in step S129, the processing unit 20A inputs the first information and the second information to the machine learning algorithm 67.

Lastly, in step S130, the processing unit 20A outputs an analysis result 83 to the output unit 27, as a disease name or a label value associated with the disease name.

<Computer Program>

A computer program that is for assisting the disease analysis and that causes a computer to execute the processes of steps S21 to S30 or steps S121 to S130 is described. The computer program may include a program that is for training a machine learning algorithm and that causes a computer to execute the processes of steps S11 to S17 and steps S111 to S115, or a program that is for training a machine learning algorithm and that causes a computer to execute the processes of step S11 to S17 and step S1111 to S1115.

Further, a program product, such as a storage medium, having stored therein the computer program is described. The computer program is stored in a storage medium such as a hard disk, a semiconductor memory device such as a flash memory, or an optical disk. The storage form of the program into the storage medium is not limited in particular, as long as the processing unit can read the program. Preferably, the program is stored in the storage medium in a nonvolatile manner.

[Disease Analysis System 2]

<Configuration of Disease Analysis System 2>

Figure 18:
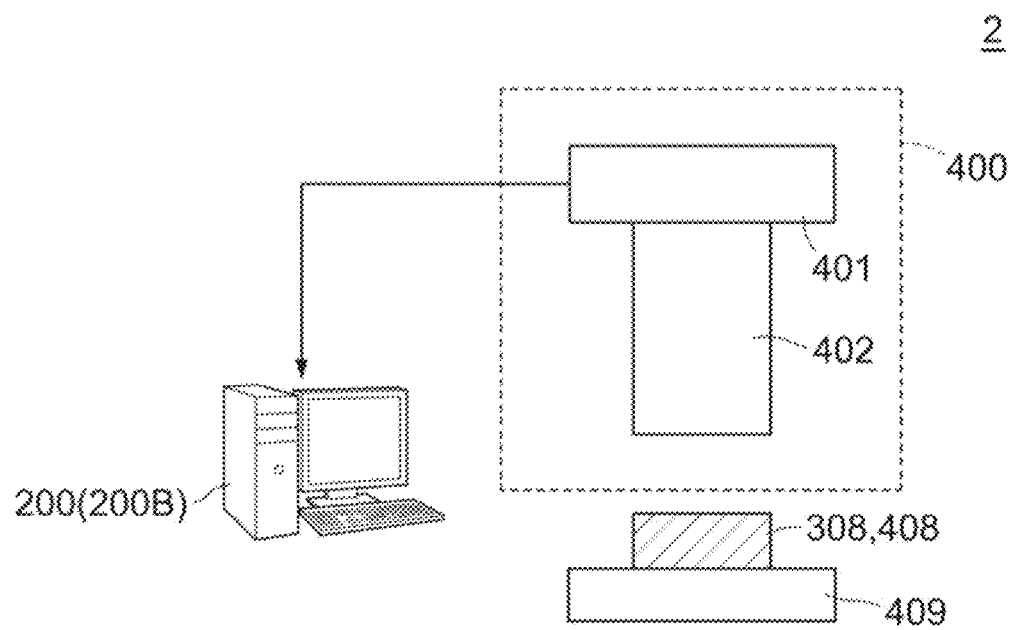
FIG. 18 shows a schematic configuration example of a disease analysis system 2.

Another aspect of the disease analysis system is described. FIG. 18 shows a configuration example of a disease analysis system 2. The disease analysis system 2 includes the user-side apparatus 200, and the user-side apparatus 200 operates as an integrated-type disease analyzer 200B. The disease analyzer 200B is implemented as a general purpose computer, for example, and performs both the deep learning process and the disease analysis process described in the disease analysis system 1 above. That is, the disease analysis system 2 is a stand-alone-type system that performs deep learning and disease analysis on the user side. In the disease analysis system 2, the integrated-type disease analyzer 200B installed on the user side has both functions of the training apparatus 100A and the disease analyzer 200A.

In FIG. 18, the disease analyzer 200B is connected to the imaging apparatus 400. The imaging apparatus 400 captures training images 70 during the deep learning process, and captures analysis target images 78 during the disease analysis process.

<Hardware Configuration>

The hardware configuration of the disease analyzer 200B is the same as the hardware configuration of the user-side apparatus 200 shown in FIG. 8.

<Function Block and Processing Procedure>

Figure 19:
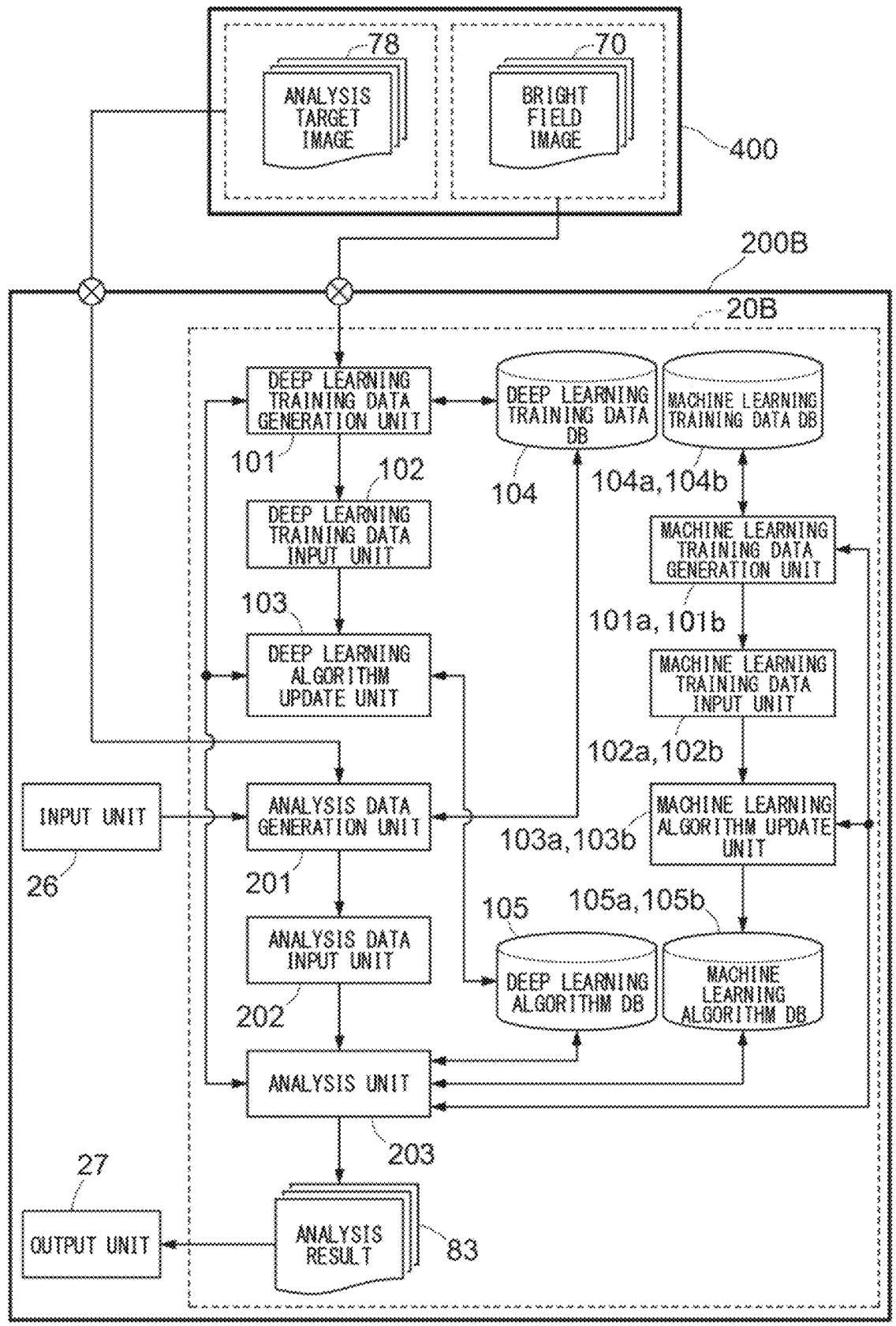
FIG. 19 is a block diagram for describing an example of functions of an integrated-type disease analyzer 200B.

FIG. 19 shows a function block diagram of the disease analyzer 200B. A processing unit 20B of the disease analyzer 200B includes the deep learning training data generation unit 101, the deep learning training data input unit 102, the deep learning algorithm update unit 103, the machine learning training data generation unit 101a, 101b, the machine learning training data input unit 102a, 102b, the machine learning algorithm update unit 103a, 103b, the analysis data generation unit 201, the analysis data input unit 202, and the analysis unit 203.

The processing unit 20B of the disease analyzer 200B performs the process shown in FIG. 10 during the deep learning process, performs the process shown in FIG. 13 or FIG. 14 during the machine learning process, and performs the process shown in FIG. 16 or FIG. 17 during the disease analysis process. With reference to the function blocks shown in FIG. 19, during the deep learning process, the processes of steps S11, S12, S16, and S17 in FIG. 10 are performed by the deep learning training data generation unit 101. The process of step S13 in FIG. 10 is performed by the deep learning training data input unit 102. The process of step S14 in FIG. 10 is performed by the deep learning algorithm update unit 103. During the machine learning process, the processes of steps S111, S112, S114, and S115 in FIG. 13 are performed by the machine learning training data generation unit 101a. The process of step S113 is performed by the machine learning training data input unit 102a. Alternatively, during the machine learning process, the processes of steps S1111, S1112, S1114, and S1115 in FIG. 14 are performed by the machine learning training data generation unit 101b. The process of step S1113 in FIG. 14 is performed by the machine learning training data input unit 102b. During the disease analysis process, the processes of steps S21 and S22 in FIG. 16 are performed by the analysis data generation unit 201. The processes of steps S23, S24, S25, and S27 in FIG. 16 are performed by the analysis data input unit 202. The process of step S26 in FIG. 16 is performed by the analysis unit 203. Alternatively, the processes of steps S121 and S122 in FIG. 17 are performed by the analysis data generation unit 201. The processes of steps S123, S124, S125, and S127 in FIG. 17 are performed by the analysis data input unit 202. The process of step S126 in FIG. 16 is performed by the analysis unit 203.

The procedures of the deep learning process and the disease analysis process performed by the disease analyzer 200B are the same as the procedures of those performed by the training apparatus 100A and the disease analyzer 200A. However, the disease analyzer 200B obtains the training image 70 from the imaging apparatus 400.

In the disease analyzer 200B, the user can confirm the discerning accuracy of the discriminator. Should the discernment result by the discriminator be different from the discernment result according to the observation of the image by the user, if the analysis data 81 is used as the training data 75, and the discernment result according to the observation of the image by the user is used as the label value 77, it is possible to train the 1st deep learning algorithm and the 2nd deep learning algorithm again. Accordingly, the training efficiency of the first neural network 50 and the second neural network 51 can be improved.

[Disease Analysis System 3]

<Configuration of Disease Analysis System 3>

Figure 20:
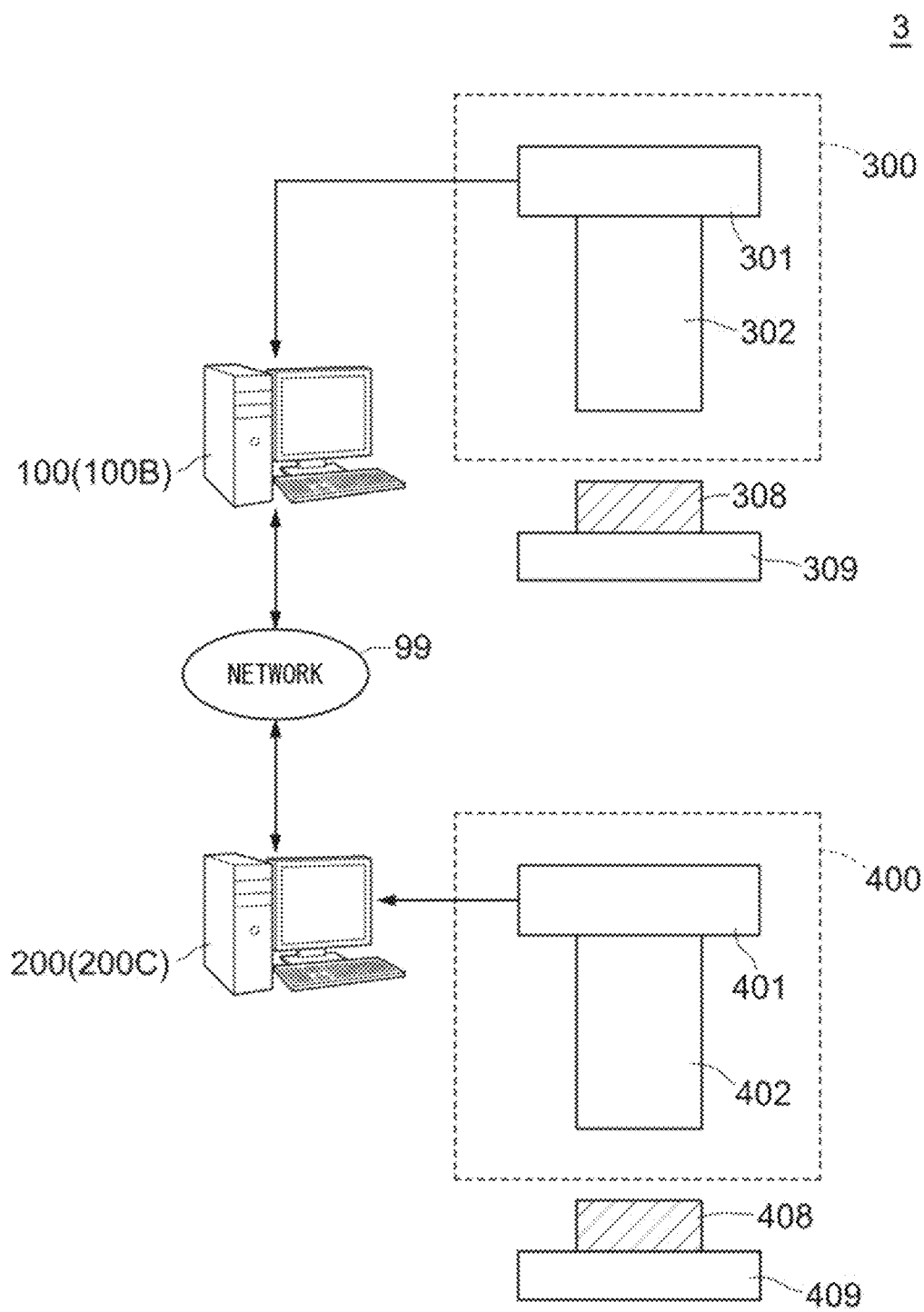
FIG. 20 shows a schematic configuration example of a disease analysis system 3.

Another aspect of the disease analysis system is described. FIG. 20 shows a configuration example of a disease analysis system 3. The disease analysis system 3 includes the vendor-side apparatus 100 and the user-side apparatus 200. The vendor-side apparatus 100 includes the processing unit 10 (10B), the input unit 16, and the output unit 17. The vendor-side apparatus 100 operates as an integrated-type disease analyzer 100B. The user-side apparatus 200 operates as a terminal apparatus 200C. The disease analyzer 100B is implemented as a general purpose computer, for example, and is a cloud-server-side apparatus that performs both the deep learning process and the disease analysis process described in the disease analysis system 1 above. The terminal apparatus 200C is implemented as a general purpose computer, for example, transmits an analysis target image to the disease analyzer 100B through the network 99, and receives an analysis result image from the disease analyzer 100B through the network 99.

In the disease analysis system 3, the integrated-type disease analyzer 100B installed on the vendor side has both functions of the training apparatus 100A and the disease analyzer 200A. Meanwhile, the disease analysis system 3 includes the terminal apparatus 200C, and provides the user-side terminal apparatus 200C with an input interface for the analysis image 78 and an output interface for an analysis result image. That is, the disease analysis system 3 is a cloud service-type system in which the vendor side that performs the deep learning process and the disease analysis process provides an input interface for providing the analysis image 78 to the user side and the output interface for providing the analysis result 83 to the user side. The input interface and the output interface may be integrated.

The disease analyzer 100B is connected to the imaging apparatus 300 and obtains the training image 70 captured by the imaging apparatus 300.

The terminal apparatus 200C is connected to the imaging apparatus 400 and obtains the analysis target image 78 captured by the imaging apparatus 400.

<Hardware Configuration>

The hardware configuration of the disease analyzer 100B is the same as the hardware configuration of the vendor-side apparatus 100 shown in FIG. 7. The hardware configuration of the terminal apparatus 200C is the same as the hardware configuration of the user-side apparatus 200 shown in FIG. 8.

<Function Block and Processing Procedure>

Figure 21:
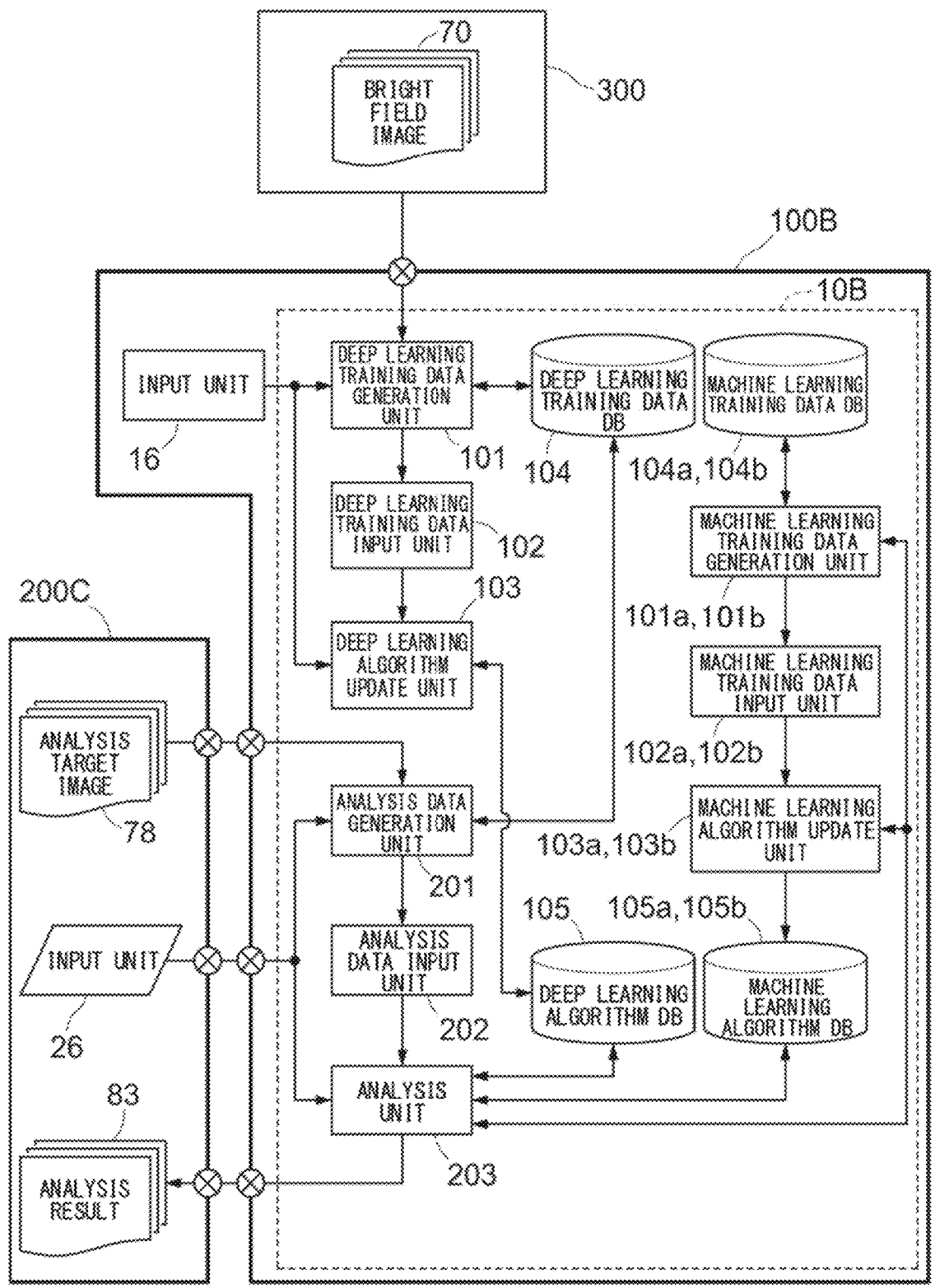
FIG. 21 is a block diagram for describing an example of functions of an integrated-type disease analyzer 100B.

FIG. 21 shows a function block diagram of the disease analyzer 100B. A processing unit 10B of the disease analyzer 100B includes the deep learning training data generation unit 101, the deep learning training data input unit 102, the deep learning algorithm update unit 103, the machine learning training data generation unit 101a, 101b, the machine learning training data input unit 102a, 102b, the machine learning algorithm update unit 103a, 103b, the analysis data generation unit 201, the analysis data input unit 202, and the analysis unit 203.

The processing unit 20B of the disease analyzer 200B performs the process shown in FIG. 10 during the deep learning process, performs the process shown in FIG. 13 or FIG. 14 during the machine learning process, and performs the process shown in FIG. 16 or FIG. 17 during the disease analysis process. With reference to the function blocks shown in FIG. 21, during the deep learning process, the processes of the steps S11, S12, S16, and S17 in FIG. 10 are performed by the deep learning training data generation unit 101. The process of step S13 in FIG. 10 is performed by the deep learning training data input unit 102. The process of step S14 in FIG. 10 is performed by the deep learning algorithm update unit 103. During the machine learning process, the processes of steps S111, S112, S114, and S115 in FIG. 13 are performed by the machine learning training data generation unit 101a. The process of step S113 is performed by machine learning training data input unit 102a. Alternatively, during the machine learning process, the processes of steps S1111, S1112, S1114, and S1115 in FIG. 14 are performed by the machine learning training data generation unit 101b. The process of step S1113 in FIG. 14 is performed by the machine learning training data input unit 102b. During the disease analysis process, the processes of the steps S21 and S22 in FIG. 16 are performed by the analysis data generation unit 201. The processes of steps S21 and S22 in FIG. 16 are performed by the analysis data generation unit 201. The processes of steps S23, S24, S25, and S27 in FIG. 16 is performed by the analysis data input unit 202. The process of step S26 in FIG. 16 is performed by the analysis unit 203. Alternatively, the processes of steps S121 and S122 in FIG. 17 are performed by the analysis data generation unit 201. The processes steps S123, S124, S125, and S127 in FIG. 17 are performed by the analysis data input unit 202. The process of step S126 in FIG. 16 is performed by the analysis unit 203.

The procedures of the deep learning process and the disease analysis process performed by the disease analyzer 100B are the same as the procedures of those performed by the training apparatus 100A and the disease analyzer 200A.

The processing unit 10B receives the analysis target image 78 from the user-side terminal apparatus 200C, and generates the deep learning training data 75 in accordance with the steps S11 to S17 shown in FIG. 10.

In step S26 shown in FIG. 12, the processing unit 10B transmits an analysis result including the analysis result 83 to the user-side terminal apparatus 200C. In the user-side terminal apparatus 200C, a processing unit 20C outputs the received analysis result to the output unit 27.

As described above, the user of the terminal apparatus 200C can obtain the analysis result 83 by transmitting the analysis target image 78 to the disease analyzer 100B.

According to the disease analyzer 100B, the user can use the discriminator without obtaining the training data database 104 and the algorithm database 105 from the training apparatus 100A. Accordingly, the service of discerning the type of cell and the feature of cell based on morphological classification can be provided as a cloud service.

OTHER EMBODIMENTS

The present disclosure is not limited to the above embodiment.

In the above embodiment, an example of a method for generating the deep learning training data 75 by converting the tone into brightness Y, first hue Cb, and second hue Cr, has been described. However, the conversion of the tone is not limited thereto. Without converting the tone, the three primary colors of red (R), green (G), and blue (B), for example, may be directly used. Alternatively, two primary colors obtained by excluding one hue from the primary colors may be used. Alternatively, one (for example green (G) only) obtained by selecting any one of the three primary colors of red (R), green (G), and blue (B) may be used. Conversion into the three primary colors of pigment of cyan (C), magenta (M), and yellow (Y) may be employed. Also, for example, the analysis target image 78 is not limited to a color image of the three primary colors of red (R), green (G), and blue (B), and may be a color image of two primary colors. It is sufficient that the image includes one or more primary colors.

In the training data generation method and the analysis data generation method described above, in step S11, the processing unit 10A, 20B, 10B generates the tone matrices 72y, 72cb, 72cr from the training image 70. However, the training image 70 may be the one converted into brightness Y, first hue Cb, and second hue Cr. That is, the processing unit 10A, 20B, 10B may originally obtain brightness Y, first hue Cb, and second hue Cr, directly from the virtual slide scanner or the like, for example. Similarly, in step S21, although the processing unit 20A, 20B, 10B generates the tone matrices 72y, 72cb, 72cr from the analysis target image 78, the processing unit 20A, 20B, 10B may originally obtain brightness Y, first hue Cb, and second hue Cr, directly from the virtual slide scanner or the like, for example.

Other than RGB and CMY, various types of color spaces such as YUV and CIE L*a*b* can be used in image obtainment and tone conversion.

In the tone vector data 74 and the tone vector data 80, for each pixel, information of tone is stored in the order of brightness Y, first hue Cb, and second hue Cr. However, the order of storing the information of tone and the handling order thereof are not limited thereto. However, the arrangement order of the information of tone in the tone vector data 74 and the arrangement order of information of tone in the tone vector data 80 are preferably the same with each other.

In each image analysis system, the processing unit 10A, 10B is realized as an integrated device. However, the processing unit 10A, 10B may not necessarily be an integrated device. Instead, a configuration may be employed in which the CPU 11, the memory 12, the storage unit 13, the GPU 19 and the like are provided at separate places; and these are connected through a network. Also, the processing unit 10A, 10B, the input unit 16, and the output unit 17 may not necessarily be provided at one place, and may be respectively provided at separate places and communicably connected with one another through a network. This also applies to the processing unit 20A, 20B, 20C.

In the disease analysis support system described above, function blocks of the deep learning training data generation unit 101, the machine learning training data generation unit 101a, 101b, the deep learning training data input unit 102, the machine learning training data input unit 102a, 102b, the deep learning algorithm update unit 103, the machine learning algorithm update unit 103a, 103b, the analysis data generation unit 201, the analysis data input unit 202, and the analysis unit 203 are executed by the single CPU 11 or the single CPU 21. However, these function blocks may not necessarily be executed by a single CPU, and may be executed in a distributed manner by a plurality of CPUs. These function blocks may be executed in a distributed manner by a plurality of GPUs, or may be executed in a distributed manner by a plurality of CPUs and a plurality of GPUs.

In the disease analysis support system described above, the program for performing the process of each step described in FIG. 10 and FIG. 12 is stored in advance in the storage unit 13, 23. Instead, the program may be installed in the processing unit 10B, 20B from a computer-readable non-transitory tangible storage medium 98 such as a DVD-ROM or a USB memory, for example. Alternatively, the processing unit 10B, 20B may be connected to the network 99 and the program may be downloaded from, for example, an external server (not shown) through the network 99 and installed.

In each disease analysis system, the input unit 16, 26 is an input device such as a keyboard or a mouse, and the output unit 17, 27 is realized as a display device such as a liquid crystal display. Instead, the input unit 16, 26 and the output unit 17, 27 may be integrated to realize a touch-panel-type display device. Alternatively, the output unit 17, 27 may be implemented by a printer or the like.

In each disease analysis system described above, the imaging apparatus 300 is directly connected to the training apparatus 100A or the disease analyzer 100B. However, the imaging apparatus 300 may be connected to the training apparatus 100A or the disease analyzer 100B via the network 99. Similarly, with respect to the imaging apparatus 400, although the imaging apparatus 400 is directly connected to the disease analyzer 200A or the disease analyzer 200B, the imaging apparatus 400 may be connected to the disease analyzer 200A or the disease analyzer 200B via the network 99.

[Effect of Discriminator]
<Training of Deep Learning Algorithm and Machine Learning Algorithm>

A total of 3,261 peripheral blood (PB) smear preparations were used for evaluation. The peripheral blood (PB) smear preparations included 1,165 peripheral blood (PB) smear preparations (myelodysplastic syndrome (n=94), myeloproliferative neoplasm (n=127), acute myeloid leukemia (n=38), acute lymphoblastic leukemia (n=27), malignant lymphoma (n=324), multiple myeloma (n=82), and non-neoplastic blood disease (n=473)), which were derived from subjects having blood diseases and which were obtained in Juntendo University Hospital during 2017 to 2018. PB smear preparation slides were stained with May Grunwald-Giemsa and created by a smear preparation creation apparatus SP-10 (manufactured by Sysmex Corporation). From the PB smear preparation slides, a total of 703,970 digitized cell images were obtained by using a blood cell differential automatic analyzer DI-60 (manufactured by Sysmex Corporation). From the images, deep learning training data 75 was generated according to the deep learning training data generation method described above.

As the first computer algorithm, a deep learning algorithm was used. As for the deep learning algorithm, Convolutional Neural Network (CNN) was used as the first neural network, and Fully Connected Neural Network (FCNN) was used as the second neural network, and discernment as to the type of cell and the type of abnormal finding was performed.

As the second computer algorithm, Extreme Gradient Boosting (EGB), which is a machine learning algorithm, was used, to construct an automatic disease analysis support system.

Figure 22A:
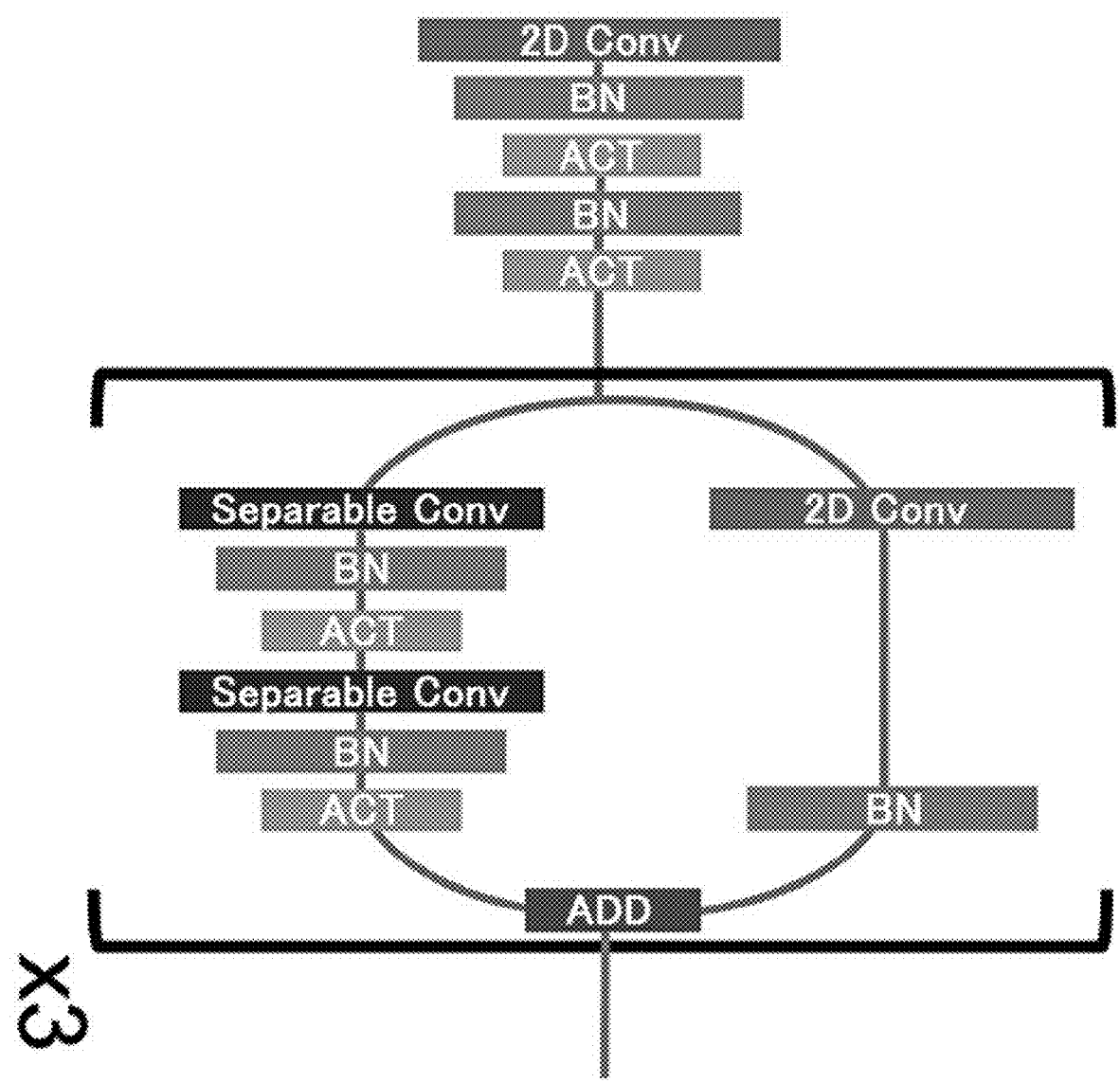
FIG. 22A shows the structure of a first part of a discriminator used in Example.
Figure 22B:
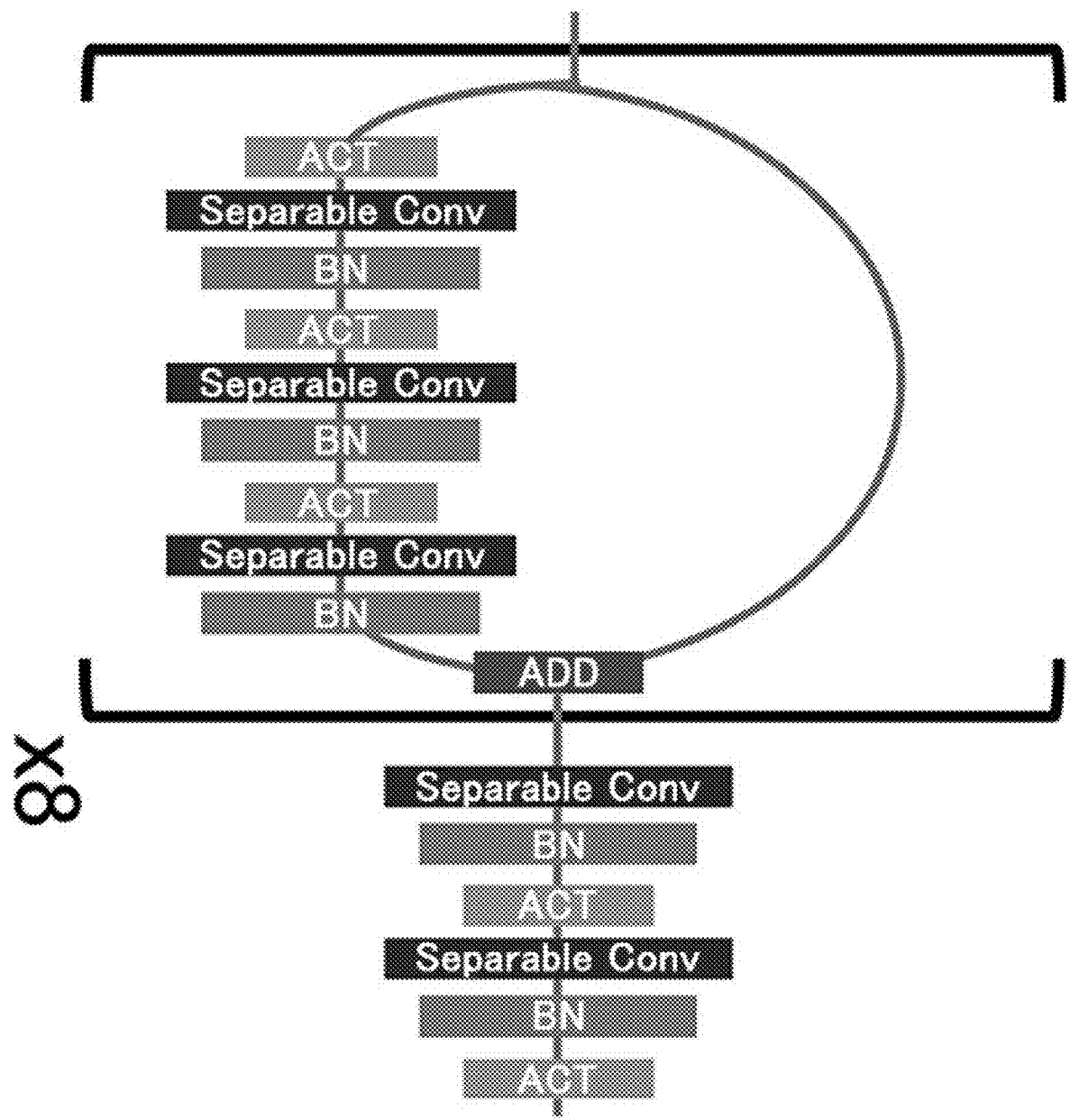
FIG. 22B shows the structure of a second part of a discriminator used in Example.
Figure 22C:
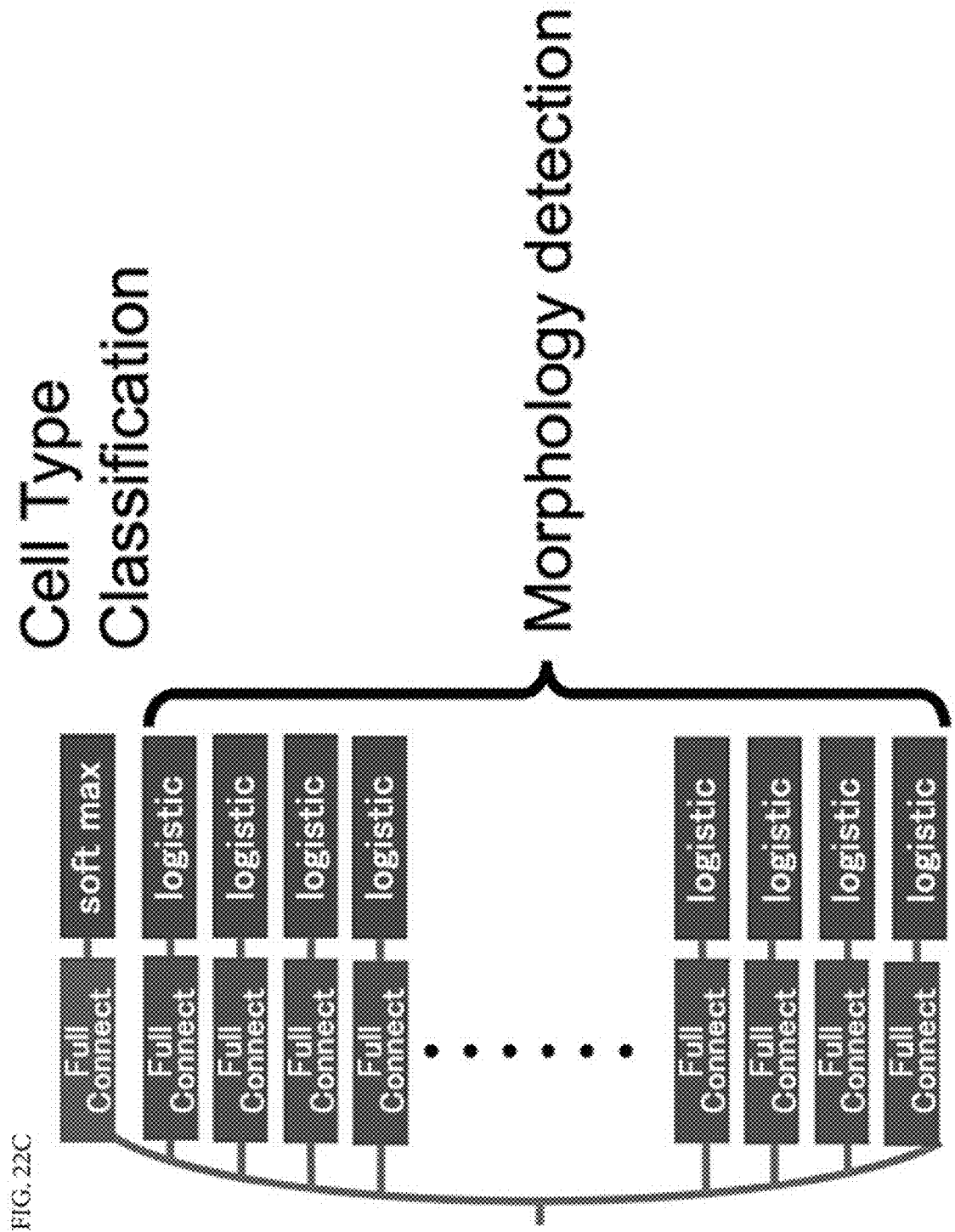
FIG. 22C shows the structure of a third part of a discriminator used in Example.
Figure 26A:
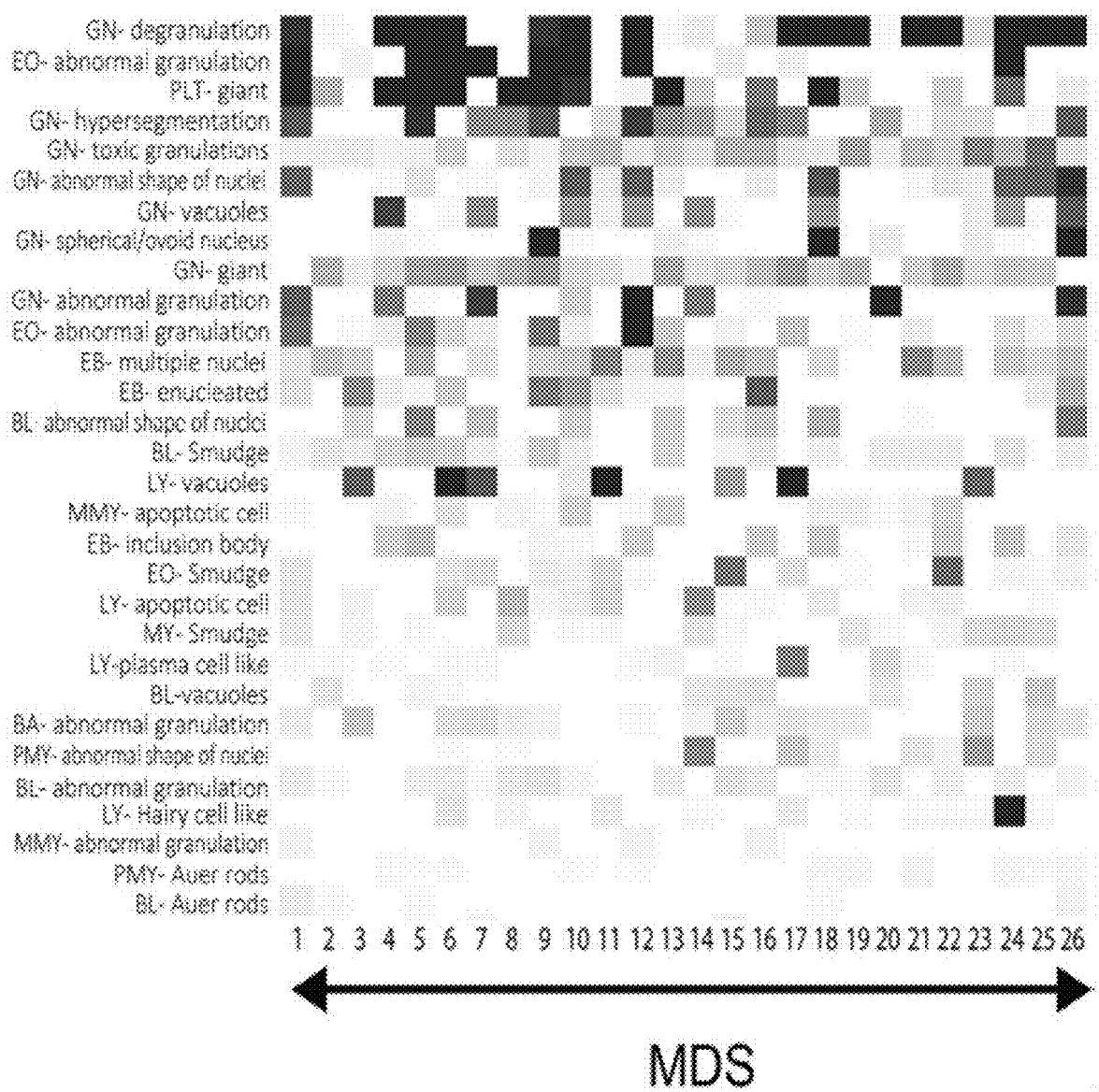
FIG. 26A is a first part of a heat map of abnormal findings contributing to disease analysis.
Figure 26B:
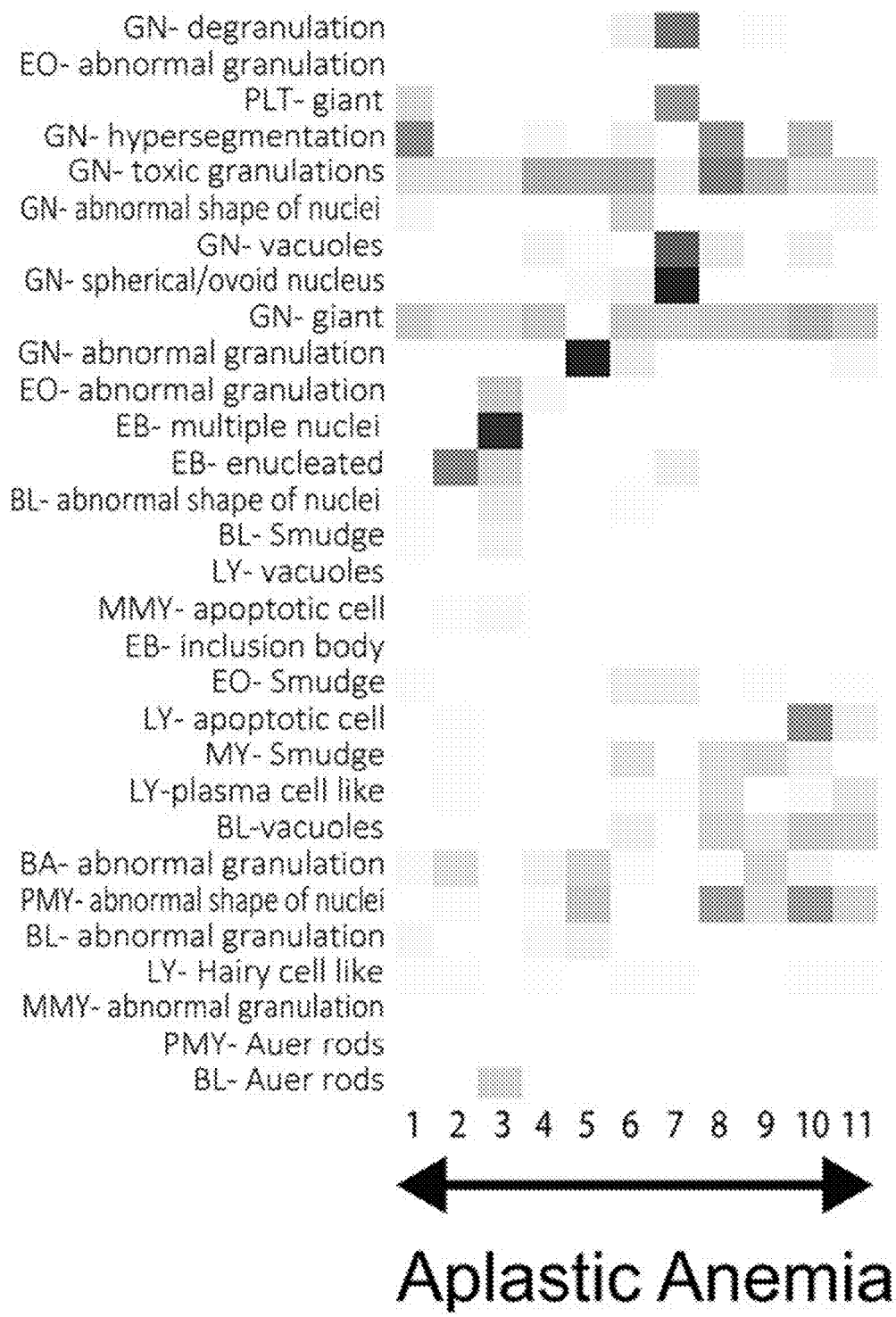
FIG. 26B is a second part a heat map of abnormal findings contributing to disease analysis.
Figure 26C:
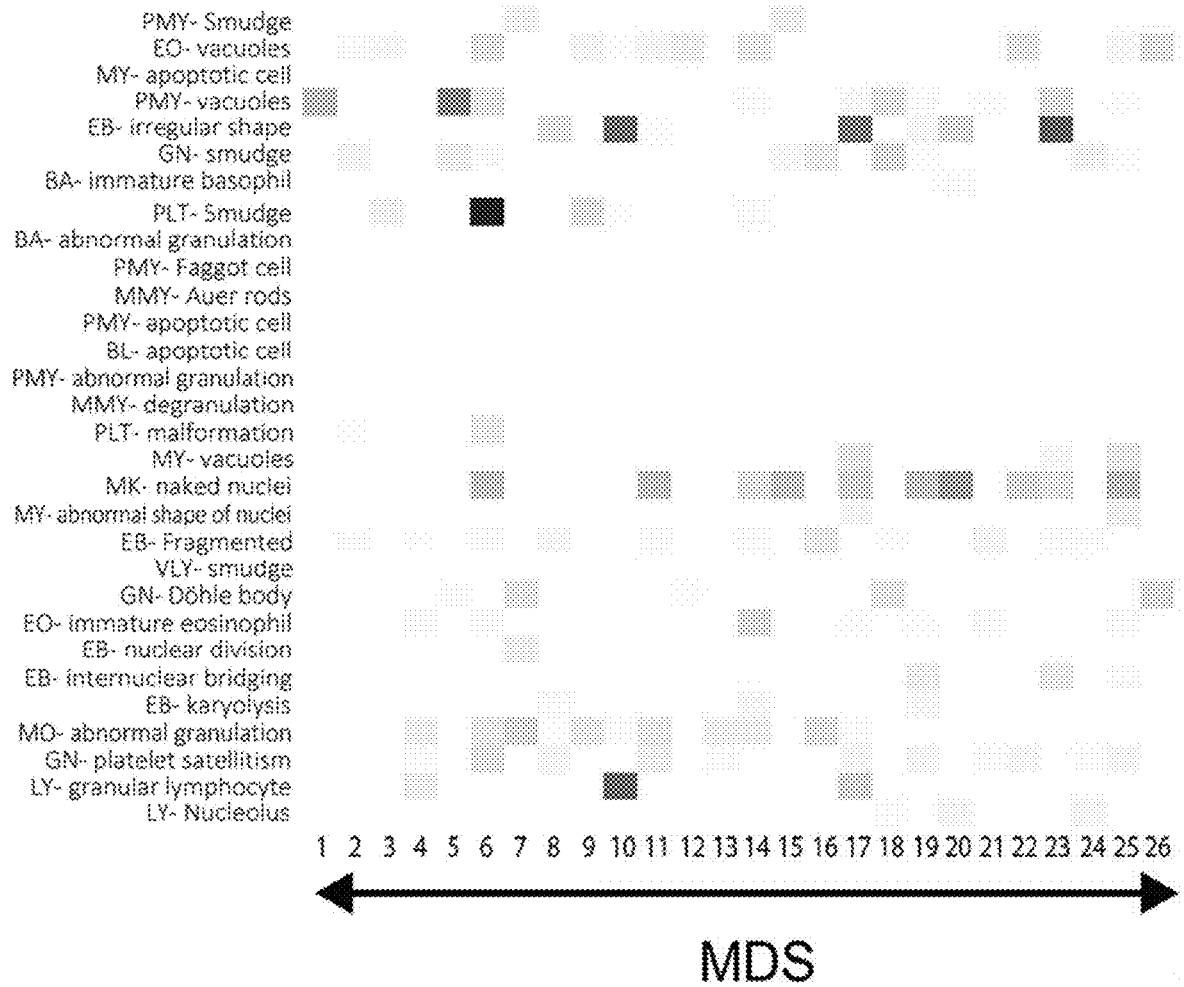
FIG. 26C is a third part of a heat map of abnormal findings contributing to disease analysis.
Figure 26D:
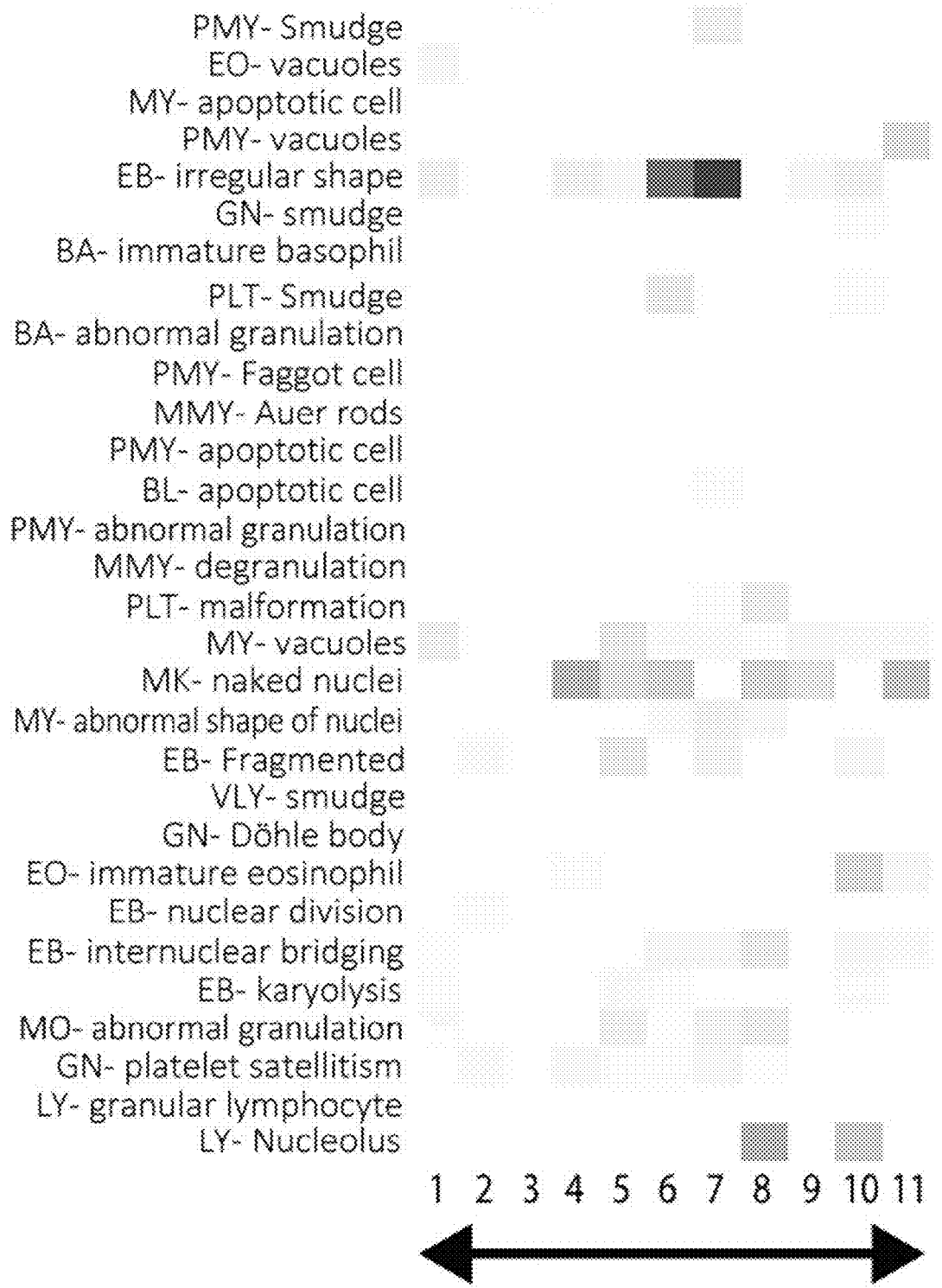
FIG. 26D is a fourth part of a heat map of abnormal findings contributing to disease analysis.

FIGS. 22A, 22B, and 22C show configurations of the discriminator used in Example. In order to simultaneously detect the type of cell and the type of abnormal finding, the deep learning algorithm was systematized.

This deep learning algorithm is composed of two major modules, i.e., "CNN module" and "FCNN module". The CNN module extracts features expressed by tone vector data from images captured by DI-60. The FCNN module analyzes the features extracted by the CNN module, and classifies cell images into 17 types of cells, as well as 97 features of abnormal findings such as the size and shape of cells and nuclei, cytoplasm image patterns, and the like.

"CNN module" is composed of two sub-modules. The first (upstream) sub-module has three identical blocks, and each block has two parallel paths each composed of several convolution network layers. These layers optimize extraction of a feature to the next block on the basis of on input image data and output parameters. The second (downstream) sub-module includes eight consecutive blocks. Each block has two parallel paths composed of a series of convolution layers and a path that does not include convolution components. This is called Residual Network (ResNet). The ResNet functions as a buffer for preventing saturation of the system.

Respective layers of separable convolution, exception-based convolution layer (Cony 2D), batch normalization layer (BN), and activation layer (ACT) have different roles. Separable convolution is a modified-type convolution called Xception. Cony 2D is a major component of a neural network that optimizes parameters when forming a "feature map" through extraction of features and processing of an image. ACT following the two layers of Cony 2D and BN is Rectified Linear Unit (ReLU). The first sub-module is connected to the second sub-module which is composed of eight consecutive similar blocks in order to create a feature map. Cony 2D bypasses in the second module in order to avoid unexpected deep layer saturation, which leads to effective calculation of weight due to backpropagation. The deep convolution neural network architecture above was implemented by backend of Keras and Tensorflow.

Discernment results of 17 types of cells and discernment results of 97 types of abnormal findings for each type of cell obtained by the first computer algorithm were used for training the machine learning algorithm. When discerning the types of abnormal findings for each type of cell, neutrophil was associated with abnormal findings without differentiating segmented neutrophil and band neutrophil. Among the abnormal findings shown in FIGS. 3A and 3B, items of "other abnormalities", "pseudo Chediak-Higashi granule-like", and "other abnormalities (including aggregation)" of platelet were excluded from analysis. The first information was generated from the discernment results of the types of abnormal findings for each type of cell, the second information was generated from the discernment results of the type of cell, and the generated first information and second information were inputted to XG Boost.

In order to train the deep learning algorithm, 703,970 digitized cell images were divided into 695,030 images for a training data set and 8,940 images for a validation data set.

In order to construct the system, peripheral blood cells of 89 myelodysplastic syndrome (MDS) cases and 43 aplastic anemia (AA) cases were used for the training. Next, using PB smear preparation images obtained from 26 MDS patients and 11 AA patients, the automatic disease analysis support system based on EGB was validated.

Discernment of cells used in the training were performed by two committee-authorized blood test laboratory technicians and one senior hematopathologist in accordance with the morphological criteria according to H20-A2 guideline of Clinical and Laboratory Standard Institute (CLSI) and the WHO classification of bone marrow tumor and acute leukemia revised in 2016. The training data set was classified into 17 types of cells and 97 types of abnormal findings.

FIG. 23 shows the number and the types of cell images for the training and the validation.

After the training, the evaluation data set was used to evaluate the performance of the first computer algorithm. FIG. 24 shows the accuracy of discernment results of the types of cells according to the trained first computer algorithm. The sensitivity and the specificity calculated by using an ROC curve were good.

FIG. 25 shows the accuracy of discernment results of the types of abnormal findings according to the trained first computer algorithm. The sensitivity, the specificity, and AUC calculated by using an ROC curve were good.

Therefore, it was shown that the discerning accuracy of the trained first computer algorithm was good.

Next, MDS and AA were differentiated by using the discriminator. FIGS. 26A, 26B, 26C, and 26D are diagrams showing the contribution degree of the types of abnormal findings for each type of cell expressed as a heat map of SHAP values. In the heat map shown in FIGS. 26A, 26B, 26C, and 26D, each column corresponds to a specimen of one patient, and each row corresponds to an abnormal finding for each type of cell. The patients from the first column at the left end to the 26th column correspond to MDS patients. The patients from the 27-th column to the 37-th column at the right end correspond to AA patients. The magnitude of the detection rate is expressed by the darkness/paleness of the heat map. FIGS. 26A, 26B, 26C, and 26D reveal that the detection rates of abnormal degranulation of neutrophil and abnormal granules of eosinophil and the detection rate of megathrombocyte in MDS patients are significantly higher than those of AA patients.

Figure 27:
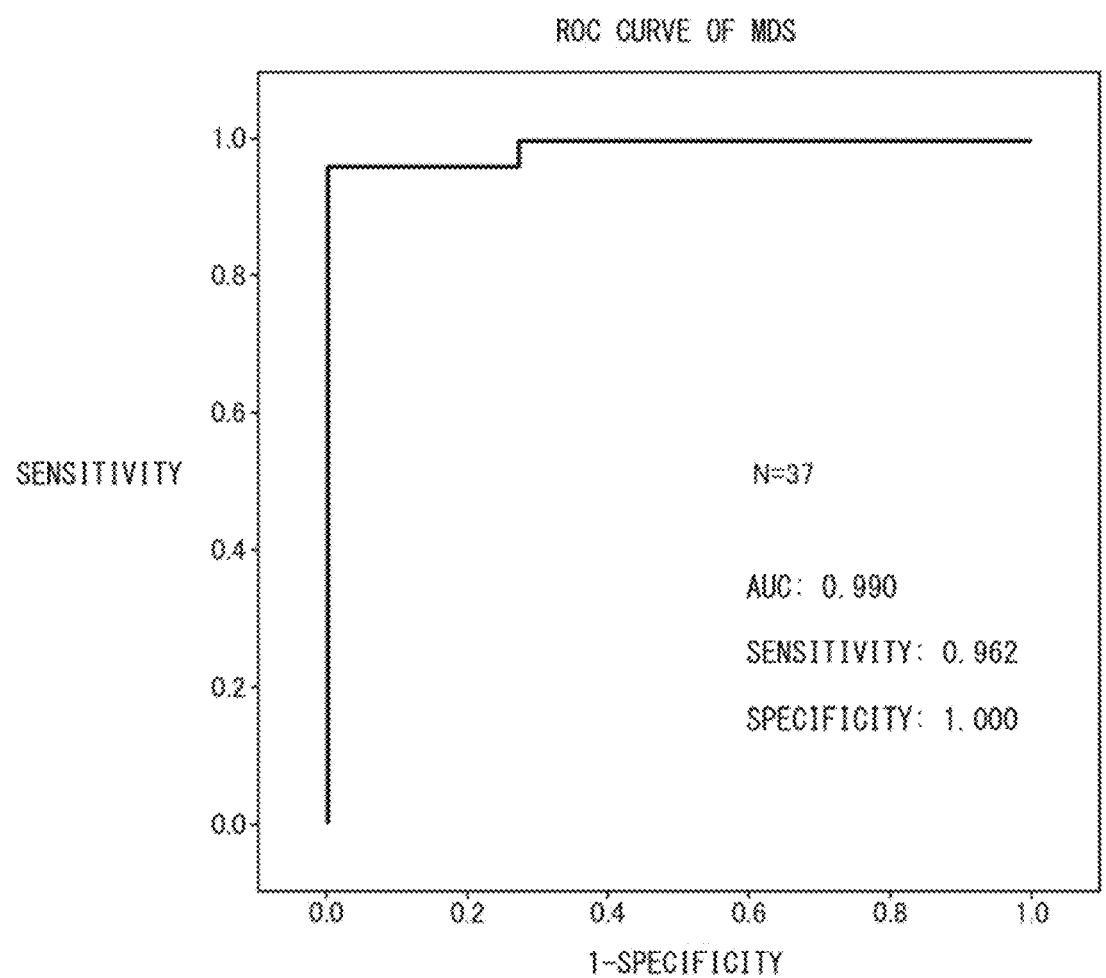
FIG. 27 shows a ROC curve of a disease analysis result.

FIG. 27 shows a result of evaluation as to the accuracy of the discriminator in differential diagnosis between MDS and AA. The evaluation was performed in terms of sensitivity, specificity, and AUC calculated by using an ROC curve. The sensitivity and the specificity of the discriminator were 96.2% and 100%, respectively, and AUC of the ROC curve was 0.990. Thus, high accuracy in differential diagnosis between MDS and AA was shown.

The discriminator described above was shown to be useful for supporting disease analysis.

What is claimed is:

1. A method for supporting disease analysis, the method comprising:
generating pixel vector data from images obtained from a plurality of analysis target cells in a specimen collected from a subject;
inputting the pixel vector data to a first deep learning algorithm having a first neural network structure, the first neural network structure comprising a first neural network and a second neural network;
inputting the pixel vector data to a second deep learning algorithm having a second neural network structure, the second neural network structure comprising the first neural network and a third neural network different from the second neural network;
processing the pixel vector data using the first neural network structure of the first deep learning algorithm to classify a first morphology of each analysis target cell in the images by
extracting, with the first neural network, a first feature quantity with respect to a cell feature reflecting abnormal finding in each analysis target cell based on the pixel vector data, and
classifying, with the second neural network, the first morphology comprising a type of abnormal finding in each analysis target cell based on the first feature quantity;
obtaining, from the first deep learning algorithm, first cell morphology classification information corresponding to types of abnormal findings in the specimen, on a basis of the first morphology, wherein the abnormal finding includes at least one type selected from the group consisting of: nucleus morphology abnormality; granulation abnormality; cell size abnormality; cell malformation; cytoclasis; vacuole; immature cell; presence of inclusion body; Döhle body; satellitism; nucleoreticulum abnormality; petal-like nucleus; increased N/C ratio; and bleb-like, smudge, and hairy cell-like morphologies;
processing the pixel vector data using the second neural network structure of the second deep learning algorithm to classify a second morphology of each analysis target cell in the images by
extracting, with the first neural network, a second feature quantity with respect to a cell feature reflecting cell type in each analysis target cell based on the pixel vector data, and
classifying, with the third neural network, the second morphology comprising a type of cell of each analysis target cell based on the first feature quantity;
obtaining, from the second deep learning algorithm, second cell morphology classification information corresponding to types of cells in the specimen, on a basis of the second morphology;
inputting the first cell morphology classification information and the second cell morphology classification information as feature quantities to a machine learning algorithm; and
processing the feature quantities by the machine learning algorithm to analyze a disease of the subject.

2. The method of claim 1, wherein
the nucleus morphology abnormality includes at least one type selected from hypersegmentation, hyposegmentation, pseudo-Pelger anomaly, ring-shaped nucleus, spherical nucleus, elliptical nucleus, apoptosis, polynuclearity, karyorrhexis, enucleation, bare nucleus, irregular nuclear contour, nuclear fragmentation, internuclear bridging, multiple nuclei, cleaved nucleus, nuclear division, and nucleolus abnormality,
the granulation abnormality includes at least one type selected from degranulation, granule distribution abnormality, toxic granule, Auer rod, Fagott cell, and pseudo Chediak-Higashi granule-like granule, and
the cell size abnormality includes megathrombocyte.

3. The method of claim 1, wherein
the second cell morphology classification information comprises information regarding a cell number for each type of cell.

4. The method of claim 1, wherein
the specimen is a blood specimen.

5. The method of claim 1, wherein
the first cell morphology classification information comprises information regarding a cell number for each type of abnormal finding.

6. The method of claim 1, further comprising:
discerning a type of abnormal finding for each type of cell of the analysis target cells.

7. The method of claim 1, wherein
the type of cell includes at least one type selected from neutrophil, eosinophil, platelet, lymphocyte, monocyte, and basophil.

8. The method of claim 7, wherein
the type of cell further includes at least one type selected from metamyelocyte, myelocyte, promyelocyte, blast, plasma cell, atypical lymphocyte, immature eosinophil, immature basophil, erythroblast, and megakaryocyte.

9. The method of claim 1, wherein
the machine learning algorithm is selected from tree, regression, neural network, Bayes, clustering, or ensemble learning.

10. The method of claim 9, wherein
the machine learning algorithm is gradient boosting tree.

11. The method of claim 1, wherein
the first cell morphology classification information comprises obtaining a probability that each analysis target cell belongs to each of a plurality of cell morphology classifications corresponding to types of abnormal findings, calculating a sum of the probability for each type of the plurality of cell morphology classifications, and obtaining the sum as the first cell morphology classification information.

12. The method of claim 1, wherein
the disease is a hematopoietic system disease.

13. The method of claim 12, wherein
the hematopoietic system disease is aplastic anemia or myelodysplastic syndrome.

14. The method of claim 1,
wherein the first neural network is a convolution connect neural network, and
wherein the second neural network and the third neural network are each full connect neural networks.

15. An apparatus for supporting disease analysis, the apparatus comprising
at least one processing unit, wherein
the at least one processing unit is configured to:
  generate pixel vector data from images obtained from a plurality of analysis target cells in a specimen collected from a subject;
  input the pixel vector data to a first deep learning algorithm having a first neural network structure, the first neural network structure comprising a first neural network and a second neural network;
  input the pixel vector data to a second deep learning algorithm having a second neural network structure, the second neural network structure comprising the first neural network and a third neural network different from the second neural network;
  process the pixel vector data using the first neural network structure of the first deep learning algorithm to classify a first morphology of each analysis target cell in the images by
    extracting, with the first neural network, a first feature quantity with respect to a cell feature reflecting abnormal finding in each analysis target cell based on the pixel vector data, and
    classifying, with the second neural network, the first morphology comprising a type of abnormal finding in each analysis target cell based on the first feature quantity;
  obtain, from the first deep learning algorithm, first cell morphology classification information corresponding to types of abnormal findings in the specimen, on a basis of the first morphology, wherein the abnormal finding includes at least one type selected from the group consisting of: nucleus morphology abnormality; granulation abnormality; cell size abnormality; cell malformation; cytoclasis; vacuole; immature cell; presence of inclusion body; Döhle body; satellitism; nucleoreticulum abnormality; petal-like nucleus; increased N/C ratio; and bleb-like, smudge, and hairy cell-like morphologies;
  process the pixel vector data using the second neural network structure of the second deep learning algorithm to classify a second morphology of each analysis target cell in the images by
    extracting, with the first neural network, a second feature quantity with respect to a cell feature reflecting cell type in each analysis target cell based on the pixel vector data, and
    classifying, with the third neural network, the second morphology comprising a type of cell of each analysis target cell based on the first feature quantity;
  obtain, from the second deep learning algorithm, second cell morphology classification information corresponding to types of cells in the specimen, on a basis of the second morphology;
  input the first cell morphology classification information and the second cell morphology classification information as feature quantities to a machine learning algorithm; and
  process the feature quantities by the machine learning algorithm to analyze a disease of the subject.

16. A non-transitory computer-readable storage medium having stored therein a program for supporting disease analysis, the program configured to cause a computer to execute a method comprising:
  generating pixel vector data from images obtained from a plurality of analysis target cells in a specimen collected from a subject;
  inputting the pixel vector data to a first deep learning algorithm having a first neural network structure, the first neural network structure comprising a first neural network and a second neural network;
  inputting the pixel vector data to a second deep learning algorithm having a second neural network structure, the second neural network structure comprising the first neural network and a third neural network different from the second neural network;
  processing the pixel vector data using the first neural network structure of the first deep learning algorithm to classify a first morphology of each analysis target cell in the images by
    extracting, with the first neural network, a first feature quantity with respect to a cell feature reflecting abnormal finding in each analysis target cell based on the pixel vector data, and
    classifying, with the second neural network, the first morphology comprising a type of abnormal finding in each analysis target cell based on the first feature quantity;
  obtaining, from the first deep learning algorithm, first cell morphology classification information corresponding to types of abnormal findings in the specimen, on a basis of the first morphology, wherein the abnormal finding includes at least one type selected from the group consisting of: nucleus morphology abnormality; granulation abnormality; cell size abnormality; cell malformation; cytoclasis; vacuole; immature cell; presence of inclusion body; Döhle body; satellitism; nucleoreticulum abnormality; petal-like nucleus; increased N/C ratio; and bleb-like, smudge, and hairy cell-like morphologies;
  processing the pixel vector data using the second neural network structure of the second deep learning algorithm to classify a second morphology of each analysis target cell in the images by
    extracting, with the first neural network, a second feature quantity with respect to a cell feature reflecting cell type in each analysis target cell based on the pixel vector data, and
    classifying, with the third neural network, the second morphology comprising a type of cell of each analysis target cell based on the first feature quantity;
  obtaining, from the second deep learning algorithm, second cell morphology classification information corresponding to types of cells in the specimen, on a basis of the second morphology;

inputting the first cell morphology classification information and the second cell morphology classification information as feature quantities to a machine learning algorithm; and processing the feature quantities by the machine learning algorithm to analyze a disease of the subject.

17. A training method for a machine learning algorithm for supporting disease analysis, the training method comprising:

generating pixel vector data from images obtained from a plurality of analysis target cells in a specimen collected from a subject;

inputting the pixel vector data to a first deep learning algorithm having a first neural network structure, the first neural network structure comprising a first neural network and a second neural network;

inputting the pixel vector data to a second deep learning algorithm having a second neural network structure, the second neural network structure comprising the first neural network and a third neural network different from the second neural network;

processing the pixel vector data using the first neural network structure of the first deep learning algorithm to classify a first morphology of each analysis target cell in the images by extracting, with the first neural network, a first feature quantity with respect to a cell feature reflecting abnormal finding in each analysis target cell based on the pixel vector data, and classifying, with the second neural network, the first morphology comprising a type of abnormal finding in each analysis target cell based on the first feature quantity;

obtaining, from the first deep learning algorithm, first cell morphology classification information corresponding to types of abnormal findings in the specimen, on a basis of the first morphology, wherein the abnormal finding includes at least one type selected from the group consisting of: nucleus morphology abnormality; granulation abnormality; cell size abnormality; cell malformation; cytoclasis; vacuole; immature cell; presence of inclusion body; Döhle body; satellitism; nucleoreticulum abnormality; petal-like nucleus; increased N/C ratio; and bleb-like, smudge, and hairy cell-like morphologies;

processing the pixel vector data using the second neural network structure of the second deep learning algorithm to classify a second morphology of each analysis target cell in the images by extracting, with the first neural network, a second feature quantity with respect to a cell feature reflecting cell type in each analysis target cell based on the pixel vector data, and classifying, with the third neural network, the second morphology comprising a type of cell of each analysis target cell based on the first feature quantity;

obtaining, from the second deep learning algorithm, second cell morphology classification information corresponding to types of cells in the specimen, on a basis of the second morphology;

creating a first training set comprising the first cell morphology classification information and the second cell morphology classification information and a second training set comprising disease information of the subject;

inputting the first training set and the second training set to the machine learning algorithm; and training the machine learning algorithm using the first training set and the second training set to create a trained machine learning algorithm.

18. A training apparatus for a machine learning algorithm for supporting disease analysis, the training apparatus comprising:

at least one processing unit, wherein the at least one processing unit is configured to:

generate pixel vector data from images obtained from a plurality of analysis target cells in a specimen collected from a subject;

input the pixel vector data to a first deep learning algorithm having a first neural network structure, the first neural network structure comprising a first neural network and a second neural network;

input the pixel vector data to a second deep learning algorithm having a second neural network structure, the second neural network structure comprising the first neural network and a third neural network different from the second neural network;

process the pixel vector data using the first neural network structure of the first deep learning algorithm to classify a first morphology of each analysis target cell in the images by extracting, with the first neural network, a first feature quantity with respect to a cell feature reflecting abnormal finding in each analysis target cell based on the pixel vector data, and classifying, with the second neural network, the first morphology comprising a type of abnormal finding in each analysis target cell based on the first feature quantity;

obtain, from the first deep learning algorithm, first cell morphology classification information corresponding to types of abnormal findings in the specimen, on a basis of the first morphology, wherein the abnormal finding includes at least one type selected from the group consisting of: nucleus morphology abnormality; granulation abnormality; cell size abnormality; cell malformation; cytoclasis; vacuole; immature cell; presence of inclusion body; Döhle body; satellitism; nucleoreticulum abnormality; petal-like nucleus; increased N/C ratio; and bleb-like, smudge, and hairy cell-like morphologies;

process the pixel vector data using the second neural network structure of the second deep learning algorithm to classify a second morphology of each analysis target cell in the images by extracting, with the first neural network, a second feature quantity with respect to a cell feature reflecting cell type in each analysis target cell based on the pixel vector data, and classifying, with the third neural network, the second morphology comprising a type of cell of each analysis target cell based on the first feature quantity;

obtain, from the second deep learning algorithm, second cell morphology classification information corresponding to types of cells in the specimen, on a basis of the second morphology;

create a first training set comprising the first cell morphology classification information and the second cell morphology classification information and a second training set comprising disease information of the subject;

input the first training set and the second training set to the machine learning algorithm; and train the machine learning algorithm using the first training set and the second training set to create a trained machine learning algorithm.

19. A non-transitory computer-readable storage medium having stored therein a training program for a computer algorithm for supporting disease analysis, the training program configured to cause a computer to execute a method comprising:
- generating pixel vector data from images obtained from a plurality of analysis target cells in a specimen collected from a subject;
- inputting the pixel vector data to a first deep learning algorithm having a first neural network structure, the first neural network structure comprising a first neural network and a second neural network;
- inputting the pixel vector data to a second deep learning algorithm having a second neural network structure, the second neural network structure comprising the first neural network and a third neural network different from the second neural network;
- processing the pixel vector data using the first neural network structure of the first deep learning algorithm to classify a first morphology of each analysis target cell in the images by
  - extracting, with the first neural network, a first feature quantity with respect to a cell feature reflecting abnormal finding in each analysis target cell based on the pixel vector data, and
  - classifying, with the second neural network, the first morphology comprising a type of abnormal finding in each analysis target cell based on the first feature quantity;
- obtaining, from the first deep learning algorithm, first cell morphology classification information corresponding to types of abnormal findings in the specimen, on a basis of the first morphology, wherein the abnormal finding includes at least one type selected from the group consisting of: nucleus morphology abnormality; granulation abnormality; cell size abnormality; cell malformation; cytoclasis; vacuole; immature cell; presence of inclusion body; Döhle body; satellitism; nucleoreticulum abnormality; petal-like nucleus; increased N/C ratio; and bleb-like, smudge, and hairy cell-like morphologies;
- processing the pixel vector data using the second neural network structure of the second deep learning algorithm to classify a second morphology of each analysis target cell in the images by
  - extracting, with the first neural network, a second feature quantity with respect to a cell feature reflecting cell type in each analysis target cell based on the pixel vector data, and
  - classifying, with the third neural network, the second morphology comprising a type of cell of each analysis target cell based on the first feature quantity;
- obtaining, from the second deep learning algorithm, second cell morphology classification information corresponding to types of cells in the specimen, on a basis of the second morphology;
- creating a first training set comprising the cell morphology classification information and a second training set comprising disease information of the subject;
- inputting the first training set and the second training set to a machine learning algorithm; and
- training the machine learning algorithm using the first training set and the second training set to create a trained machine learning algorithm.

* * * * *